United States Patent [19]

Kojima et al.

[11] Patent Number: 4,777,184

[45] Date of Patent: Oct. 11, 1988

[54] PROSTAGLANDIN DERIVATIVES, THEIR PREPARATION AND USE

[75] Inventors: Koichi Kojima; Shigeo Amemiya; Kazuo Koyama; Nobuyoshi Iwata; Takeshi Oshima, all of Tokyo, Japan

[73] Assignee: Sankyo Company Limited, Tokyo, Japan

[21] Appl. No.: 857,146

[22] Filed: Apr. 29, 1986

[30] Foreign Application Priority Data

Apr. 30, 1985 [JP] Japan .................................. 60-92713

[51] Int. Cl.$^4$ .................. G07C 177/00; A01K 31/557
[52] U.S. Cl. ..................................... 514/530; 514/569; 514/573; 549/415; 548/252; 556/441; 560/56; 560/117; 560/119; 562/501; 562/499; 562/466; 564/188; 568/445; 568/819
[58] Field of Search ................. 560/119, 56, 117; 562/501, 499, 466; 564/188; 568/445, 819; 556/441; 549/415; 548/252; 514/569, 573, 530

[56] References Cited

U.S. PATENT DOCUMENTS 4,420,632 12/1983 Aristoff ................................ 560/119
4,517,202 5/1985 Bird ..................................... 560/119

FOREIGN PATENT DOCUMENTS 134246 3/1985 European Pat. Off. .
136779 4/1985 European Pat. Off. .
2012265 7/1979 United Kingdom ................ 560/119
84/02902 8/1984 World Int. Prop. O. .......... 560/119

Primary Examiner—Robert Gersil
Attorney, Agent, or Firm—Frishauf, Holtz, Goodman & Woodward

[57] ABSTRACT

Prostaglandin derivatives, and specifically derivatives of isocarbacyclin, have an optionally substituted methylene group as a substituent on the α-carbon atom of the α-side chain. They have a variety of physiological effects, notably a strong ability to inhibit blood platelet aggregation and a strong anti-ulcer activity.

30 Claims, No Drawings

PROSTAGLANDIN DERIVATIVES, THEIR PREPARATION AND USE

BACKGROUND OF THE INVENTION

The present invention relates to a series of new prostaglandin derivatives, which have a variety of valuable therapeutic activities, and provides processes for preparing these compounds and methods and compositions using them.

The prostaglandins generally are known to have a variety of valuable physiological activities and a variety of prostaglandin derivatives, particularly the carbacyclins and analogs thereof, have been used for proposed to be used for the treatment of thrombosis or related conditions as a result of their valuable ability to inhibit the aggregation of blood platelets.

The compound known by the trivial name "carbacyclin" is described, for example, in UK Patent Specification No. 2,012,265, which describes and claims a series of compounds which may be represented by the formula (A):

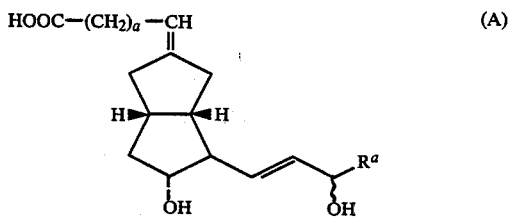

Carbacyclin is one of the isomers of the compound having this formula (A) in which a is 3 and $R^a$ represents a pentyl group. It should be noted that the α-side chain of this compound [the chain of formula HOOC—(CH$_2$)$_a$—CH=] contains an exo double bond (i.e. a double bond outside the bicyclooctane parent structure).

Subsequently, certain compounds having a related structure, which may be represented by the formula (B):

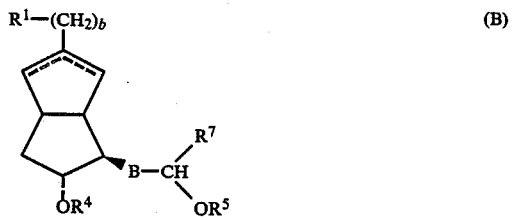

(where $R^1$, $R^4$, $R^5$, $R^7$ and B represent groups similar to those defined hereafter in relation to the compounds of the invention and b represents an integer from 1 to 6) were disclosed in U.S. patent application Ser. No. 634,351 filed July 25, 1984 abandoned in favor of Ser. No. 930,030, filed Nov. 7, 1986. Somewhat similar compounds are disclosed in a PCT Publication WO84/02902.

The compounds of formula (B) and similar compounds may be referred to as "isocarbacyclin" derivatives in that they can be isomeric with carbacyclin derivatives but, whereas the carbacyclin derivatives have an exo double bond in the α-side chain, the isocarbacyclin derivatives have an endo double bond (i.e. a double bond within the bicyclooctane system) at either the 2-position or the 3-position (indicated by the dotted line) of the bicyclooctane system. Certain of these isocarbacyclin derivatives have better physiological activity than do the known carbacyclin derivatives.

Although many chemical modifications have been made to the ω-side chain [i.e. the side chain at the 6-position of the bicyclooctane system, for example that represented by —B—CH($R^7$)—OR$^5$ in formula (B)] and although some modifications have been made in the substituent [e.g. that represented by $R^1$ in formula (B)] at the terminal position of the α-side chain, the prior art compounds—not only the closest prior art referred to above but also other, more remote, prostaglandin derivatives—generally have one thing in common: the α-side chain is a straight (unbranched) chain of carbon atoms or simply has a methyl branch and chemical modifications made to this chain have generally been relatively minor.

We have now surprisingly discovered that the introduction of a methylene or substituted methylene group at the α-carbon atom of this chain produces a series of prostaglandin derivatives which have extremely valuable physiological activities, such as vasodilating activity, bronchodilating activity, cell-protecting activity and, in particular, a strong inhibitory activity against blood platelet aggregation and a strong anti-ulcer effect.

BRIEF SUMMARY OF THE INVENTION

The compounds of the invention are those compounds of formula (I):

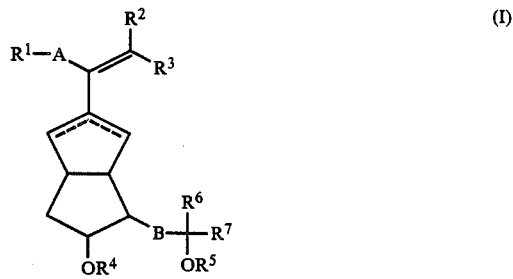

in which
the dotted line represents a double bond at either the 2-position or the 3-position;
$R^1$ represents a carboxy group, a tetrazolyl group, a carbamoyl group, a carbamoyl group having 1 or 2 substituents selected from the group consisting of substituents (a):
(a) $C_1$-$C_4$ alkyl groups, aliphatic carboxylic acyl groups, aromatic carboxylic acyl groups, $C_1$-$C_4$ alkanesulfonyl groups, arylsulfonyl groups, phenyl groups and phenyl groups having at least one $C_1$-$C_4$ alkyl substituent,
a formyl group, a group of formula

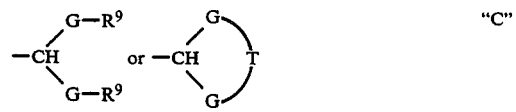

where:
G represents an oxygen or a sulfur atom;
$R^9$ represents a $C_1$-$C_4$ alkyl group; and
T represents a $C_2$-$C_5$ alkylene group, or a group of formula —CH$_2$OR$^{10}$ or —COCH$_2$OR$^{10}$ where:

R$^{10}$ represents a hydrogen atom, a C$_2$–C$_5$ aliphatic acyl group, an aromatic acyl group, an aralkyl group, a heterocyclic group having 5 or 6 ring atoms of which 1 or 2 are hetero-atoms selected from the group consisting of oxygen and sulfur atoms, a (C$_1$–C$_4$ alkoxy)methyl group, an alkylthioalkyl group in which each alkyl part is C$_1$–C$_4$, an aralkyloxymethyl group or a tri-substituted silyl group;

R$^2$ and R$^3$ are independently selected from the group consisting of hydrogen atoms and C$_1$–C$_4$ alkyl groups or R$^2$ and R$^3$, together with the carbon atoms to which they are attached, represent a C$_3$–C$_7$ cycloalkyl group;

R$^4$ and R$^5$ are independently selected from the group consisting of groups of formula —R$^{10}$;

R$^6$ represents a hydrogen atom or a C$_1$–C$_4$ alkyl group;

R$^7$ represents a C$_1$–C$_{12}$ alkyl group, a C$_1$–C$_{12}$ alkyl group having at least one substituent selected from the group consisting of substituents (b):

(b) halogen atoms, C$_1$–C$_4$ alkoxy groups, groups of formula —OR$^{10}$, aliphatic carboxylic acyl groups and aromatic carboxyclic acyl groups, a C$_3$–C$_{12}$ alkenyl group, a C$_3$–C$_{12}$ alkenyl group having at least one substituent selected from the group consisting of substituents (b), a C$_3$–C$_{12}$ alkynyl group, a C$_3$–C$_{12}$ alkynyl group having at least one substituent selected from the group consisting of substituents (b) or a group of formula —D—R$^8$, where:

D represents a single bond, a C$_1$–C$_6$ alkylene group, a C$_2$–C$_6$ alkenylene group or a C$_1$–C$_6$ alkylene or alkenylene group in which the carbon chain is interrupted by at least one oxygen or sulfur atom, or by a C$_3$–C$_7$ cycloalkylene group;

R$^8$ represents a C$_3$–C$_{10}$ cycloalkyl group, a C$_3$–C$_{10}$ cycloalkyl group having at least one C$_1$–C$_6$ alkyl substituent, a C$_5$–C$_{10}$ cycloalkenyl group, an aryl group or a heterocyclic group;

A represents a single bond, a C$_1$–C$_7$ alkylene group, a C$_1$–C$_7$ alkylene group having at least one fluorine substituent, a group of formula —CH=CH—(CH$_2$)$_n$— where n is 0 or an integer from 1 to 5, or a group of formula —(CH$_2$)$_p$—E—(CH$_2$)$_q$—, where:
p is 0 or an integer from 1 to 3,
q is an integer from 1 to 3, and
E is an oxygen or sulfur atom; and B represents a group of formula —CH$_2$CH$_2$—, —CH=CH— or —C≡C—, and pharmaceutically acceptable salts and esters thereof.

The invention further provides a pharmaceutical composition comprising at least one compound of formula (I) or pharmaceutically acceptable salt or ester thereof in admixture with a pharmaceutically acceptable carrier or diluent.

The invention still further provides a method of treating a mammal, which may be human or non-human, to relieve a thrombotic and/or ulcerative condition by administering thereto an effective amount of at least one compound of formula (I) or pharmaceutically acceptable salt or ester thereof.

DETAILED DESCRIPTION OF INVENTION

For the avoidance of doubt, the compounds of the present invention are hereinafter named as bicyclo[3.3.0]octane derivatives, in which the numbering system employed on the bicyclo[3.3.0]octane system is as follows:

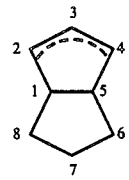

"D"

The configuration of the carbon atoms common to the cyclopentane and cyclopentene rings, that is the carbon atoms in the 1- and 5-positions, is preferably cis.

Where reference is made herein to "aryl" groups, either as such or as part of a larger group (e.g. an arylsulfonyl, aromatic acyl, aralkyl or aralkyloxy group), this is a carbocyclic aryl group preferably having from 6 to 14, more preferably from 6 to 10, ring carbon atoms (e.g. phenyl or 1- or 2-naphthyl) which may be substituted or unsubstituted. Where the group is substituted, the substituents are preferably selected from C$_1$–C$_4$ alkyl groups, C$_1$–C$_4$ alkoxy groups, hydroxy groups, halogen atoms, nitro groups, amino groups, C$_1$–C$_4$ alkylamino groups, dialkylamino groups where each alkyl part is C$_1$–C$_4$, C$_1$–C$_4$ haloalkyl groups, C$_2$–C$_7$ alkoxycarbonyl groups, aryl groups (themselves being as defined herein, preferably phenyl groups, and substituted or unsubstituted, albeit, if substituted, preferably not with aryl groups) and cyano groups.

Where R$^1$ represents a tetrazolyl group, this is preferably a 1H-tetrazol-5-yl group.

Where R$^1$ represents a carbamoyl group, this may be unsubstituted or may have one or two substituents selected from the group consisting of substituents (a) defined above. Where the substituents are C$_1$–C$_4$ alkyl groups, these may be straight or branched chain groups and examples include the methyl, ethyl, propyl, isopropyl and butyl groups. Where the substituents are aliphatic acyl groups, these are preferably groups having from 1 to 6, more preferably 2 to 4, carbon atoms and are more preferably alkanoyl groups which may be unsubstituted or have at least one substituent, preferably halogen atoms. Examples of such aliphatic acyl groups include the acetyl and trifluoroacetyl groups. Where the substituent is an aromatic acyl group, this is preferably an arylcarbonyl group in which the aryl part is as defined above and is most preferably a benzoyl group. Where the substituent is a C$_1$–C$_4$ alkanesulfonyl group, this is preferably a methanesulfonyl or ethanesulfonyl group. Where the substituent is an arylsulfonyl group, the aryl part is preferably as defined above and examples include the benzenesulfonyl and p-toluenesulfonyl groups. Where the substituent is a phenyl group, this may be unsubstituted or may have at least one C$_1$–C$_4$ alkyl substituent and examples include the phenyl and tolyl groups. Of the carbamoyl groups, we prefer the carbamoyl, phenylcarbamoyl and methanesulfonylcarbamoyl groups, more preferably the phenylcarbamoyl group.

Where $R^1$ represents a formyl group, this may be unprotected or may be protected by conversion to a group of formula

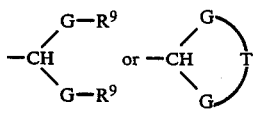

in which G, $R^9$ and T are as defined above. Where $R^9$ represents a $C_1$–$C_4$ alkyl group, this may be a straight or branched chain group and examples include the methyl, ethyl, propyl, isopropyl, butyl, sec-butyl, isobutyl and t-butyl groups. Where T represents a $C_2$–$C_5$ alkylene group, this is preferably an ethylene, propylene, trimethylene, butylene, tetramethylene or 2,2-dimethyltrimethylene group. G may represent an oxygen or sulfur atom, but is preferably an oxygen atom.

Where $R^1$ represents a group of formula —$CH_2OR^{10}$, this is a hydroxymethyl ($R^{10}$=H) or protected hydroxymethyl group. Protecting groups which may be represented by $R^{10}$ include: $C_2$–$C_5$ aliphatic carboxylic acyl groups, preferably alkanoyl groups, such as the acetyl, propionyl, butyryl, isobutyryl and valeryl groups; aromatic carboxylic acyl groups, preferably arylcarbonyl groups in which the aryl part is as defined above, preferably benzoyl or naphthoyl groups; aralkyl groups in which the aryl part is preferably as defined above and the alkyl part is preferably a $C_1$–$C_3$, more preferably $C_1$ alkyl group, for example the p-methoxybenzyl group; 5- or 6-membered heterocyclic groups containing oxygen or sulfur, which may be unsubstituted or have an alkoxy substituent, for example the 2-tetrahydropyranyl, 2-tetrahydrofuranyl, 4-methoxytetrahydropyran-4-yl or 2-tetrahydrothiopyranyl groups; methyl groups having a $C_1$–$C_4$ alkoxy substituent, for example the methoxymethyl and ethoxymethyl groups; alkylthioalkyl, particularly alkylthiomethyl, groups, such as the methylthiomethyl group; methyl groups having an aralkyloxy substituent, in which the aralkyl part is preferably as defined above, for example the benzyloxymethyl group; and trisubstituted silyl groups, in which the three substituents are the same or different and preferably selected from the group consisting of $C_1$–$C_4$ alkyl groups and aryl groups (the aryl groups preferably being as defined above), for example the trimethylsilyl, triethylsilyl, tripropylsilyl, t-butyldimethylsilyl and diphenyl-t-butylsilyl groups.

Where $R^1$ represents a group of formula —$COCH_2OR^{10}$, $R^{10}$ is preferably any one of the groups exemplified above. Similarly, where $R^4$ or $R^5$ represents a group of formula —$R^{10}$ or the substituent on the alkyl group represented by $R^7$ represents a group of formula —$OR^{10}$, $R^{10}$ is preferably as defined above. Where $R^1$ represents a group of formula —$CH_2OR^{10}$ or —$COCH_2OR^{10}$, $R^{10}$ is preferably a hydrogen atom or an aralkyl group. Where $R^4$ or $R^5$ represents a group of formula —$R^{10}$, $R^{10}$ is preferably a hydrogen atom or a 2-tetrahydropyranyl, benzoyl or dimethyl-t-butylsilyl group. Where $R^7$ represents an alkyl group having a substituent of formula —$OR^{10}$, $R^{10}$ is preferably a trisubstituted silyl group.

Where $R^2$ or $R^3$ represents a $C_1$–$C_4$ alkyl group, this is preferably a methyl, ethyl, propyl, isopropyl, butyl, sec-butyl, isobutyl or t-butyl group.

Where $R^2$ and $R^3$, together with the carbon atom to which they are attached represent a $C_3$–$C_7$ cycloalkyl group, this is preferably a cyclopropyl, cyclobutyl, cyclopentyl, cyclohexyl or cycloheptyl group.

Where $R^6$ represents a $C_1$–$C_4$ alkyl group, this may be any of the alkyl groups exemplified above in relation to $R^2$ and $R^3$.

Where $R^7$ represents an alkyl, alkenyl or alkynyl group, these may be unsubstituted or may have at least one substituents selected from the group consisting of: halogen atoms, for example the fluorine, chlorine or bromine atoms; $C_1$–$C_4$ alkoxy groups, for example the methoxy, ethoxy, propoxy, isopropoxy or butoxy groups; groups of formula —$OR^{10}$, for example as exemplified above; and acyl groups, for example as defined above in relation to the aliphatic and aromatic acyl groups which may be substituents on carbamoyl groups, and preferably the acetyl, propionyl or benzoyl groups. Of these, the fluorine, chlorine and $C_1$–$C_4$ alkoxy substituents are preferred, the $C_1$–$C_4$ alkoxy substituents being more preferred.

Where $R^7$ represents an alkyl group, this may be a straight or branched chain group and may be unsubstituted or have one or more substituents as defined above. Examples of such alkyl groups include the methyl, ethyl, propyl, isopropyl, butyl, isobutyl, pentyl, isopentyl, 1-methylpentyl, 2-methylpentyl, hexyl, heptyl, 1,1-dimethylpentyl, 1-methylhexyl, 2-methylhexyl, 2-ethylpentyl, octyl, 2-methyloctyl, nonyl, 2-methylnonyl, 2-ethyloctyl, decyl, 2-methyldecyl, and 2-ethyldecyl groups. Of these, the $C_3$–$C_{10}$ alkyl groups are preferred, for example the isopropyl, butyl, isobutyl, pentyl, isopentyl, 1-methylpentyl, 2-methylpentyl, hexyl, heptyl, 1,1-dimethylpentyl, 1-methylhexyl, 2-methylhexyl, 2-ethylpentyl, octyl, 2-methyloctyl and 2-ethyloctyl groups, and the most preferred groups are the $C_5$–$C_{10}$ alkyl groups, such as the pentyl, 1-methylpentyl, hexyl, 1,1-dimethylpentyl, 1-methylhexyl and 2-methylhexyl groups.

Where $R^7$ represents an alkenyl group, this may be unsubstituted or substituted as defined above and examples of preferred groups include the 1-butylvinyl, allyl, 2-propylallyl, 2-butenyl, 2-pentenyl, 4-pentenyl, 2-methyl-3-pentenyl, 4-methyl-3-pentenyl, 1-methyl-4-pentenyl, 1,1-dimethyl-4-pentenyl, 4-hexenyl, 5-hexenyl, 1,4-dimethyl-3-pentenyl, 5-heptenyl, 1-methyl-5-hexenyl, 1,1-dimethyl-5-hexenyl, 6-methyl-5-heptenyl, 2,6-dimethyl-5-heptenyl, 1,1,6-trimethyl-5-heptenyl, 6-methyl-5-octenyl, 2-methyl-6-ethyl-5-octenyl and 2,6-diethyl-5-octenyl groups. More preferred groups are the $C_3$–$C_{10}$ alkenyl groups, and the most preferred groups are the $C_5$–$C_{10}$ alkenyl groups such as the 1-butylvinyl, 2-propylallyl, 2-pentenyl, 4-pentenyl, 2-methyl-3-pentenyl, 4-methyl-3-pentenyl, 1-methyl-4-pentenyl, 1,1-dimethyl-4-pentenyl, 4-hexenyl, 5-hexenyl, 1,4-dimethyl-3-pentenyl, 5-heptenyl, 1-methyl-5-hexenyl, 1,1-dimethyl-5-hexenyl, 6-methyl-5-heptenyl and 2,6-dimethyl-5-heptenyl groups.

Where $R^7$ represents an alkynyl group, this is a $C_3$–$C_{12}$ alkynyl group, which may be a straight or branched chain group and which may be unsubstituted or substituted as defined above. Examples of such alkynyl groups include the propargyl, 2-butynyl, 2-pentynyl, 3-pentynyl, 1-methyl-2-butynyl, 2-hexynyl, 1-methyl-2-pentynyl, 1-methyl-3-pentynyl, 1,1-dimethyl-2-pentynyl, 1,1-dimethyl-3-pentynyl, 1,1-dimethyl-2-hexynyl and 1-methyl-3-hexynyl groups. More preferred groups are the $C_3$–$C_8$ alkynyl groups, and still more preferred groups are the $C_5$–$C_8$ alkynyl groups such as the 2-pentynyl, 3-pentynyl, 1-methyl-2-pentynyl, 1-methyl-3-hexynyl and 1-methyl-3-pentynyl groups. The most preferred group is the 1-methyl-3-pentynyl group.

Where D represents a $C_1$-$C_6$ alkylene or $C_2$-$C_6$ alkenylene group, this may be a straight or branched chain group and may optionally contain at least one oxygen or sulfur atom in its carbon chain. Any single carbon atom of the alkylene or alkenylene group may be substituted by a $C_2$-$C_6$ alkylene group, so as to form, with that carbon atom of the alkylene or alkenylene chain, a $C_3$-$C_7$ gem-cycloalkylene group. Examples of such alkylene and alkenylene groups include the methylene, ethylene, methylmethylene, trimethylene, dimethylmethylene, tetramethylene, 1-methyltrimethylene, 1,1-dimethylethylene, pentamethylene, 1,1-dimethyltrimethylene, hexamethylene, oxymethylene (—CH$_2$—O—), thiomethylene (—CH$_2$S—), methyleneoxymethylene (—CH$_2$—O—CH$_2$—), allylene (—CH$_2$—CH=CH—) and 1-pentylcyclopropyl groups. Of these, we particularly prefer $C_1$-$C_4$ alkylene groups and such groups in which the carbon chain is interrupted by a single oxygen or sulfur atom, for example the methylene, ethylene, methylmethylene, trimethylene, dimethylmethylene, oxymethylene and thiomethylene groups, and more particularly we prefer the methylene and oxymethylene groups. Alternatively, we prefer that D should represent a single bond.

Where $R^8$ represents a $C_3$-$C_{10}$ cycloalkyl group, this may be unsubstituted or may contain at least one, and preferably only one, $C_1$-$C_6$, more preferably $C_1$-$C_4$, alkyl substituent. The cycloalkyl group may be monocyclic, bicyclic or higher polycyclic. Examples of such groups include the cyclopropyl, cyclobutyl, cyclopentyl, 3-ethylcyclopentyl, cyclohexyl, 3-propylcyclohexyl, 4-methylcyclohexyl, cycloheptyl, bicyclo[4.3.0]non-7-yl and adamantyl groups, of which the $C_3$-$C_7$ cycloalkyl groups are preferred, and the cyclopentyl and cyclohexyl groups are more preferred.

Where $R^8$ represents a $C_5$-$C_{10}$ cycloalkenyl group, this may be a monocyclic, bicyclic or higher polycyclic ring system and examples include the 1-cyclopentenyl, 2-cyclopentenyl, 3-cyclopentenyl, 2-cyclohexenyl, 3-cyclohexenyl, 4-cyclohexenyl and bicyclo[4.3.0]-7-nonen-9-yl groups, of which the 2-cyclohexenyl group is preferred.

Where $R^8$ represents an aryl group, this is preferably as defined above in relation to aryl groups generally and is more preferably such a group having from 6 to 10 ring carbon atoms, which may be unsubstituted or may contain 1 or 2 substituents selected from $C_1$-$C_4$ alkyl groups, $C_1$-$C_4$ alkoxy groups, halogen atoms and trifluoromethyl groups. Examples of such aryl groups include the phenyl, o-tolyl, m-tolyl, p-tolyl, p-ethylphenyl, m-propylphentyl, m-methyoxyphenyl, p-methyoxyphenyl, o-ethoxyphenyl, o-fluorophenyl, m-fluorophenyl, p-fluorophenyl, m-chlorophenyl, p-chlorophenyl, p-bromophenyl, p-trifluoromethylphenyl, 3,4-dimethylphenyl, 3-fluoro-4-methylphenyl and 2,4-dichlorophenyl groups, of which preferred substituted phenyl groups are those substituted by a halogen atom, a $C_1$-$C_4$ alkyl group or a trifluoromethyl group, and more preferred groups are those substituted with a methyl group, a fluorine atom, a chlorine atom or a trifluoromethyl group; however, the unsubstituted phenyl group itself is most preferred.

Where $R^8$ represents a heterocyclic group, this may be an aromatic or non-aromatic group, preferably containing 5 or 6 ring atoms, of which at least one is a hetero-atom selected from the group consisting of oxygen, sulfur and nitrogen atoms. Preferred non-aromatic heterocyclic groups are the tetrahydrofuryl, tetrahydropyranyl, tetrahydrothienyl, pyrrolidinyl, piperidyl, morpholinyl and morpholino groups, of which the more preferred groups are the 2-tetrahydrofuryl and 2-tetrahydropyranyl groups. Preferred examples of aromatic heterocyclic groups include the furyl, thienyl, pyrrolyl, oxazolyl, thiazolyl, isoxazolyl and pyridyl groups, of which the preferred groups are the 2-thienyl and 3-thienyl groups.

Where A represents a $C_1$-$C_7$ alkylene, group, this may be unsubstituted or may have at least one fluorine substituent; there is no particular restriction upon the number of fluorine substituents, up to complete perfluorination. Examples of such alkylene groups include the methylene, ethylene, trimethylene, tetramethylene, pentamethylene, hexamethylene, heptamethylene, 1,1-difluorotrimethylene (—CF$_2$CH$_2$CH$_2$—), 2,2-difluorotrimethylene (—CH$_2$CF$_2$CH$_2$—) and 3,3-difluorotrimethylene (—CH$_2$CH$_2$CF$_2$—) groups. Alternatively, A can represent a single bond, a group of formula —CH=CH—(CH$_2$)$_n$— or —(CH$_2$)$_p$—E—(CH$_2$)$_q$—, in which n is 0 or an integer from 1 to 5, p is 0 or an integer from 1 to 3, q is an integer from 1 to 3 and E is an oxygen atom or a sulfur atom. Of these, we prefer that A should be a single bond, a straight chain $C_1$-$C_5$ alkylene group, a fluorinated $C_1$-$C_5$ alkylene group or a group of formula —(CH$_2$)$_p$—E—(CH$_2$)$_q$—, in which p and q each independently represents the integer 1 or 2 and E is as defined above, and we particularly prefer the groups of formula —(CH$_2$)$_3$—, —CH$_2$OCH$_2$— or —CH$_2$SCH$_2$—.

$R^2$ and $R^3$ preferably represent hydrogen atoms or $C_1$-$C_4$ alkyl groups and may be the same or different.

$R^6$ preferably represents a hydrogen atom or a methyl group.

B preferably represents a trans-vinylene group.

The bond represented by dotted line is preferably a double bond at the 2-position.

Where $R^1$ in the compounds of the invention represents a carboxy group, the resulting compounds are acids and hence can form salts and esters. There is no particular restriction upon the nature of such salts and esters, provided that, where they are intended for therapeutic use, they should be "pharmaceutically acceptable", which, as is well-known to those skilled in the art, means that they should not have a reduced activity (or unacceptably reduced activity) or an increased toxicity (or unacceptably increased toxicity) as compared with the free acids. Where the compounds are intended for non-therapeutic use, for example as intermediates in the preparation of other compounds, even these restrictions do not apply.

Examples of the preferred esters of the compounds of the invention include the following:

$C_1$-$C_{10}$ alkyl esters, for example the methyl, ethyl, propyl, isopropyl, butyl, t-butyl, pentyl, hexyl, heptyl, octyl, nonyl and decyl esters;

$C_3$-$C_7$ cycloalkyl esters, for example where the cycloalkyl group is any one of those $C_3$-$C_7$ cycloalkyl groups described herein in relation to $R^2$ and $R^3$;

aralkyl esters, in which the aryl part is preferably as defined above and the alkyl part is preferably a $C_1$-$C_3$, more preferably $C_1$ or $C_2$, alkyl group, for example the benzyl and p-bromobenzyl esters;

phenyl esters, in which the phenyl group is unsubstituted or substituted, preferably with at least one $C_1$-$C_4$ alkyl or acylamino group, for example the phenyl, tolyl and benzamidophenyl esters;

benzhydryl esters;

phenacyl esters; and geranyl esters.

Of these, the $C_1$–$C_{10}$ alkyl esters are preferred and the methyl esters are more preferred.

The compounds of the invention can likewise form salts which may, where the compounds are intended for therapeutic use, be pharmaceutically acceptable salts. Examples of such salts include:

salts with alkali or alkaline earth metals, such as the sodium, potassium, magnesium or calcium salts;

the ammonium salts;

quaternary ammonium salts, for example the tetramethylammonium, tetraethylammonium, benzyltriethylammonium and phenyltriethylammonium salts;

salts with alkylamines, cycloalkylamines or aralkylamines, such as the methylamine, ethylamine, dimethylamine, diethylamine, trimethylamine, triethylamine, N-methylhexylamine, cyclopentylamine, dicyclohexylamine, benzylamine, dibenzylamine, α-phenylethylamine and ethylenediamine salts;

salts with heterocyclic amines, wherein the heterocyclic groups is unsubstituted or has at least one $C_1$–$C_4$ alkyl substituent, for example the piperidine, morpholine, pyrrolidine, piperazine, pyridine, 1-methylpiperazine and 4-ethylmorpholine salts; and salts with amines containing a hydrophilic group, such as the monoethanolamine, ethyldiethanolamine and 2-amino-1-butanol salts.

The compounds of the invention can also, if desired, be employed in the form of an inclusion compound with a host compound, such as α-, β- or γ-cyclodextrin.

The compounds of the invention can exist in the form of various optical isomers, due to the presence of asymmetric carbon atoms in the cyclopentane ring and in the side chains, as geometric isomers, due to the double bond when $R^7$ represents an alkenyl group, or as positional isomers, due to, for example the double bond in the cyclopentene ring. The compounds of the invention may be obtained in the form of mixtures of such isomers, in which case, each individual isomer may be obtained by conventional isolation and resolution techniques, or the compounds may be employed as a mixture of such isomers. Although all of the isomers are represented herein by a single formula, it will be understood that all of the possible isomers are included within the scope of the present invention.

Preferred classes of compounds of the present invention are:

1. Compounds in which:

$R^1$ represents a carboxy group, a carbamoyl group, a carbamoyl group having 1 or 2 substituents selected from the group consisting of $C_1$–$C_4$ alkyl, phenyl and methanesulfonyl substituents, a formyl group, a group of formula

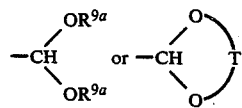

"E"

in which:

$R^9$ represents a $C_1$–$C_4$ alkyl group; and

T represents an ethylene, trimethylene or 2,2-dimethyltrimethylene group, a hydroxymethylcarbonyl group or a hydroxymethyl group, and, where $R^1$ represents a carboxy group, $C_1$–$C_{10}$ alkyl esters thereof.

2. Compounds in which:

$R^2$ and $R^3$ are independently selected from the group consisting of hydrogen atoms and $C_1$–$C_4$ alkyl groups.

3. Compounds in which:

$R^4$ and $R^5$ are independently selected from the group consisting of hydrogen atoms, tetrahydropyranyl groups, dimethyl-t-butylsilyl groups and benzoyl groups.

4. Compounds in which:

$R^6$ represents a hydrogen atom or a methyl group.

5. Compounds in which:

$R^7$ represents a $C_3$–$C_{10}$ alkyl group, a $C_3$–$C_{10}$ alkyl group having at least one substituent selected from the group consisting of fluorine, chlorine and $C_1$–$C_4$ alkoxy substituents, a $C_3$–$C_{10}$ alkenyl group, a $C_3$–$C_8$ alkynyl group, a group of formula —D—$R^8$ in which:

D represents a single bond, a $C_1$–$C_4$ alkylene group, an oxymethylene group or a thiomethylene group, and $R^8$ represents a $C_3$–$C_{10}$ cycloalkyl group, a $C_3$–$C_{10}$ cycloalkyl group having at least one $C_1$–$C_4$ alkyl substituent, a $C_5$–$C_6$ cycloalkenyl group, a thienyl group, a phenyl group or a phenyl group having at least one substituent selected from the group consisting of $C_1$–$C_4$ alkyl, $C_1$–$C_4$ alkoxy, trifluoromethyl and halogen substituents.

6. Compounds in which:

A represents a single bond, a straight chain $C_1$–$C_7$ alkylene group, a fluorinated $C_1$–$C_7$ alkylene group or a group of formula —CH=CH—$CH_2$— or —$(CH_2)_p$—E—$(CH_2)_q$— in which:

p is 0 or an integer from 1 to 3, q is an integer from 1 to 3, and

E is an oxygen or sulfur atom.

7. Compounds in which:

B is a trans-vinylene group.

8. Compounds in which the bond represented by the dotted line is a double bond at the 2-position.

9. Compounds in which:

$R^1$ represents a carboxy group, a hydroxymethyl group, a carbamoyl group or a carbamoyl group having a phenyl substituent, and, where $R^1$ represents a carboxy group, $C_1$–$C_{10}$ alkyl esters thereof;

$R^2$ and $R^3$ are independently selected from the group consisting of hydrogen atoms and $C_1$–$C_4$ alkyl groups;

$R^4$ and $R^5$ are independently selected from the group consisting of hydrogen atoms, tetrahydropyranyl groups, dimethyl-t-butylsilyl groups and benzoyl groups;

$R^6$ represents a hydrogen atom or a methyl group;

$R^7$ represents a $C_3$–$C_{10}$ alkyl group, a $C_3$–$C_{10}$ alkyl group having a $C_1$–$C_4$ alkoxy substituent, a $C_3$–$C_{10}$ alkenyl group, a $C_3$–$C_8$ alkynyl group or a group of formula —D—$R^8$, where D represents a single bond, a $C_1$–$C_4$ alkylene group, an oxymethylene group or a thiomethylene group, and $R^8$ represents a $C_3$–$C_{10}$ cycloalkyl group, a thienyl group, a phenyl group or a substituted phenyl group having at least one substituent selected from the group consisting of halogen atom, $C_1$–$C_4$ alkyl and trifluoromethyl substituents;

A represents a $C_1$–$C_5$ alkylene group, a fluorinated $C_1$–$C_5$ alkylene group or a group of formula —$(CH_2)_p$—E—$(CH_2)_q$— where:

E represents an oxygen or sulfur atom, p is 1 or 2, and q is 1 or 2; and the dotted line represents a double bond at the 2-position.

10. Compounds in which:

$R^1$ represents a carboxy group and methyl esters thereof;

$R^2$, $R^3$, $R^4$ and $R^5$ all represent hydrogen atoms;

$R^6$ represents a hydrogen atom or a methyl group;

$R^7$ represents a $C_5$–$C_{10}$ alkyl group, a $C_5$–$C_{10}$ alkenyl group, a $C_5$–$C_8$ alkynyl group or a group of formula —D—$R^8$, where D represents a single bond, a methylene group or an oxymethylene group, and $R^8$ represents a $C_3$–$C_7$ cycloalkyl group or a phenyl group;

A represents a trimethylene group, a methyleneoxymethylene group or a methylenethiomethylene group;

B represents a vinylene (—CH=CH—) group, preferably a trans-vinylene group; and the dotted line represents a double bond at the 2-position.

Specific examples of compounds of the present invention are given by the following formulae (I-1a), (I-1b), (I-2a), (I-2b), (I-3a), (I-3b) and (I-4):

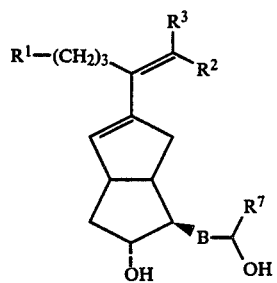
(I-1a)

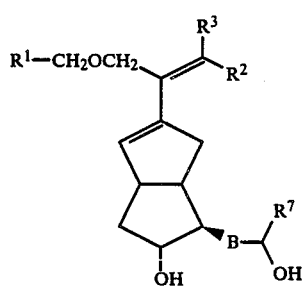
(I-1b)

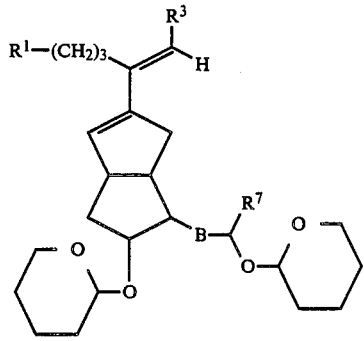
(I-2a)

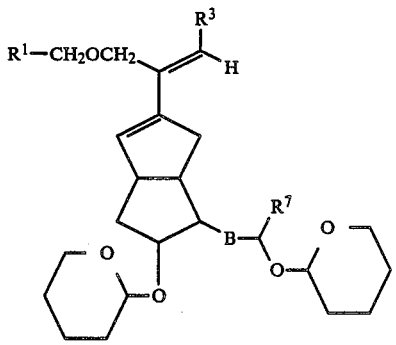
(I-2b)

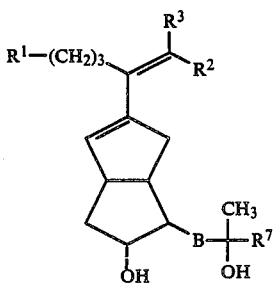
(I-3a)

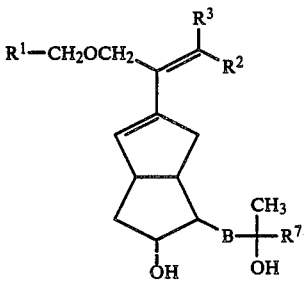
(I-3b)

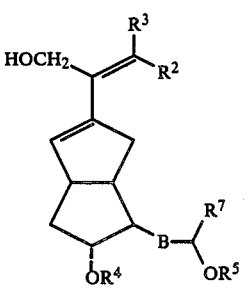
(I-4)

taken in conjunction with the corresponding Tables 1, 2, 3 and 4. Specifically, compounds of formula (I-1a) are as defined in Table 1 and are identified by a number and the suffix "a"; compounds of formula (I-1b) are defined in Table 1 and are identified by a number and the suffix "b"; compounds of formula (I-2a) are defined in Table 2 and are identified by a number and the suffix "a"; compounds of formula (I-2b) are defined in Table 2 and are identified by a number and the suffix "b"; compounds of formula (I-3a) are defined in Table 3 and are identified by a number and the suffix "a"; compounds of formula (I-3b) are defined in Table 3 and are identified by a number and the suffix "b"; and compounds of formula (I-4) are defined Table 4.

In the Tables, the following abbreviations are used:
Boz: benzoyl
Bu: butyl
iBu: isobutyl
tBu: t-butyl
Bz: benzyl
Dol: 1,3-dioxolan-2-yl
Dox: 1,3-dioxan-2-yl
Et: ethyl
Hp: heptyl
Hx: hexyl
cHx: cyclohexyl
Me: methyl
Mes: methanesulfonyl
Ph: phenyl
Pn: pentyl
cPn: cyclopentyl
cPr: cyclopropyl
Tezl: 1H-tetrazol-5-yl
THF: Tetrahydrofuryl
THP: Tetrahydropyranyl.

TABLE 1

| Cpd No. | $R^1$ | $R^2$ | $R^3$ | $R^7$ | B |
|---|---|---|---|---|---|
| 1a/b | COOH | H | H | Bu | —CH=CH— |
| 2a/b | COOH | H | H | Pn | —CH$_2$CH$_2$— |
| 3a/b | COOH | H | H | Pn | —CH=CH— |
| 4a/b | COOH | H | H | Pn | —C≡C— |
| 5a/b | COOH | H | Me | Pn | —CH=CH— |
| 6a/b | COOH | Me | Me | Pn | —CH=CH— |
| 7a/b | COOMe | H | H | Pn | —CH=CH— |
| 8a/b | CH$_2$OH | H | H | Pn | —CH=CH— |
| 9a/b | CHO | H | H | Pn | —CH=CH— |
| 10a/b | 5,5-diMeDox | H | H | Pn | —CH=CH— |
| 11a/b | CONHMes | H | H | Pn | —CH=CH— |
| 12a/b | COOH | H | H | iBu | —CH=CH— |
| 13a/b | COOH | H | H | 2-EtBu | —CH=CH— |
| 14a/b | COOH | H | H | Hx | —CH=CH— |
| 15a/b | COOH | H | H | 1-MePn | —CH=CH— |
| 16a/b | COOH | H | H | 1-MePn | —C≡C— |
| 17a/b | COOHx | H | H | 1-MePn | —CH=CH— |
| 18a/b | CH$_2$OH | H | H | 1-MePn | —CH=CH— |
| 19a/b | 5,5-DiMeDox | H | H | 1-MePn | —CH=CH— |
| 20a/b | COOH | H | H | 2-MePn | —CH=CH— |
| 21a/b | COOH | H | H | 3-MePn | —CH=CH— |
| 22a/b | CH$_2$OH | H | H | HP | —CH=CH— |
| 23a/b | COOH | H | H | 2-MeHx | —CH=CH— |
| 24a/b | COOH | H | H | 1-MeHx | —CH=CH— |
| 25a/b | COOH | H | H | 1,1-diMePn | —CH=CH— |
| 26a/b | COOH | H | Me | 1,1-diMePn | —CH=CH— |
| 27a/b | CHO | H | H | 1,1-diMePn | —CH=CH— |
| 28a/b | COOH | H | H | 1-FPn | —CH=CH— |
| 29a/b | COOH | H | H | 1,1-diFPn | —CH=CH— |
| 30a/b | COOH | H | H | 1,1-diFPn | —C≡C— |
| 31a/b | COOH | H | H | 1-PncPr | —CH=CH— |
| 32a/b | COOH | H | H | 5-MeOPn | —CH=CH— |
| 33a/b | COOH | H | H | 1-Me-4-MeOBu | —CH=CH— |
| 34a/b | COOH | H | H | 1,1-diMe-2-EtOEt | —CH=CH— |
| 35a/b | COOH | H | Me | 1,1-diMe-2-EtOEt | —CH=CH— |
| 36a/b | —C(:O)—CH$_2$OH | H | H | 1,1-diMe-2-EtOEt | —CH=CH— |
| 37a/b | COOH | H | H | —(CH$_2$)$_3$CH=CH$_2$ | —CH=CH— |
| 38a/b | CH$_2$OH | H | H | —(CH$_2$)$_3$CH=CH$_2$ | —CH=CH— |
| 39a/b | COOH | H | H | —CH$_2$CH=CHEt | —CH=CH— |
| 40a/b | COOH | H | H | —(CH$_2$)$_3$CH=CHMe | —CH=CH— |
| 41a/b | COOH | H | H | —(CH$_2$)$_3$CH=CHMe | —C≡C— |
| 42a/b | COOH | H | H | —C(:CH$_2$)Bu | —CH=CH— |
| 43a/b | COOH | H | Me | —C(:CH$_2$)Bu | —CH=CH— |
| 44a/b | COOH | H | H | 1-Me-5-Hexenyl | —CH=CH— |
| 45a/b | COOH | H | H | 1-Me-4-Pentenyl | —CH=CH— |
| 46a/b | 5,5-diMeDox | H | H | 1-Me-4-Pentenyl | —CH=CH— |
| 47a/b | COOH | H | H | —C(:CH$_2$)Pn | —CH=CH— |
| 48a/b | COOH | H | H | —C(:CH$_2$)Pn | —CH$_2$CH$_2$— |
| 49a/b | COOH | H | H | —C(:CH$_2$)Pn | —C≡C— |
| 50a/b | COOH | H | H | 1,4-diMe-3-Pentenyl | —CH=CH— |
| 51a/b | COOH | H | H | 6-Me-5-Heptenyl | —CH=CH— |
| 52a/b | COOH | H | H | 6-Me-5-Heptenyl | —C≡C— |
| 53a/b | COOH | H | H | 1,1-diMe-5-Hexenyl | —CH=CH— |
| 54a/b | —CH$_2$OH | H | H | 1,1-diMe-5-Hexenyl | —CH=CH— |
| 55a/b | —CHO | H | H | 1,1-diME-5-Hexenyl | —CH=CH— |
| 56a/b | 5,5-diMeDox | H | H | 1,1-diMe-5-Hexenyl | —CH=CH— |
| 57a/b | —COO(4-BozNH)Ph | H | H | 1,1-diMe-5-Hexenyl | —CH=CH— |
| 58a/b | COOH | H | H | 1,1-diMe-4-Pentenyl | —CH=CH— |
| 59a/b | COOMe | H | H | 1,1-diMe-4-Pentenyl | —CH=CH— |
| 60a/b | COOH | H | H | 1,6-diMeHept-5-enyl | —CH=CH— |
| 61a/b | COOH | H | H | 1,6-diMeHept-5-enyl | —CH$_2$CH$_2$— |

TABLE 1-continued

| Cpd No. | R¹ | R² | R³ | R⁷ | B |
|---|---|---|---|---|---|
| 62a/b | COOH | H | Me | 1,6-diMeHept-5-enyl | —CH=CH— |
| 63a/b | COOH | Et | Me | 1,6-diMeHept-5-enyl | —CH=CH— |
| 64a/b | CH₂OH | H | H | 1,6-diMeHept-5-enyl | —CH=CH— |
| 66a/b | Dox | H | H | 1,6-diMeHept-5-enyl | —CH=CH— |
| 67a/b | COOH | H | H | 2,6-diMeHept-5-enyl | —CH=CH— |
| 68a/b | COOH | H | H | 2,6-diMeHept-5-enyl | —CH₂CH₂— |
| 69a/b | COOH | H | H | 2,6-diMeHept-5-enyl | —C≡C— |
| 70a/b | COOMe | H | H | 2,6-diMeHept-5-enyl | —C≡C— |
| 71a/b | COOH | H | Me | 2,6-diMeHept-5-enyl | —CH=CH— |
| 72a/b | COOH | Me | Me | 2,6-diMeHept-5-enyl | —CH=CH— |
| 73a/b | COOH | Et | Me | 2,6-diMeHept-5-enyl | —CH=CH— |
| 74a/b | COOH | R² + R³ = gem-cPn | | 2,6-diMeHept-5-enyl | —CH=CH— |
| 75a/b | COOH | R² + R³ = gem-cHx | | 2,6-diMeHept-5-enyl | —CH=CH— |
| 76a/b | COOMe | H | H | 2,6-diMeHept-5-enyl | —CH=CH— |
| 77a/b | COOHp | H | H | 2,6-diMeHept-5-enyl | —CH=CH— |
| 78a/b | COOBz | H | H | 2,6-diMeHept-5-enyl | —CH=CH— |
| 79a/b | CH₂OH | H | H | 2,6-diMeHept-5-enyl | —CH=CH— |
| 80a/b | CH₂OBz | H | H | 2,6-diMeHept-5-enyl | —CH=CH— |
| 81a/b | COCH₂OH | H | H | 2,6-diMeHept-5-enyl | —CH=CH— |
| 82a/b | CHO | H | H | 2,6-diMeHept-5-enyl | —CH=CH— |
| 83a/b | —CH(OMe)₂ | H | H | 2,6-diMeHept-5-enyl | —CH=CH— |
| 84a/b | —CH(OEt)₂ | H | H | 2,6-diMeHept-5-enyl | —CH=CH— |
| 85a/b | Dol | H | H | 2,6-diMeHept-5-enyl | —CH=CH— |
| 86a/b | Tezl | H | H | 2,6-diMeHept-5-enyl | —CH=CH— |
| 87a/b | 5,5-diMeDox | H | H | 2,6-diMeHept-5-enyl | —CH=CH— |
| 88a/b | —CONHMes | H | H | 2,6-diMeHept-5-enyl | —CH=CH— |
| 89a/b | Dox | H | H | 2,7-diMeOct-6-enyl | —CH=CH— |
| 90a/b | —COOH | H | H | 2,2,6-triMe-Hept-5-enyl | —CH=CH— |
| 91a/b | —COOH | H | H | 6-EtOct-5-enyl | —CH=CH— |
| 92a/b | CH₂OH | H | H | 6-EtOct-5-enyl | —CH=CH— |
| 93a/b | COOH | H | H | 2-Pentynyl | —CH=CH— |
| 94a/b | CH₂OH | H | H | 2-Pentynyl | —CH=CH— |
| 95a/b | COOH | H | H | 1-Me-2-Pentynyl | —CH=CH— |
| 96a/b | COOH | H | H | 1-Me-2-Pentynyl | —CH₂CH₂— |
| 97a/b | COOH | H | H | 3-Pentynyl | —CH=CH— |
| 98a/b | COOH | H | H | 1-Me-3-Pentynyl | —CH=CH— |
| 99a/b | COOH | H | H | 1-Me-3-Pentynyl | —C≡C— |
| 100a/b | COOH | H | Me | 1-Me-3-Pentynyl | —CH=CH— |
| 101a/b | COOMe | H | H | 1-Me-3-Pentynyl | —CH=CH— |
| 102a/b | —CH(OMe)₂ | H | H | 1-Me-3-Pentynyl | —CH=CH— |
| 103a/b | Dox | H | H | 1-Me-3-Pentynyl | —CH=CH— |
| 104a/b | COOH | H | H | 1-Me-4-Hexynyl | —CH=CH— |
| 105a/b | COOH | H | Me | 1-Me-4-Hexynyl | —CH=CH— |
| 106a/b | COOH | H | H | 1,1-diMe-3-Pentynyl | —CH=CH— |
| 107a/b | COOH | H | H | 1-Me-3-Hexynyl | —CH=CH— |
| 108a/b | COOH | H | H | 1-Me-3-Hexynyl | —CH≡C— |

TABLE 1-continued

| Cpd No. | R¹ | R² | R³ | R⁷ | B |
|---|---|---|---|---|---|
| 109a/b | COOH | H | Me | 1-Me-3-Hexynyl | —C≡C— |
| 110a/b | COOMe | H | H | 1-Me-3-Hexynyl | —C≡C— |
| 111a/b | CH₂OH | H | H | 1-Me-3-Hexynyl | —C≡C— |
| 112a/b | 5,5-diMeDox | H | H | 1-Me-3-Hexynyl | —C≡C— |
| 113a/b | COOH | H | H | cPn | —CH=CH— |
| 114a/b | COOMe | H | H | cPn | —CH=CH— |
| 115a/b | COOH | H | H | cPn | —CH₂CH₂— |
| 116a/b | COOH | H | H | cPn | —C≡C— |
| 117a/b | COOH | H | Et | cPn | —CH=CH— |
| 118a/b | COOH | Me | Me | cPn | —CH=CH— |
| 119a/b | CH₂OH | H | H | cPn | —CH=CH— |
| 120a/b | COCH₂OH | H | H | cPn | —CH=CH |
| 121a/b | COOH | H | H | 3-MecPn | —CH=CH |
| 122a/b | COOH | H | H | cHx | —CH=CH |
| 123a/b | COOH | H | H | cHx | —CH₂CH₂— |
| 124a/b | COOH | H | H | cHx | —C≡C— |
| 125a/b | CH₂OH | H | H | cHx | —CH=CH— |
| 126a/b | COCH₂OH | H | H | cHx | —CH=CH— |
| 127a/b | CHO | H | H | cHx | —CH=CH— |
| 128a/b | COOH | H | H | 4-MecHx | —CH=CH— |
| 129a/b | CH₂OH | H | H | 4-MecHx | —CH=CH— |
| 130a/b | COOH | H | H | 3-PrcHx | —CH=CH— |
| 131a/b | COOH | H | Me | 3-PrcHx | —CH=CH— |
| 132a/b | COOMe | H | H | 3-PrcHx | —CH=CH— |
| 133a/b | —CH(OMe)₂ | H | H | 3-PrcHx | —CH=CH— |
| 134a/b | COOH | H | H | —CH₂cPn | —CH=CH— |
| 135a/b | COOH | H | Me | —CH₂cPn | —CH=CH— |
| 136a/b | COOMe | H | H | —CH₂cPn | —CH=CH— |
| 137a/b | COOH | H | H | —CH₂cHx | —CH=CH— |
| 138a/b | COOH | H | H | 2-PhEt | —CH=CH— |
| 139a/b | COOH | H | H | 2-PhEt | —C≡C— |
| 140a/b | CH₂OH | H | H | 2-PhEt | —CH=CH— |
| 141a/b | COOH | H | H | 2-m-ClPhEt | —CH=CH— |
| 142a/b | COOH | H | H | —CH₂OPh | —CH=CH— |
| 143a/b | COOH | H | H | —CH₂OPh | —C≡C— |
| 144a/b | COOH | Me | Me | —CH₂OPh | —CH=CH— |
| 145a/b | COOMe | H | H | —CH₂OPh | —CH=CH— |
| 146a/b | COOH | H | H | —CH₂O(p-FPh) | —CH=CH— |
| 147a/b | COOH | H | H | —CH₂O(m-ClPh) | —CH=CH— |
| 148a/b | COOH | H | H | —CH₂O(m-MeOPh) | —CH=CH— |
| 149a/b | COOH | H | H | —CH₂O(m-CF₃Ph) | —CH=CH— |
| 150a/b | COOH | H | H | —CH₂O(m-MePh) | —CH=CH— |
| 151a/b | COOH | H | H | —CH₂SPh | —CH=CH— |

TABLE 2

| Cpd No. | R¹ | R³ | R⁷ | B |
|---|---|---|---|---|
| 152a/b | COOH | H | Bu | —CH=CH— |
| 153a/b | COOH | H | Bu | —C≡C— |
| 154a/b | COOH | H | 2-MeHP | —CH=CH— |
| 155a/b | CH₂OH | H | 2-MeHP | —CH=CH— |
| 156a/b | 5,5-diMeDox | H | 2-MeHP | —CH=CH— |
| 157a/b | COOH | H | 1-MePn | —CH=CH— |
| 158a/b | COOMe | H | 1-MePn | —CH=CH— |
| 159a/b | CH₂OH | H | 1-MePn | —CH=CH— |
| 160a/b | 5,5-diMeDox | H | 1-MePn | —CH=CH— |
| 161a/b | COOH | H | 1,1-diMePn | —CH=CH— |
| 162a/b | CH₂OH | H | 1,1-diMePn | —CH=CH— |
| 163a/b | CH₂OH | H | 1-Me—4-Pentenyl | —CH=CH— |
| 164a/b | —COOH | H | 1-Me—5-Hexenyl | —CH=CH— |
| 165a/b | —CH₂OH | H | 1-Me—5-Hexenyl | —CH=CH— |
| 166a/b | COOH | H | 1,1-diMe—5-Hexenyl | —CH=CH— |
| 167a/b | CH₂OH | H | 1,1-diMe—5-Hexenyl | —CH=CH— |
| 168a/b | 5,5-diMeDox | H | 1,1-diMe—5-Hexenyl | —CH=CH— |
| 169a/b | COOH | H | 2,6-diMe—5-Heptenyl | —CH=CH— |
| 170a/b | COOH | H | 2,6-diMe—5-Heptenyl | —C≡C— |
| 171a/b | COOH | Me | 2,6-diMe—5-Heptenyl | —CH=CH— |
| 172a/b | COOMe | H | 2,6-diMe—5-Heptenyl | —CH=CH— |
| 173a/b | CH₂OH | H | 2,6-diMe—5-Heptenyl | —CH=CH— |
| 174a/b | 5,5-diMeDox | H | 2,6-diMe—5-Heptenyl | —CH=CH— |
| 175a/b | COOH | H | cPn | —CH=CH— |
| 176a/b | CH₂OH | H | cPn | —CH=CH— |
| 177a/b | COOH | H | cHx | —CH=CH— |
| 178a/b | CH₂OH | H | cHx | —CH=CH— |
| 179a/b | 5,5-diMeDox | H | cHx | —CH=CH— |
| 180a/b | CH₂OH | H | —CH₂cPn | —CH=CH— |
| 181a/b | CH₂OH | H | —CH₂cHx | —CH=CH— |
| 182a/b | CH₂OH | H | —CH₂OPh | —CH=CH— |

TABLE 3

| Cpd No. | R¹ | R² | R³ | R⁷ | B |
|---|---|---|---|---|---|
| 183a/b | COOH | H | H | Pn | —CH=CH— |
| 184a/b | COOH | H | H | Pn | —C≡C— |
| 185a/b | CH₂OH | H | H | 1-MePn | —CH=CH— |
| 186a/b | CH₂OH | H | Me | 2-Me—5-Hexenyl | —CH=CH— |
| 187a/b | 5,5-diMeDox | H | H | 2-Me—5-Hexenyl | —CH=CH— |
| 188a/b | COOH | H | H | 2,6-diMe—5-Heptenyl | —CH=CH— |

TABLE 3-continued

| Cpd No. | R¹ | R² | R³ | R⁷ | B |
|---|---|---|---|---|---|
| 189a/b | COOH | Me | Me | 2,6-diMe—5-Heptenyl | —CH=CH— |
| 190a/b | COOH | H | H | 2,6-diMe—5-Heptenyl | —C≡C— |
| 191a/b | COOH | H | H | 2,6-diMe—5-Heptenyl | —CH₂CH₂— |
| 192a/b | COOMe | H | H | 2,6-diMe—5-Heptenyl | —CH=CH— |
| 193a/b | CH₂OH | H | H | 2,6-diMe—5-Heptenyl | —CH=CH— |
| 194a/b | COOH | H | H | cHx | —CH=CH— |
| 195a/b | CH₂OH | H | H | cHx | —CH=CH— |
| 196a/b | COOH | H | H | —CH₂cPn | —CH=CH— |

TABLE 4

| Cpd No. | R² | R³ | R⁴ | R⁵ | R⁷ | B |
|---|---|---|---|---|---|---|
| 197a/b | H | H | 2-THP | 2-THP | Pn | —CH=CH— |
| 198a/b | H | Me | 2-THP | 2-THP | Pn | —CH=CH— |
| 199a/b | H | H | diMe—tBuSi | diMe—tBuSi | Pn | —CH=CH— |
| 200a/b | H | H | 2-THP | 2-THP | 1-MePn | —CH=CH— |
| 201a/b | H | H | diPh-tBuSi | diPh-tBuSi | 1-MePn | —CH=CH— |
| 202a/b | H | H | 2-THP | 2-THP | 1-MePn | —C≡C— |
| 203a/b | H | H | 2-THP | 2-THP | 1-Me—5-Hexenyl | —CH=CH— |
| 204a/b | H | H | COMe | COMe | 1-Me—5-Hexenyl | —CH=CH— |
| 205a/b | H | H | 2-THP | 2-THP | 1,1-diMe—5-Hexenyl | —CH=CH— |
| 206a/b | H | H | 2-THF | 2-THF | 1,1-diMe—5-Hexenyl | —CH=CH— |
| 207a/b | H | H | 2-THP | 2-THP | 2,6-diMe—5-Heptenyl | —CH=CH— |
| 208a/b | H | H | H | H | 2,6-diMe—5-Heptenyl | —CH=CH— |
| 209a/b | H | H | 2-THP | 2-THP | 2,6-diMe—5-Heptenyl | —CH₂CH₂— |
| 210a/b | Me | Me | 2-THP | 2-THP | 2,6-diMe—5-Heptenyl | —CH=CH— |
| 211a/b | H | H | 2-THP | 2-THP | 1-Me—3-Pentynyl | —CH=CH— |
| 212a/b | H | H | 2-THP | 2-THP | 1-Me—3-Hexynyl | —CH=CH— |
| 213a/b | H | H | 2-THP | 2-THP | 1-Me—3-Hexynyl | —C≡C— |
| 214a/b | H | H | 2-THP | 2-THP | —CH₂cPn | —CH=CH— |
| 215a/b | H | H | 2-THP | 2-THP | cHx | —CH=CH— |
| 216a/b | H | H | 2-THP | 2-THP | —CH₂OPh | —CH=CH— |
| 217a/b | H | H | 2-THP | 2-THP | 2-PhEt | —CH=CH— |

In the case of the compounds listed above in Tables 1–3 where R¹ represents a carboxy group, the sodium and potassium salts are also preferred.

Of the compounds listed above, most preferred are Compounds No. 3a, 15a, 23a, 25a, 53a, 67a, 98b, 113b, 122a, 122b and 142b, particularly the following isomers:

3a. 3-(1,1-methylene-4-carboxybutyl)-6β-(3α-hydroxy-1-octenyl)-7α-hydroxybicyclo[3.3.0]oct-2-ene 15a. 3-(1,1-methylene-4-carboxybutyl)-6β-(3α-hydroxy-4-methyl-1-octenyl)-7α-hydroxybicyclo[3.3.0]oct-2-ene 23a. 3-(1,1-methylene-4-carboxybutyl)-6β-(3α-hydroxy-5-methyl-1-nonenyl)-7α-hydroxybicyclo[3.3.0]oct-2-ene 25a. 3-(1,1-methylene-4-carboxybutyl)-6β-(3α-hydroxy-4,4-dimethyl-1-octenyl)-7α-hydroxybicyclo[3.3.0]oct-2-ene 53a. 3-(1,1-methylene-4-carboxybutyl)-6β-(3α-hydroxy-4,4-dimethyl-1,8-nonadienyl)-7α-hydroxybicyclo[3.3.0]oct-2-ene 67a. 3-(1,1-methylene-4-carboxybutyl)-6β-(3α-hydroxy-5,9-dimethyl-1,8-decadienyl)-7α-hydroxybicyclo[3.3.0]oct-2-ene 98b. 3-(1,1-methylene-2-carboxymethoxyethyl)-6β-(3α-hydroxy-4-methyloct-1-en-6-ynyl)-7α-hydroxybicyclo[3.3.0]oct-2-ene 113b. 3-(1,1-methylene-2-carboxymethoxyethyl)-6β-(3α-hydroxy-3-cyclopentyl-1-propenyl)-7α-hydroxybicyclo[3.3.0]oct-2-ene 122a. 3-(1,1-methylene-4-carboxybutyl)-6β-(3α-hydroxy-3-cyclohexyl-1-propenyl)-7α-hydroxybicyclo[3.3.0]oct-2-ene 122b. 3-(1,1-methylene-2-carboxymethoxyethyl)-6β-(3α-hydroxy-3-cyclohexyl-1-propenyl)-7α-hydroxybicyclo[3.3.0]oct-2-ene 142b. 3-(1,1-methylene-2-carboxymethoxyethyl)-6β-(3α-hydroxy-4-phenoxy-1-butenyl)-7α-hydroxybicyclo[3.3.0]oct-2-ene and pharmaceutically acceptable salts and esters thereof, especially the sodium and potassium.

The compounds of the invention may be prepared as illustrated by the following reaction schemes:

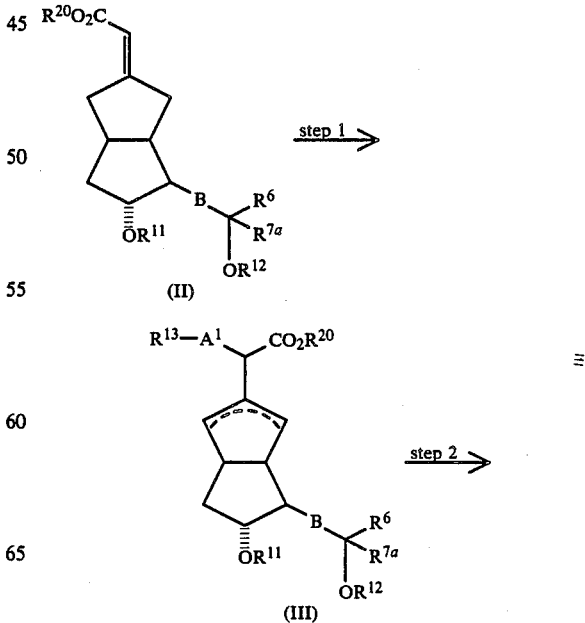

-continued
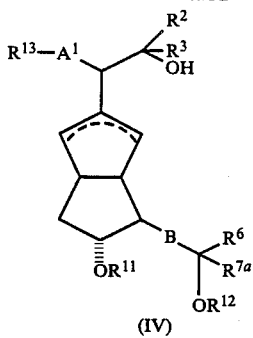
(IV)
step 3 →
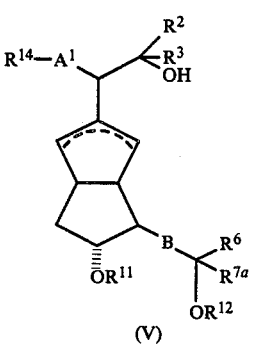
(V)
step 4 →
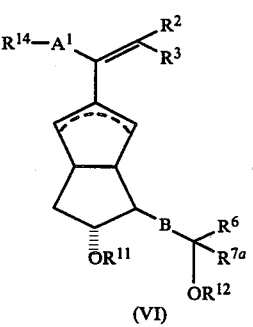
(VI)
step 5 →
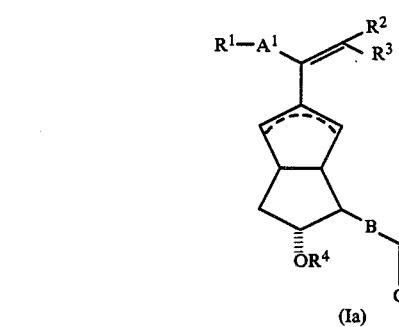
(VI')
step 6 →
-continued
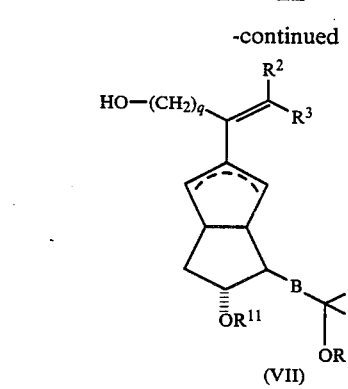
(VII)
step 7 →
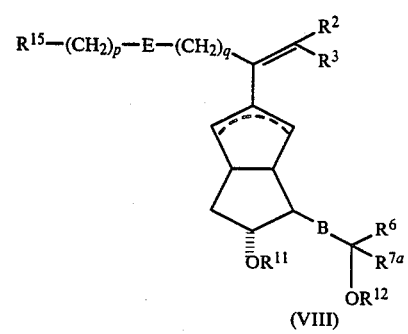
(VIII)
step 8 →
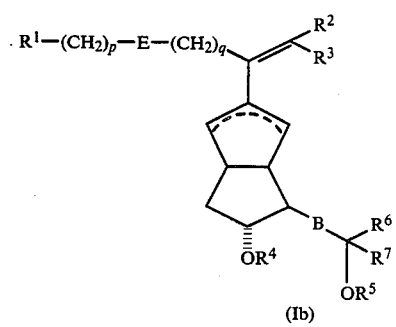
(Ib)
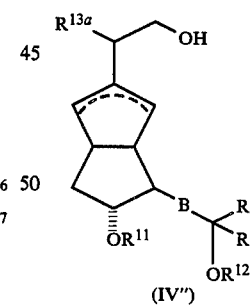
(Ia)
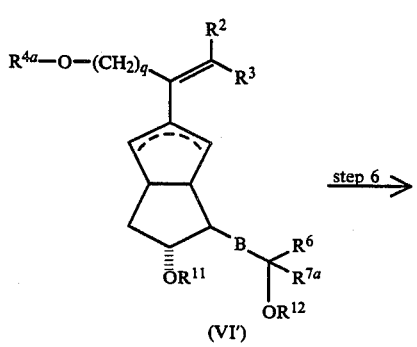
(IV″)
step 9 →
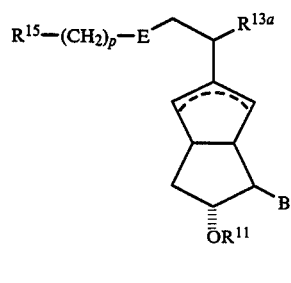
(IX)
step 10 →

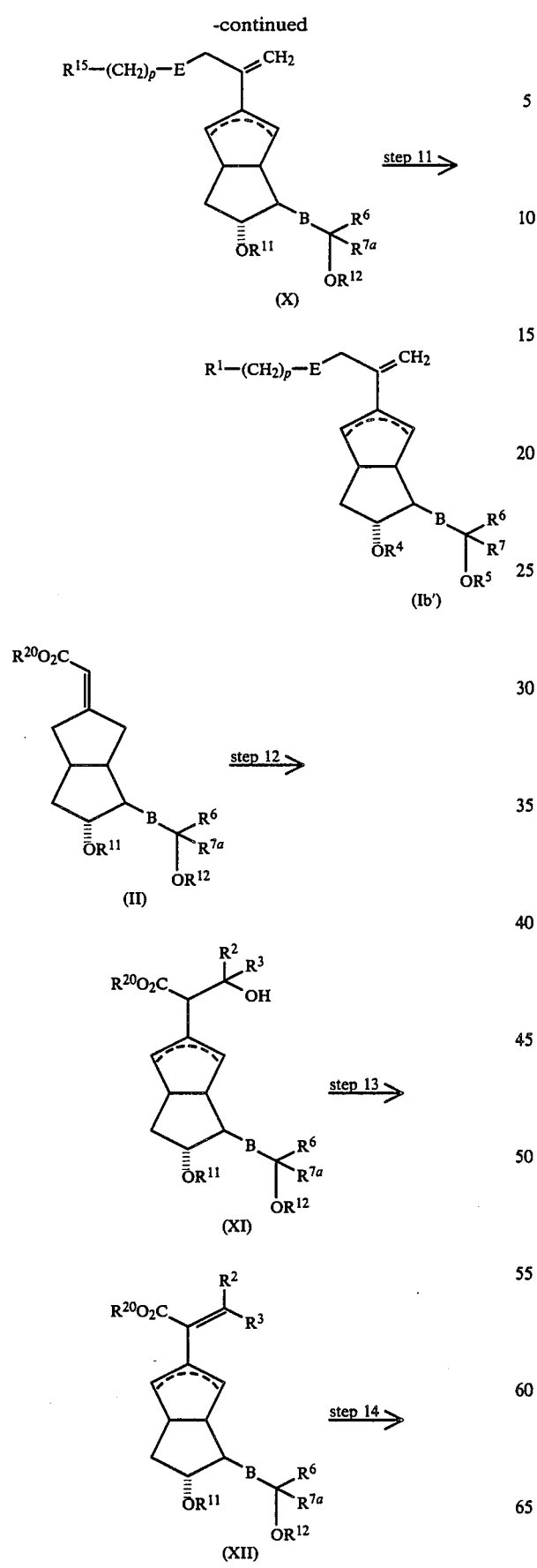
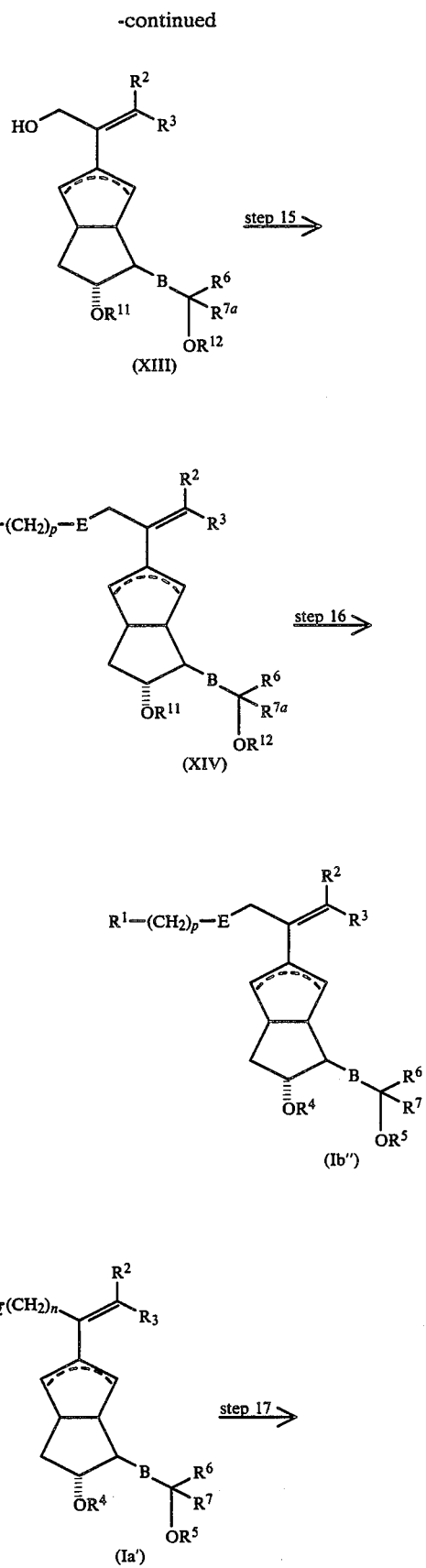

-continued

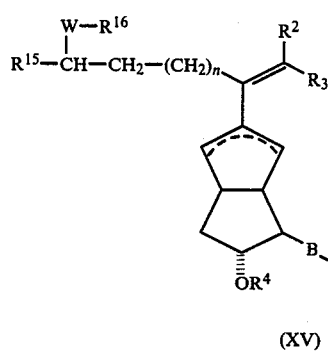
(XV)

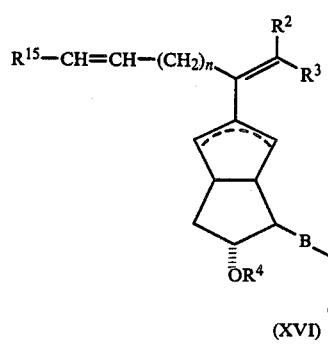
(XVI)

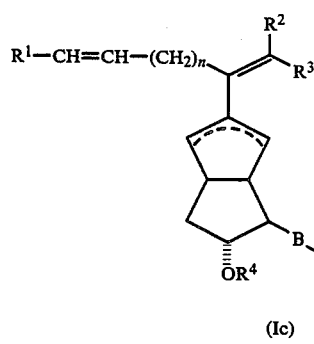
(Ic)

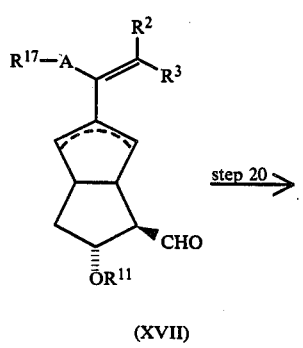
(XVII)

-continued

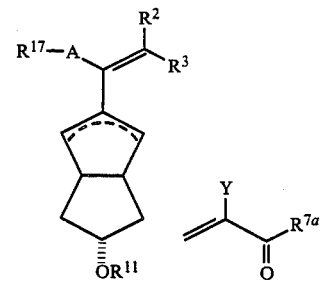
(XVIII)

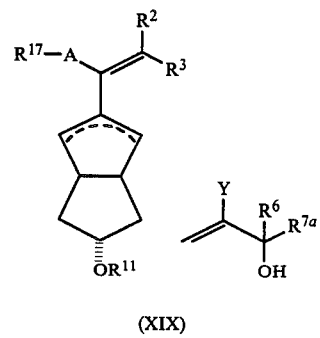
(XIX)

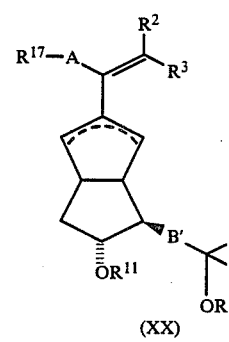
(XX)

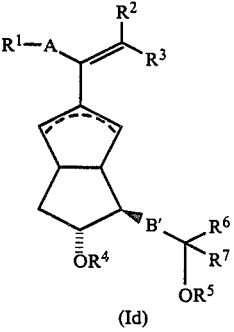
(Id)

In the above formulae, $R^1$, $R^2$, $R^3$, $R^4$, $R^5$, $R^6$, $R^7$, B, E, n, p, q and the dotted line are as defined above. In addition:

$R^{4a}$ represents a hydroxy-protecting group, for example any of the groups defined as $R^{10}$ above;

$R^{7a}$ can represent any of the groups or atoms represented by $R^7$, provided that any hydroxy or acyl group present in the group represented by $R^7$ should be protected;

$R^{11}$ and $R^{12}$ are the same or different and each represents a hydroxy-protecting group;

R[13] represents a hydroxymethyl group which is protected by a heterocyclic group, a substituted methyl group, an aralkyl group, a trisubstituted silyl group or a tetrazolyl group;

R[13a] represents a hydroxymethyl group which is protected by a heterocyclic group, a substituted methyl group, an aralkyl group or a trisubstituted silyl group;

R[14] represents a protected hydroxymethyl group or a tetrazolyl group;

R[15] represents a carboxy group, a protected carboxy group or a tetrazolyl group;

R[16] represents a $C_1$-$C_4$ alkyl group or an aryl group;

R[17] represents a carboxy group, a protected carboxy group, a hydroxymethyl group, a protected hydroxymethyl group, a formyl group, a formyl group which is protected by conversion to another group as defined above or a tetrazolyl group;

R[20] represents a hydrogen atom or a carboxy-protecting group;

A' represents a single bond, a straight chain $C_1$-$C_7$ alkylene group or a fluorinated straight chain $C_1$-$C_7$ alkylene group;

B' represents a vinylene group or an ethynylene group; and

W represents a sulfur atom or a selenium atom.

METHOD A

This comprises Steps 1-5 and prepares a compound of formula (Ia) in which A in the general formula (I) represents a single bond, an alkylene group or fluorinated alkylene group.

Step 1

In this step, the compound of formula (II) is treated with a base in an inert solvent to generate a carbanion and this carbanion is then reacted with a compound of formula (XXI):

X—A'—R[13]     (XXI)

(in which R[13] and A' are as defined above and X represents a halogen atom, for example a chlorine, bromine or iodine atom).

The compound of formula (II), which is the starting material for this step is a known compound which can readily be prepared by known means, for example as described in European Patent Publication No. 136779.

Suitable bases are aminolithium compounds in which the amino group is substituted by two $C_1$-$C_4$ alkyl and/or $C_5$-$C_7$ cycloalkyl groups, for example diethylaminolithium, diisobutylaminolithium, isobutylcyclohexylaminolithium or dicyclohexylaminolithium, the dialkylaminolithium compounds being preferred. Where R[20] represents a hydrogen atom, the base is preferably employed in an amount of more than 2 equivalents per equivalent of the compound of formula (II).

There is no particular restriction upon the nature of the solvent employed for this reaction, provided that it has no adverse effect upon the reaction. Suitable solvents include, for example: ethers, such as diethyl ether or tetrahydrofuran; a phosphoric acid amide, such as hexamethylphosphoric triamide; or a mixture of two or more of these solvents.

The reaction to generate the carbanion is preferably carried out at a relatively low temperature, for example from $-100°$ C. to $-20°$ C. and will normally require a reaction time of from 5 to 30 minutes. Reaction of the carbanion with the halogen compound of formula (XXI) is also preferably effected at a relatively low temperature, e.g. from $-80°$ C. to room temperature; a period of from 15 minutes to 5 hours will normally suffice for this reaction.

Step 2

In this step, the compound of formula (III) is converted to an alcohol compound of formula (IV) by treating the compound of formula (III) in an inert solvent with a reducing agent and/or a Grignard reagent or an alkyllithium. Examples of Grignard reagents and alkyllithium compounds are those compounds having the formulae:

R[2a]—Mg—X     (XXII)

R[2a]—Li     (XXII')

XMg—(CH$_2$)$_r$MgX     (XXIII)

(in which X is as defined above; R[2a] represents a $C_1$-$C_4$ alkyl group; and r is an integer from 2 to 6).

A compound of formula (IV) in which R[2] and R[3] both represent hydrogen atoms is obtained by treating the compound of formula (III) with a reducing agent. A compound (IV) in which one of R[2] and R[3] is a $C_1$-$C_4$ alkyl gorup and the other is a hydrogen atom is obtained by reacting the compound (III) with approximately an equimolar amount of the compound (XXII) or (XXII') to give a ketone and then reacting the ketone compound thus obtained with a reducing agent (either in situ or after isolating the ketone intermediate); where R[20] represents a hydrogen atom, we prefer that the compound (III) should be reacted with the alkyllithium (XXII'). A compound (IV) in which R[2] and R[3] are the same or different and each represents a $C_1$-$C_4$ alkyl group is obtained by reacting the compound (III) with the Grignard reagent (XXII) or the alkyllithium (XXII') to give the ketone and then reacting the ketone with the Grignard reagent (XXII) or the alkyllithium (XXII'). A compound (IV) in which R[2] and R[3] both represent the same $C_1$-$C_4$ alkyl group may be obtained by treating the compound (III) with more than two equivalents of the Grignard reagent (XXII) or the alkyllithium (XXII'). A compound (IV) in which R[2] and R[3], together with the carbon atom to which they are attached, form a $C_3$-$C_7$ cycloalkyl group may be obtained by treating the compound (III) with the Grignard reagent (XXIII).

There is no particular restriction on the nature of the reducing agent to be employed, provided that it is capable of converting a carboxy or alkoxycarbonyl group into a hydroxymethyl group. We prefer to employ a metal hydride or borohydride, for example lithium aluminum hydride, lithium borohydride, diisobutylaluminum hydride or diborane.

The reaction is carried out in the presence of an inert solvent, the nature of which is not critical, provided that it has no adverse effect upon the reaction. We prefer to employ an ether, for example diethyl ether, tetrahydrofuran or dioxane.

The reactions will take place over a wide range of temperatures, for example from $-20°$ C. to room temperature and a period of from 30 minutes to 5 hours will normally suffice for the reaction.

After completion of the reaction, the reaction product can be recovered from the reaction mixture by conventional means. For example, one suitable recovery procedure comprises: pouring the reaction mixture into water; if necessary, neutralizing the mixture, extracting the mixture with a water-immiscible organic solvent; and then evaporating the solvent from the extract to give the desired product. This may, if required, be further purified by such conventional techniques as recrystallization or the various chromatography techniques, such as column chromatography.

Step 3

In this step, if required, the protecting group in the protected hydroxymethyl group represented by $R^{13}$ is converted into another protecting group. This may be achieved by the following sequence of reactions:

(a) protecting the hydroxy group attached to the carbon atom to which $R^2$ and $R^3$ are also attached;

(b) eliminating the protecting group from the group represented by $R^{13}$;

(c) protecting the hydroxy group generated by the reaction in Step (b) with the desired protecting group, to give the protected hydroxymethyl or tetrazolyl group $R^{14}$; and (d) eliminating the protecting group from the hydroxy group attached to the carbon atom to which $R^2$ and $R^3$ are also attached.

In order that this sequence of reactions should proceed smoothly, it is necessary to select the various protecting groups having regard to conditions under which they are to be eliminated.

When the protecting group in $R^{13}$ is an aralkyl group, then the protecting group employed in reaction (a) is a heterocyclic group, a substituted methyl group or a trisubstituted silyl gorup (preferably a dimethyl-t-butylsilyl group or a diphenyl-t-butylsilyl group, more preferably a diphenyl-t-butylsilyl group). After completion of the protection reaction (a) elimination of the aralkyl protecting group in reaction (b) may be achieved by reduction; and then the protecting reaction (c) is effected with the desired protecting group on the hydroxy group thus generated. In this reaction (c) when the protecting group employed in reaction (a) is a group that can be eliminated under acidic conditions (for example a heterocyclic group or a substituted methyl group), a desirable protecting group is an acyl group, a dimethyl-t-butylsilyl group or a diphenyl-t-butylsilyl group; when the protecting group employed in reaction (a) is a group that can be eliminated under acidic, neutral or basic conditions (such as a trisubstituted silyl group), a desirable protecting group for reaction (c) is an acyl group, a heterocyclic group or a substituted methyl group.

Where the protecting group in $R^{13}$ is a trisubstituted silyl group, then the protecting group employed in reaction (a) is preferably an acyl group, a heterocyclic group, a substituted methyl group or an aralkyl group; after completion of the protecting reaction (a), the elimination reaction (b) to eliminate this trisubstituted silyl group is then performed appropriately under acidic, neutral or basic conditions; finally, the protecting reaction (c) is carried out with the desired protecting group to protect the hydroxy group so generated. In this reactioon (c), when the protecting group employed in reaction (a) is a group that can be eliminated under basic conditions (for example an acyl group), a desirable protecting group is a heterocyclic group, a substituted methyl group or an aralkyl group. When the protecting group employed in reaction (a) is a group that can be eliminated under acidic conditions (such as a heterocyclic group or a substituted methyl group), a desirable protecting group for reaction (c) is an acyl group or an aralkyl group. When the protecting group employed in reaction (a) is a group that can be eliminated under reducing conditions (such as an aralkyl group), a desirable protecting group for reaction (c) is an acyl group, a heterocyclic group or a substituted methyl group.

The protecting reactions and elimination reactions involved in this step may be carried in the same way as described in Step 22 (Method D) or in Step 5 (Method A) hereafter.

When $R^{11}$, $R^{12}$ and/or the hydroxy-protecting group or acyl-protecting group in the group $R^{7a}$ is eliminated by the elimination reaction (b) or (d), the group may be appropriately protected after this step.

Step 4

In this step, the hydroxy group of the compound of formula (V) is first sulfonylated or replaced by a halogen atom, and then the resulting compound is treated with a base to cause dehydrohalogenation or dehydrosulfonylation and give the unsaturated compound of formula (VI).

Sulfonylation may be carried out by reacting the compound of formula (V) with a sulfonyl halide in an inert solvent and in the presence of a base. Suitable sulfonyl halides include, for example: $C_1$-$C_4$ alkanesulfonyl halides, such as methanesulfonyl halide or ethanesulfonyl halide; and arylsulfonyl halides, such as benzenesulfonyl chloride or p-toluenesulfonyl chloride; however, methanesulfonyl chloride is preferred. Suitable bases include organic amines, such as triethylamine, ethyldiisopropylamine, pyridine or N,N-diethylaniline.

Replacement of the hydroxy group by a halogen atom can be carried out by treating the compound of formula (V) with a sulfur or phosphorus halide compound, such as thionyl chloride or phosphorus tribromide, or with a combination of a phosphine with a carbon tetrahalide. Suitable phosphines include, for example: trialkylphosphines, such as trimethylphosphine or tributylphosphine; and triarylphosphines, such as triphenylphosphine or tritolylphosphine; however, the triarylphosphines are preferred. Suitable carbon tetrahalides include carbon tetrachloride, carbon tetrabromide or carbon tetraiodide, of which carbon tetrachloride or carbon tetrabromide are preferred.

There is no particular restriction upon the nature of the inert solvent employed for either of the above reactions, provided that it has no adverse effect upon the reaction. Suitable solvents include, for example: hydrocarbons, which may be aliphatic, cycloaliphatic or aromatic, such as hexane, cyclohexane, benzene, toluene or xylene; halogenated hydrocarbons, especially halogenated aliphatic hydrocarbons, such as methylene chloride, chloroform or 1,2-dichloroethane; ethers, such as diethyl ether, tetrahydrofuran, ethylene glycol dimethyl ether or dioxane; and ketones, such as acetone or methyl ethyl ketone. We prefer to use a halogenated hydrocarbon for the sulfonylation reaction or an ether for the reaction with a carbon tetrahalide.

The reactions will take place over a wide range of temperatures, for example from $-30°$ C. to $+50°$ C. The time required for the reaction may vary widely, depending upon many factors, notably the reaction and the nature of the reagents; however, a period of from 10 minutes to 10 hours will normally suffice.

Subsequently, the sulfonylated or halogenated compound is reacted with a base in the presence or absence of an inert solvent.

Suitable bases include, for example: tertiary amines, such as triethylamine, ethyldiisopropylamine, N,N-dimethylaniline, 4-(N,N-dimethylamino)pryidine, 1,5-diazobicyclo[4.3.0]non-5-ene or 1,8-diazobicyclo[5.4.0]undec-7-ene; alkali metal hydroxides, such as lithium hydroxide, sodium hydroxide or potassium hydroxide; alkali metal carbonates, such as sodium carbonate or potassium carbonate and alkali metal alkoxides, such as sodium methoxide, sodium ethoxide, potassium ethoxide, sodium t-butoxide, potassium t-butoxide or sodium t-pentoxide; however, a tertiary amine is preferred.

There is no particular restriction on the nature of the solvent employed, provided that it has no adverse effect upon the reaction. Suitable solvents include, for example: alcohols, such as methanol, ethanol, propanol or t-butanol; hydrocarbons, such as hexane, cyclohexane, benzene, toluene or xylene; ethers, such as diethyl ether, tetrahydrofuran, dioxane or ethylene glycol dimethyl ether; and phosphoric acid amides, such as hexamethylphosphoric triamide. We prefer to use either an ether or a phosphoric acid triamide. If desired, where a tertiary amine is employed as the base, an excess of this can be used as the reaction solvent.

The reaction can be helped to proceed more smoothly by the addition of an alkali metal halide, such as sodium iodide.

The reaction will take place over a wide of temperatures and the particular reaction temperature chosen is not critical to the invention. In general, we find it convenient to carry out the reaction at a temperature in the range from 0° to 80° C. The time required for the reaction may vary widely, depending upon many factors, notably the reaction temperature and the nature of the reagents; however, a period of from 10 minutes to 5 hours will normally suffice.

After completion of the reaction, the desired product can be recovered from the reaction medium by conventional means. For example, one suitable recovery procedure comprises: pouring the reaction mixture into ice-water; if necessary, neutralizing the mixture; extracting the mixture with a water-immiscible organic solvent; and then removing the solvent, for example by evaporation under reduced pressure, to give the desired compound. If necessary, the product can be further purified by such conventional techniques as recrystallization or the various chromatography techniques, for example column chromatography.

Step 5

This step comprises any one or more of a number of optional reactions, although, of course, it may be that the compound of formula (VI) obtained in step 4 is the desired final product, in which case step 5 may be omitted altogether. The reactions involved in this step are: removal of the hydroxy-protecting group of $R^{14}$; conversion of the hydroxymethyl group represented by or included within the group represented by $R^1$ to a formyl group (involving protecting formyl group) or to a carboxy group; esterification of the carboxy group; conversion of the carboxy group or an esterified carboxy group to the corresponding amide; elimination or $R^{11}$, $R^{12}$ and/or any hydroxy-protecting group in $R^{7a}$; elimination of any acyl-protecting group in $R^{7a}$; and conversion of the carboxy group to a hydroxymethylcarbonyl group (involving protection of hydroxy groups). These reactions may be carried out in any appropriate order.

When the hydroxy-protecting group is a $C_1$-$C_6$ aliphatic or aromatic acyl group, it may be removed by a conventional hydrolysis reaction, employing an acid or a base. The acid or base employed may be any one of those conventionally used for hydrolysis reactions of this type. However, we normally prefer to carry out the hydrolysis under basic conditions, using as the base a hydroxide of an alkali metal or of an alkaline earth metal, such as lithium hydroxide, sodium hydroxide, potassium hydroxide, calcium hydroxide or barium hydroxide. The reaction is normally carried out in a solvent, and any solvent commonly used for hydrolysis reactions may be employed, although, once again, the choice is not particularly critical. Examples of suitable solvents include: alcohols, such as methanol, ethanol, propanol or isopropanol; ethers, such as diethyl ether, tetrahydrofuran, dioxane or ethylene glycol dimethyl ether; or a mixture of one or more or these organic solvents with water.

There is no particular limitation on the reaction temperature, which may, accordingly, vary over a wide range. For convenience, the reaction is normally carried out at about room temperature or at the reflux temperature of the solvent employed or at a temperature between these. The time required for the reaction, although varying depending upon the reaction temperature and other reaction conditions, is usually from 1 to 12 hours.

Where the hydroxy-protecting group is an aralkyl group, it may be removed by contacting the compound of formula (VI) with a reducing agent in an inert solvent.

Reducing agents employed for this type of reaction are well-known and examples include: alkali metals, such as lithium, sodium or potassium; and alkali metal sulfides, such as sodium sulfide or potassium sulfide; alkali metals are preferred. Where an alkali metal is used, the solvent is preferably liquid ammonia or a mixture of liquid ammonia with an ether such as diethyl ether or tetrahydrofuran. Where the reducing agent is an alkali metal sulfide, the solvent is preferably an alcohol (such as methanol or ethanol), an ether (such as tetrahydrofuran or dioxane) or a mixture of one or more of these with water.

The reaction temperature is preferably from −78° C. to −20° C. when an alkali metal is used or from 0° C. to 100° C. when an alkali metal sulfide is used. Although the time required for the reaction will vary depending upon the reagents and reaction conditions (including the reaction temperature), a period of from 20 minutes to 6 hours will normally suffice.

When the hydroxy-protecting group is a p-methoxybenzyl group, it may also be removed by treatment with ammonium cerium nitrate in aqueous acetone at about room temperature or by treatment with an oxidizing agent, such as dichlorodicyanoquinone or sodium persulfate.

When the hydroxy-protecting group is a heterocyclic group, a substituted methyl group (such as an alkoxymethyl group or an aralkoxymethyl group) a 1-alkoxyethyl group or a trityl group, it can easily be removed by contacting the compound with an acid. Suitable acids include organic acids (such as formic acid, acetic acid, trifluoroacetic acid, propionic acid, butyric acid, oxalic acid, malonic acid, methanesulfonic acid, benzenesulfonic acid, p-toluenesulfonic acid or camphorsulfonic acid) or a mineral acid (such as hydrochloric acid, hydrobromic acid or sulfuric acid). Although this reaction may be carried out in the presence or absence of a solvent, the use of a solvent is preferred, in order to ensure that the reaction proceeds smoothly. The nature of the solvent is not critical, provided that it has no adverse effect upon the reaction. Examples of suitable solvents include: water; alcohols, such as methanol or ethanol; ethers, such as tetrahydrofuran or dioxane; ketones, such as acetone or methyl ethyl ketone; and mixtures of one or more of the aforementioned organic solvents with water. The reaction temperature is not particularly critical and, for convenience, the reaction is normally carried out at a temperature ranging from room temperature to the reflux temperature of the reaction mixture. The time required for the reaction will vary, depending upon the nature of the reagents, the reaction temperature and other reaction conditions, but a period of from 30 minutes to 10 hours will normally suffice.

Where the protecting group is a methylthiomethyl group, it can be eliminated by treatment with mercuric chloride in aqueous acetonitrile, but otherwise under the same conditions as used for the other substituted methyl groups above. In the course of this reaction, where $R^{7a}$ is one of the protected formyl groups defined above, these protecting groups may also be eliminated.

Where the hydroxy-protecting group is a tri-($C_1$–$C_6$ alkyl)silyl group or a diaryl($C_1$–$C_6$ alkyl)silyl group, this may easily be removed by contacting the compound with water or with an acid or a base in the presence of water. Suitable acids and bases include: organic acids, such as formic acid, acetic acid, propionic acid, butyric acid, oxalic acid or malonic acid; mineral acids, such as hydrochloric acid, hydrobromic acid or sulfuric acid; alkali metal or alkaline earth metal hydroxides, such as potassium hydroxide or calcium hydroxide; and alkali metal or alkaline earth metal carbonates, such as potassium carbonate or calcium carbonate. If water is used with the acid or base, there is no need for any other solvent. However, if another solvent is desired, the choice is not critical, provided that the solvent does not interfere with the reaction; suitable other solvents include: ethers, such as tetrahydrofuran or dioxane; and alcohols, such as methanol or ethanol; these are, in any case, preferably employed in admixture with water.

There is no particular limitation on the reaction temperature and, for convenience, the reaction is normally carried out at about room temperature. The time required for the reaction will vary, depending upon the reagents, the reaction temperature and other reaction conditions, but is usually from 30 minutes to 5 hours.

When the hydroxy-protecting group is t-butyldiphenylsilyl or t-butyldimethylsilyl group, this may also be removed by treatment with a compound generating a fluoride anion, e.g. tetrabutylammonium fluoride, in the presence of an ether (such as tetrahydrofuran or dioxane) under similar reaction conditions.

After completion of the reaction, the desired product may be recovered from the reaction mixture by conventional means. For example, the compound may be obtained simply by distilling off the solvent under reduced pressure. Alternatively, it may be obtained by the following technique: pouring the reaction mixture, without distillation, into ice-water; if necessary, neutralizing the mixture; extracting the mixture with an appropriate organic solvent; washing and then drying the extract; and finally removing the solvent from the extract by distillation.

Where the hydroxy-protecting groups represented by or included within the groups represented by $R^{11}$, $R^{12}$ and $R^{7a}$ are identical, they will be removed simultaneously by these reactions. Also, of course, it will be appreciated that, by appropriate selection of the protecting groups, they may be removed selectively.

Conversion of the hydroxymethyl group represented by or included within the group represented by $R^1$ in the resulting compound of formula (I) to a formyl group may be carried out by employing a conventional reaction for the oxidization of a primary alcohol to an aldehyde. When carrying out this reaction, it is necessary that the hydroxy-protecting groups represented by $R^{11}$ and $R^{12}$ and in $R^{7a}$ should not have been removed; in other words, the hydroxy groups at the 3-position of the side chain on the cyclopentane ring and at the 7-position of the bicyclooctane system should both be protected. If they have been deprotected in the course of the above reactions, then they should be re-protected.

The reaction is carried out employing an oxidizing agent which is conventional for this type of reaction. Suitable oxidizing agents include: chromic acid compounds, such as chromic anhydride, chromic anhydride-pyridine complex (Collin's reagent), chromic anhydride-concentrated sulfuric acid-water (Jones' reagent), sodium bichromate or potassium bichromate; an organic compound containing an active halogen atom, such as N-bromoacetamide, N-bromosuccinimide, N-bromophthalimide, N-chloro-p-toluenesulfonamide or N-chlorobenzenesulfonamide; an aluminum alkoxide, such as aluminum t-butoxide or aluminum isopropoxide; dimethyl sulfoxide-dichlorocarbodiimide; or pyridine-sulfur trioxide.

The reaction is preferably carried out in the presence of an organic solvent, the nature of which is not critical, provided that it has no adverse effect upon the reaction. Suitable solvents include: halogenated hydrocarbons, such as methylene chloride, chloroform or carbon tetrachloride; ethers, such as diethyl ether, tetrahydrofuran or dioxane; ketones, such as acetone or methyl ethyl ketone; and sulfoxides, such as dimethyl sulfoxide.

The reaction is preferably carried out at a temperature of from 0° C. to ambient temperature and the time required for the reaction, although varying depending upon the reagents, reaction temperature and other reaction conditions, is generally within the range fron 30 minutes to 3 hours.

After completion of the reaction, the desired formyl compound may be isolated from the reaction mixture by conventional means. For example, one suitable recovery technique comprises: separating insoluble matter, if any, by filtration; pouring the filtrate into ice-water; if necessary, neutralizing the mixture; extracting the mixture with a water-immiscible organic solvent; if necessary, washing and drying the extract; and then removing the solvent by distillation from the extract.

If desired, this formyl group may be protected by conversion into an acetal or thioacetal by conventional means. For example, this may be achieved by reacting the formyl compound with a corresponding alcohol or thiol in an inert solvent (e.g. an ether, such as diethyl ether), in the presence of an acid (e.g. p-toluenesulfonic acid or boron trifluoride). The reaction temperature is not critical, but ambient temperature is convenient. A period of from 30 minutes to 5 hours will normally suffice for the reaction time.

This formyl group may be converted to a carboxy group by a conventional method for oxidizing an aldehyde to a carboxylic acid or the hydroxymethyl group may be directly oxidized to a carboxy group, again by conventional means. When this reaction is carried out, it is necessary that hydroxy groups represented by or included in $R^{11}$, $R^{12}$ and $R^{7a}$ should be protected.

Suitable oxidizing agents include: chromic acid compounds, such as chromic anhydride-concentrated sulfuric acid-water (Jones' reagent) or chromium trioxide; potassium permanganate complexes, such as potassium permanganate-sodium hydroxide or potassium permanganate-sodium carbonate; silver oxide; or potassium bichromate-sulfuric acid.

This reaction is normally carried out in the presence of a solvent, the nature of which is not critical, provided that it has no adverse effect upon the reaction. Suitable solvents include: ketones, such as acetone; water; mixtures of water with an alcohol, such as methanol or ethanol; or a mixture of water with pyridine.

The reaction may be carried out over a wide temperature range, for example from −30° C. to 100° C. The time required for the reaction will vary, depending upon the reagents, the reaction temperature and other reaction conditions, but is usually within the range from 30 minutes to 50 hours.

Where this reaction is carried out employing as a starting material a compound in which $R^1$ represents or includes a group representing a hydroxymethyl group, the conversion of the hydroxymethyl group to a formyl group and conversion of the formyl group to a carboxy group take place in a single reaction step.

When using Jones' reagent, selective oxidation from an alcohol to an aldehyde or to a carboxylic acid is possible by adjusting the amount of oxidizing agent and/or the reaction conditions appropriately.

After completion of the reaction, the desired carboxy compound may be isolated from the reaction mixture by conventional means. For example, one suitable recovery technique comprises: pouring the reaction mixture into ice-water; where the mixture is alkaline, acidifying it with a dilute acid; extracting the mixture with a water-immiscible organic solvent; if necessary, washing and drying the extract; and then removing the solvent from the extract by distillation.

Conversion of the carboxy group in the carboxy compound thus obtained to an esterified carboxy group may, of course, be effected using techniques well-known for the esterification of carboxylic acids. Any esterifying agent commonly used for esterification of a carboxy group may be employed, the nature of such agent depending upon the ester which it is desired to produce. Suitable esterifying agents include: diazoalkanes, such as diazomethane, diazoethane, diazopropane, diazoisopropane or diazobutane; an ester group-forming alcohol, such as methanol, ethanol, propanol, isopropanol or butanol, in admixture with a mineral acid (such as hydrochloric acid, hydrobromic acid or sulfuric acid) or an organic acid (such as methanesulfonic acid, benzenesulfonic acid or p-toluenesulfonic acid); or a $C_1$-$C_6$ alkyl halide, such as methyl bromide or ethyl bromide, in admixture with a base (such as sodium hydroxide, potassium hydroxide or sodium carbonate).

When a diazoalkane is employed, the reaction is preferably carried out in the presence of a solvent, the nature of which is not critical, provided that it does not adversely affect the reaction. The solvent employed is preferably an ether, such as diethyl ether or dioxane. Although there is no particular limitation to the reaction temperature, the reaction is preferably carried out at a relatively low temperature, in order to inhibit side reactions and to prevent decomposition of the diazoalkane; usually, the reaction is carried out at the temperature achieved by cooling with ice.

Where the esterifying agent is an alcohol in the presence of an acid, an excess of the alcohol is preferably used as the reaction solvent. There is no particular limitation on the reaction temperature and the reaction is, for convenience, normally carried out at a temperature between ambient temperature and the reflux temperature of the alcohol. The time required for the reaction will vary, depending upon the nature of the reagents (particularly the alcohol), the reaction temperature and other reaction conditions, but a period of from 1 hour to 2 days normally suffices.

An aralkyl, benzhydryl or phenacyl ester may be produced by conventional means by reacting a sodium salt of the carboxy compound with a halide corresponding to the desired ester (such as benzyl bromide, p-methoxybenzyl chloride, phenacyl bromide or benzhydryl chloride) in the presence of a base [such as triethylamine, pyridine or 4-(N,N-dimethylamino)pyridine].

A phenyl ester may be produced by treatment of a reactive derivative of the carboxy compound (such as an acid halide produced by reacting the carboxy compound with a halogenating agent, such as thionyl chloride or phosphorus pentachloride, or an acid anhydride produced by reacting the carboxy compound with an acyl halide, such as pivaloyl chloride) with an optionally substituted phenol in a suitable solvent (e.g. an ether such as diethyl ether) and in the presence of a base (such as triethylamine or 1,8-diazabicyclo[5.4.0]undec-7-ene).

For both of the above reactions, the reaction temperature is not critical, room temperature being convenient. A period of from 30 minutes to 3 hours will normally suffice for the reactions.

After completion of this reaction, the desired ester may be isolated from the reaction mixture by conventional means. For example, one suitable recovery procedure comprises: removing the solvent by distillation from the reaction mixture; if necessary, dissolving the resulting residue in an organic solvent; washing the resulting solution with an aqueous solution of an alkali, such as an alkali metal bicarbonate (e.g. sodium bicarbonate) or an alkali metal carbonate (e.g. sodium carbonate); drying the solution; and then distilling off the organic solvent.

When $R^{7a}$ is a protected formyl group of one of the above formulae in which Y represents an oxygen atom, the protecting group can be eliminated under acidic conditions, as described previously, to give a free formyl group. When Y represents a sulfur atom, the elimination may be achieved by contacting the corresponding compound with a mercuric compound, such as mercuric acetate, mercuric chloride or red mercuric oxide. The reaction is preferably effected in the presence of a solvent, the nature of which is not critical, provided that it has no adverse effect upon the reaction. Suitable solvents include, for example: ethers, such as tetrahydrofuran or diethyl ether; halogenated hydrocarbons, particularly halogenated aliphatic hydrocarbons, such as methylene chloride or chloroform; alcohols, such as methanol or ethanol; water; or a mixture of any two or more of these solvents. The reaction will be facilitated by the presene of a catalyst, particularly a Lewis acid, such as boron trifluoride or a complex thereof, e.g. with diethyl ether. The reaction will take place over a wide range of temperatures and the precise temperature chosen is not particularly critical. In general, we find it convenient to carry out the reaction at a temperature in the range from 0° to 60° C.

Conversion of the hydroxymethyl group to a hydroxymethylcarbonyl group may be effected by first converting the hydroxymethyl group to a formyl group, as described above, and then reacting this formyl group with an anion generated from a protected hydroxymethyl tin compound, to generate a 1,2-dihydroxyethyl group in which the 2-hydroxy group is protected; oxidizing the 1-hydroxy group of this 1,2-dihydroxyethyl group; and then eliminating the protecting group.

Conversion of the formyl group to a 1,2-dihydroxyethyl group in which the 2-hydroxy group is protected may be effected by reacting the formyl compound with an anion of formula (XXIV):

$(R^{16})_3Sn-{}^-CH-OR^{18}M^+$      (XXIV)

(in which $R^{16}$ is as defined above, $R^{18}$ represents a 1-alkoxyalkyl group in which the alkoxy and alkyl parts are both $C_1-C_4$, and M represents an alkali metal, such as sodium or lithium).

The compound of formula (XXIV) can be prepared in the reaction mixture by known methods, for example as described in J. Am. Chem. Soc., 100, 1481 (1978).

The reaction is preferably effected in the presence of a solvent, the nature of which is not critical, provided that it has no adverse effect upon the reaction. Suitable solvents include, for example: ethers, such as diethyl ether, tetrahydrofuran or ethylene glycol dimethyl ether; and amides, particularly phosphorus amides, such as hexamethylphosphoric triamide. The reaction will take place over a wide range of temperatures, although a relatively low temperature, e.g. from −78° C. to 0° C. is preferred. The time required for the reaction may vary widely, depending upon many factors, notably the nature of the reagents and the reaction temperature; however, a period of from 5 minutes to 2 hours will normally suffice.

Oxidation of the resulting protected 1,2-dihydroxyethyl compound to convert the 1-hydroxy group to an oxo group may be carried out by treating the compound with Collins' reagent (described above in relation to oxidation of a hydroxymethyl group to a formyl group), under the same reaction conditions. Elimination of the hydroxy-protecting group may be carried out as described above in relation to conversion of a protected hydroxymethyl group, etc., to a free hydroxymethyl group, etc.

The resulting hydroxymethylcarbonyl compound may be recovered from the reaction mixture by conventional means. For example, one suitable recovery procedure comprises: pouring the reaction mixture into ice-water; if necessary, neutralizing the mixture; extracting the mixture with a water-immiscible organic solvent; and then evaporating the solvent from the extract, to give the desired product. If necessary, this product may be further purified by such conventional techniques as recrystallization or the various chromatography techniques, e.g. column chromatography or preparative thin layer chromatography.

If the desired product thus obtained is prepared in the form of a mixture of various stereoisomers and optical isomers, the individual isomers can be isolated and resolved at the end of any appropriate synthetic step by the procedures described hereafter. However, isolation from a mixture of isomers relating to a 2- or 3-double bond is preferably carried out for the compound (Ia) in which $R^1$ represents a hydroxymethyl group, and $R^4$ and $R^5$ are both hydroxy-protecting groups.

Conversion of the carboxy group or of the esterified carboxy group to the corresponding amide (i.e. to a carbamoyl group which may be substituted) may be effected by contacting the compound with the appropriate amine in the presence of a solvent. The nature of the amine will, of course, depend upon the amide which it is desired to produce. Suitable amines include ammonia and primary or secondary amines, such as methylamine, ethylamine, propylamine, isopropylamine, butylamine, aniline, p-methylaniline, dimethylamine, methylethylamine, diethylamine, N-methylaniline, N-ethylaniline or N,m-dimethylaniline. The nature of the solvent employed is not critical, provided that it does not interfere with the reaction and preferred solvents include water or an ether (such as diethyl ether, tetrahydrofuran or dioxane).

The reaction may be carried out over a wide range of temperatures, for example from 0° C. to 100° C., and, although the time required for the reaction will vary depending upon the nature of the reagents, the reaction temperature and other reaction conditions, a period of from 1 to 24 hours will normally suffice.

Conversion of the carboxy group to an N-acylcarbamoyl group may be effected by contacting the compound with an acyl isocyanate (such as acetyl isocyanate, trifluoroacetyl isocyanate or benzoyl isocyanate) in an inert solvent, the nature of which is not critical, provided that it does not have any adverse effect upon the reaction. Suitable solvents include: hydrocarbons, such as benzene, toluene or xylene; and ethers, such as diethyl ether, tetrahydrofuran or ethylene glycol dimethyl ether. For convenience, the reaction is normally effected at ambient temperature, although this is not critical, and, although the time required for the reaction may vary, it is generally within the range from 30 minutes to 10 hours.

Conversion of the carboxy group to an N-sulfonylcarbamoyl group may be effected by converting the carboxy group to an active amide and then reacting this with a sulfonic acid amide, such as methanesulfonamide, benzenesulfonamide or n-toluenesulfonamide. The active amide can be prepared by reacting the carboxy compound with an N-hydroxylimide, such as N-hydroxysuccinimide or N-hydroxyphthalimide, in the presence of a condensing agent, such as dicyclohexylcarbodiimide, preferably at about room temperature for a period of from 30 minutes to 10 hours. Reaction of the resulting active amide with the sulfonic acid amide is preferably effected in the presence of a base (such as sodium methoxide, sodium ethoxide or potassium t-butoxide), at about room temperature for a period of from 30 minutes to 15 hours.

Both formation of the active amide and reaction of this with a sulfonic acid amide are preferably effected in the presence of an inert solvent, the nature of which is not critical, provided that it has no adverse effect upon the reaction. Suitable solvents include: aromatic hydrocarbons, such as benzene, toluene or xylene; ethers, such as diethyl ether, tetrahydrofuran or ethylene glycol dimethyl ether; amides, such as dimethylformamide or dimethylacetamide; and sulfoxides, such as dimethyl sulfoxide.

After completion of the reaction, the desired compound can be obtained from the reaction mixture by conventional means. For example, one suitable recovery procedure comprises: pouring the reaction mixture into ice-water; if necessary, neutralizing the mixture; extracting the mixture with a water-immiscible organic solvent; if necessary, washing and drying the extract; and then distilling the solvent from the extract to leave the desired compound. This compound may be further purified, if necessary, by such conventional means as silica gel column chromatography or recrystallization, or a combination thereof.

METHOD B1

This comprises Steps 6-8 inclusive, of the aforementioned reaction scheme. In this method, a compound (Ib) is prepared in which the group A in the compound of general formula (I) represents a group of formula $-(CH_2)_p-E-(CH_2)_q-$ (in which E, p and q are as defined above).

Step 6

In this step, a compound of formula (VII) is prepared by eliminating a group $R^{4a}$ from a compound of formula (VI'), which is a compound of formula (VI), prepared as described in Method A, where the group of formula $R^{14}-A'-$ is a group of formula $R^{4a}-O(CH_2)_q-$, in which $R^{14}$, A', $R^{4a}$ and q are as defined above. The reaction is carried out by the same methods as are used to eliminate hydroxy-protecting groups in Step 5 (Method A).

Step 7

In this step, a compound of formula (VIII) is prepared from the compound of formula (VII).

Where E represents an oxygen atom, this is achieved by reacting the compound of formula (VII) with a compound of formula (XXV):

$$X-(CH_2)_p-R^{15} \qquad (XXV)$$

(in which $R^{15}$, X and p are as defined above). A compound of formula (VIII) in which E represents a sulfur atom is prepared by sulfonylating a compound of formula (VII) and then reacting the sulfonylated compound with a compound of formula (XXVI):

$$HS-(CH_2)_p-R^{15} \qquad (XXVI)$$

(in which $R^{15}$ and p are as defined above) in the presence of a base.

The former reaction is preferably effected by first treating the compound of formula (VII) with a base and then reacting the compound with the aforementioned compound of formula (XXV) or with an alkali metal salt thereof (when $R^{15}$ represents a carboxy group) in an inert solvent. There is no particular restriction upon the nature of the base to be employed and examples of suitable bases include: alkali metal hydrides, such as lithium hydride, sodium hydride or potassium hydride; alkaline earth metal hydrides, such as calcium hydride or barium hydride; organic lithium compounds, such as methyllithium, butyllithium or phenyllithium; alkali metal alkoxides, such as sodium methoxide, sodium ethoxide, potassium ethoxide, sodium propoxide, potassium t-butoxide or sodium t-pentoxide; and alkali metal hydroxides, such as sodium hydroxide or potassium hydroxide. The alkali metal hydrides are preferred. There is no particular restriction upon the nature of the solvent to be employed, provided that it has no adverse effect upon the reaction. Examples of suitable solvents include: hydrocarbons, which can be aliphatic, cycloaliphatic or aromatic, for example hexane, benzene, toluene or xylene; ethers, such as diethyl ether, tetrahydrofuran, ethylene glycol dimethyl ether or diglyme; acid amides, such as dimethylformamide, dimethylacetamide or hexamethylphosphoric triamide; sulfoxides, such as dimethyl sulfoxide; water; and mixtures of any two or more of these solvents. However, the amides and sulfoxides are preferred. These reactions will take place over a wide range of temperatures and the precise temperatures chosen are not particularly critical. However, we prefer that the reaction with the base should be effected at a temperature in the range from $-78°$ C. to $+50°$ C. and that the reaction with the compound of formula (XXV) should be effected at a temperature in the range from $0°$ C. to $50°$ C. The times required for these reactions may vary widely, depending upon the nature of the reagents and the reaction temperature; however, a period of from 10 minutes to 1 hour will normally suffice for reaction with the base, whilst a period of from 1 hour to 48 hours will normally suffice for reaction with the compound of formula (XXV).

A compound in which E represents a sulfur atom is prepared by sulfonylating the compound (VII) and then reacting this with a compound of formula (XXVI) in an inert solvent and in the presence of a base. The sulfonylation reaction may be effected by the method described in Step 4 (Method A). The base and inert solvent employed for the subsequent stage of this reaction are preferably the same as those described above in relation to the reaction to prepare a compound of formula (VIII) in which E represents an oxygen atom. The reaction with the compound of formula (XXVI) will take place over a wide range of temperatures, for example from $0°$ C. to $100°$ C. and the time required for the reaction, which may vary widely, is generally from 30 minutes to 5 hours.

After completion of the reactions described above, the desired product can be recovered from the reaction mixture by conventional means. For example, one suitable recovery technique comprises: pouring the reaction mixture into ice-water; where the mixture is alkaline, acidifying it; extracting the mixture with a water-immiscible organic solvent; and then evaporating the solvent from the extract to give the desired product. If required, this product can be further purified by conventional means, for example by recrystallization or the various chromatography techniques, particularly column chromatography.

Step 8

This step comprises any one or more of a number of optional reactions, although, of course, it may be that the compound of formula (VIII) prepared as described in Step 7 is the desired final product, in which case Step 8 may be omitted altogether. The reactions involved in this step are: elimination of the hydroxy-protecting groups represented by or included within groups represented by $R^{11}$, $R^{12}$ and $R^{7a}$; elimination of the carboxy-protecting group, when $R^{15}$ is a protected carboxy group; converting the group represented by $R^{15}$ to a hydroxymethyl group; converting the resulting hydroxymethyl group to a formyl group (involving a protecting reaction); esterification of a carboxy group represented by $R^{15}$; converting such a carboxy group or esterified carboxy group to a carbamoyl group, which may be substituted; eliminating any formyl-protecting group which may be represented by $R^{7a}$; and converting a carboxy group to a hydroxymethylcarbonyl group (involving protection of hydroxy groups). These reactions may be carried out in any appropriate order.

All of the above reactions, apart from elimination of carboxy-protecting groups, may be carried out as described in Step 5 of Method A. Elimination of the carboxy-protecting group may be carried out as follows.

When the protecting group is a lower alkyl group or an aryl group, it can be eliminated by a conventional hydrolysis reaction. This may be carried out as described for the elimination of hydroxy-protecting groups when such a group is an acyl group.

When the carboxy-protecting group is an aralkyl group, a benzhydryl group or a phenacyl group, it can be eliminated as described above in relation to elimination of hydroxy-protecting groups when those groups are aralkyl groups.

After completion of the above reactions, the desired compound can be recovered from the reaction mixture by conventional means. For example, one suitable recovery technique comprises: acidifying the reaction mixture; extracting the mixture with an appropriate organic solvent; washing and then drying the extract; and then removing the solvent from the extract, to give the desired compound.

METHOD B2

This comprises Steps 9–11. It is used for preparing a compound of formula (Ib'), corresponding to the compound of formula (Ib) prepared as described in Method B1, but in which $R^2$ and $R^3$ both represent hydrogen atoms and p is the integer of 1.

Step 9

In this step, a compound of formula (IX) is prepared by reacting a compound of formula (IV'''), which is a compound of formula (IV) in which $R^2$ and $R^3$ both represent hydrogen atoms and A' represents a single bond, with a compound of formula (XXV) or (XXVI), which are as described in Step 7 (Method B1). The reaction may be carried out in the same way as described in Step 7.

Step 10

In this step, the hydroxy-protecting group in the group represented by $R^{13a}$ is removed, as described in Step 3 (Method A) and then the resulting free hydroxy group is either sulfonylated or replaced by a halogen atom, and then the resulting sulfonylated or halogenated compound is treated with a base, as described in Step 4 (Method A).

Step 11

This step comprises the same sequence of optional steps described in Step 8 (Method B1), which may be carried out, if desired, in accordance with the instructions given in that step.

METHOD B3

This comprises the sequence of steps 12–16 inclusive, to prepare a compound of formula (Ib''), which corresponds to the compound of formula (Ib) described in Method B1, but in which p is 1.

Step 12

In this step, the compound of formula (II) is reacted with a base to generate a carbanion, and this carbanion is then reacted with an aldehyde or ketone of formula (XXVII):

$$R^2R^3C=O \qquad (XXVII)$$

(in which $R^2$ and $R^3$ are as defined above). The reactions involved are similar to those described in Step 1 (Method A) and may be carried out under the same reaction conditions. In this case, the reaction is also preferably carried out in the presence of a titanium compound, such as titanium chlorotripropoxide.

Step 13

In this step, a compound of formula (XII) is prepared by sulfonylating or halogenating the hydroxy group of the compound of formula (XI) prepared as described in Step 12, and then treating the resulting compound with a base. This reaction is essentially the same as that described in Step 4 (Method A) and may be carried out under the same reaction conditions and employing the same reagents.

Step 14

In this step, a compound of formula (XIII) is prepared by reducing the group —$COOR^{20}$ to a hydroxymethyl group, and this reaction can be performed as described in Step 2 (Method A), employing the same reaction conditions and reagents.

Step 15

In this step, a compound of formula (XIV) is prepared by reacting a compound of formula (XIII) with a compound of formula (XXV) or (XXVI), and this reaction can be prepared as described in Step 7 (Method B), employing the same reaction conditions and reagents.

Step 16

This involves the same sequence of optional steps as described in Step 8 (Method B1) and may be carried out employing the same reagents and under the same reaction conditions.

METHOD C

This comprises Steps 17–19 described above and is used to prepare a compound of formula (Ic), corresponding to a compound of formula (I) in which A represents a group of formula —CH=CH—$(CH_2)_n$— in which n is as defined above.

Step 17

In this step, a compound of formula (XV) is prepared by reacting a compound of formula (Ia') [which corresponds to a compound of formula (Ia) in which A represents a group of formula —$(CH_2)_2$—$(CH_2)_n$— and $R^1$ represents $R^5$] with a compound of formula (XXVIII) or (XXIX):

$$R^{16}-W-W-R^{16} \qquad (XXVIII)$$

$$R^{16}-W-X \qquad (XXIX)$$

(in which $R^{16}$, W and X are as defined above).

$R^{15}$ in the compound of formula (Ia') is preferably a protected carboxy group, more preferably a methoxycarbonyl group. $R^{16}$ is preferably an aryl group.

The reaction is preferably effected in the presence of a base, the nature of which is not critical. Suitable bases include organic lithium compounds, for example; alkyl or aryllithiums, such as methyllithium, butyllithium, sec-butyllithium or phenyllithium; dialkylaminolithium compounds, such as diisopropylaminolithium, dicyclohexylaminolithium or isopropylcyclohexylaminolithium; and bis-silyllithium amides, such as bis(trimethylsilyl)lithium amide, bis(triethylsilyl)lithium amide or bis(diphenylmethylsilyl)lithium amide. We prefer to use a dialkyllithium amide.

The reaction is preferably effected in the presence of a solvent, the nature of which is not critical, provided that it has no adverse effect upon the reaction. Suitable solvents include, for example: ethers, such as diethyl ether, tetrahydrofuran, ethylene glycol dimethyl ether or diglyme; and aromatic hydrocarbons, such as benzene, toluene or xylene. The ethers are preferred.

The reactions will take place over a wide range of temperatures and the precise temperatures chosen are not particularly critical. We normally prefer to carry out the reaction with the base at a temperature in the range from −100° C. to room temperature, whilst the reaction with the compound of formula (XXVIII) or (XXIX) is preferably effected at a temperature of from 0° to 50° C. The time required for the former reaction is generally from 10 minutes to 2 hours, whilst that required for the latter reaction is generally from 30 minutes to 5 hours.

After completion of the reaction, the desired product may be recovered from the reaction mixture by conventional means. For example, one suitable recovery procedure comprises: pouring the reaction mixture into water; extracting the mixture with a water-immiscible organic solvent; and then removing the solvent to give the desired product. This product may, if required, be further purified by conventional means, for example recrystallization or the various chromatography techniques, particularly column chromatography.

Step 18

In this step, a compound of formula (XVI) is prepared by oxidizing the compound of formula (XV) and, if necessary, thereafter heating the reaction mixture.

The oxidizing agent employed is preferably hydrogen peroxide or an organic peracid, such as peracetic acid, perpropionic acid, perbenzoic acid or m-chloroperbenzoic acid, of which hydrogen peroxide and m-chloroperbenzoic acid are preferred.

The reaction is preferably effected in the presence of a solvent, the nature of which is not critical, provided that it has no adverse effect upon the reaction. Suitable solvents include, for example: aromatic hydrocarbons, such as benzene, toluene or xylene; halogenated hydrocarbons, such as methylene chloride or chloroform; ethers, such as diethyl ether, tetrahydrofuran, ethylene glycol dimethyl ether or diglyme; esters, such as ethyl acetate; alcohols, such as methanol, ethanol or propanol; water; or a mixture of any two or more of these solvents. For the reaction with hydrogen peroxide, we prefer to use a mixture of water with an alcohol and an ester. For the reaction with an organic peracid, the preferred solvent is a halogenated hydrocarbon.

The reaction will take place over a wide range of temperatures, but we usually prefer to employ a temperature of from −50° C. to +50° C., at which temperature a reaction time of from 30 minutes to 5 hours will normally be required. In order to accelerate formation of the double bond, the reaction can, if required, be performed at a temperature of from 50° C. to 100° C. for a period of from 1 to 5 hours.

After completion of the reaction, the desired product may be recovered from the reaction mixture by conventional means. For example, one suitable recovery technique comprises: pouring the reaction mixture into water; if necessary, filtering off any insoluble substances formed; extracting the mixture with a water-immiscible organic solvent; and then removing the solvent from the extract, to give the desired product. This product may, if required, be further purified by conventional means, for example recrystallization or the various chromatography techniques, particularly column chromatography.

Step 19

In this step, any one or more of a series of optional reactions may be performed, unless the compound of formula (XVI) prepared in Step 18 is the desired product, in which case Step 19 may be omitted. The reactions involved are: eliminating the hydroxy-protecting groups represented by $R^4$ and/or $R^5$; eliminating any carboxy-protecting group in $R^{15}$; converting $R^{15}$ to a hydroxymethyl group converting this hydroxymethyl group to a formyl group; esterifying any carboxy group in $R^{15}$; and converting this carboxy group or esterified carboxy group to a carbamoyl group, which may be substituted. These reactions may be carried out in any appropriate order and are identical to the reactions described in Step 8 (Method B1).

METHOD D

This comprises the sequence of steps 20–23 and prepares a compound of formula (Id), which corresponds to the compound of formula (I) in which B represents a vinylene group or an ethynylene group.

Step 20

In this Step, an unsaturated ketone of formula (XVIII) is prepared by reacting an aldehyde of formula (XVII) with a Wittig reagent or modified Wittig reagent of formula (XXX) or (XXXI):

$(R^{16})_3P^+{-}^-C(Y)COR^{7a}$ (XXX)

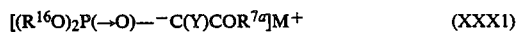

$[(R^{16}O)_2P({\rightarrow}O){-}^-C(Y)COR^{7a}]M^+$ (XXXI)

In the above formulae $R^{7a}$, $R^{16}$ and M are as defined above, and Y represents a hydrogen atom or a halogen atom.

The Wittig reagent or modified Wittig reagent formula (XXX) or (XXXI) can be prepared by conventional means by reacting a compound of formula (XXX') or (XXXI'):

$(R^{16})_3P^+{-}CH(Y)COR^{7a}.X^-$ (XXX')

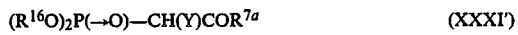

$(R^{16}O)_2P({\rightarrow}O){-}CH(Y)COR^{7a}$ (XXXI')

(in which $R^{7a}$, $R^{16}$, X and Y are as defined above) in the presence of a solvent, with an alkali metal base, for example: an alkali metal hydride, such as sodium hydride or potassium hydride; an alkali metal alkoxide, such as sodium methoxide, sodium ethoxide or potassium t-butoxide; an alkali metal amide, such as sodium amide or potassium amide; an alkyl-alkali metal, such as butyllithium; or an alkali metal dimethyl sulfoxide anion, such as sodium dimethyl sulfoxide anion. There is no particular restriction upon the nature of the solvent to be employed, and any solvent commonly used in Wittig reactions may equally be used in this reaction. Examples of suitable solvents include: ethers, such as diethyl ether, tetrahydrofuran, dioxane or ethylene glycol dimethyl ether; thio ethers, such as sulfolane; hydrocarbons, such as benzene, toluene or hexane; dialkyl sulfoxides, such as dimethyl sulfoxide; acid dialkylamides, such as dimethylformamide or dimethylacetamide; halogenated hydrocarbons, such as methylene chloride or chloroform; and phosphoric acid triamides, such as hexamethylphosphoric triamide. The reaction is preferably effected under an atmosphere of an inert gas, such as nitrogen, argon or helium.

The reaction will take place over a wide range of temperatures and the precise reaction temperature chosen is not particularly critical. We usually prefer to carry out the reaction at a temperature in the range from −10° C. to the reflux temperature of the solvent used. The time required for the reaction may vary widely, depending upon many factors, notably the reaction temperature and the nature of the reagents, but a period of from 6 to 50 hours will normally suffice.

After the reaction is complete, the desired Wittig reaction product can be recovered from the reaction mixture by conventional means. For example, one suitable recovery procedure comprises: pouring the reaction mixture into ice-water; if necessary, treating the mixture with an acid; extracting the mixture with a water-immiscible organic solvent, such as diethyl ether; washing the extract with water and drying it; and then evaporating the solvent from the extract, to give the desired product.

Step 21

In this Step, an alcohol derivative of formula (XIX) is prepared from the compound of formula (XVIII). A compound (XIX) in which $R^6$ represents a hydrogen atom is prepared by reacting the compound (XVIII) with a reducing agent, whilst a compound (XIX) in which $R^6$ represents a $C_1$-$C_4$ alkyl group is prepared by reacting the compound (XVIII) with a Grignard reagent (XXII) as described in Step 2 (Method A); this reaction may be carried out as described in Step 2.

The reaction with the reducing agent is preferably effected in an inert solvent, the nature of which is not critical, provided that it has no adverse effect upon the reaction. Examples of suitable solvents include: alcohols, such as methanol, ethanol, propanol, butanol and t-butanol; ethers, such as diethyl ether, tetrahydrofuran or dioxane; and mixtures of any two or more of these solvents. The alcohols, particularly methanol, are preferred.

There is no particular restriction upon the nature of the reducing agent employed, provided that it is capable of reducing a carbonyl group to a hydroxy group without affecting the remainder of the molecule. Suitable reducing agents include: metal hydrides, such as sodium borohydride, potassium borohydride, lithium borohydride, zinc borohydride, lithium tri-t-butoxyaluminohydride, lithium trimethoxyaluminohydride or sodium cyanoborohydride; and aluminum compounds, such as aluminum isopropoxide or diisobutyl(2,6-di-t-butyl-4-methylphenoxy)aluminum. Sodium borohydride is preferred.

In order to suppress reduction of the double bond, cerium chloride may be added to the reaction mixture.

The reaction will take place over a wide range of temperatures and the precise reaction temperature chosen is not particularly critical. We generally prefer to carry out the reaction at a temperature in the range from 0° C. to room temperature. The time required for the reaction may vary, depending upon many factors, notably the nature of the reagents and the reaction temperature; however, a period of from 10 minutes to 2 hours will normally suffice.

After completion of the reaction, the desired product may be recovered from the reaction mixture by conventional means. For example, one suitable recovery technique comprises: removing the solvent by evaporation under reduced pressure; adding ice-water to the residue; extracting the mixture with a water-immiscible organic solvent; and then removing the solvent from the extract, to give the desired product.

When $R^{17}$ in the compound of formula (XVIII), which is the starting material for this Step, is a hydroxymethyl group, the compound may first be subjected to a reaction to protect the hydroxy group before carrying out this Step; such a protecting reaction may be carried out as described hereafter in Step 22.

Step 22

If necessary, a compound of formula (XX) may be prepared by converting the halovinylene group (Y=halogen) of the compound of formula (XIX) to an ethynylene group and protecting the hydroxy group of the compound of formula (XIX).

Conversion of the halovinylene group to an ethynylene group can be effected by reacting the compound of formula (XIX) with a base in an inert solvent.

There is no particular restriction upon the nature of the base and examples include: alkali metal alkoxides, such as sodium methoxide, potassium ethoxide, potassium t-butoxide or sodium t-pentoxide; and alkali metal hydroxides, such as sodium hydroxide or potassium hydroxide. A strong base, such as potassium t-butoxide, sodium t-pentoxide or potassium hydroxide is preferred.

There is no particular restriction upon the nature of the inert solvent, provided that it has no adverse effect upon the reaction. Preferred solvents include: alcohols, such as methanol, ethanol or t-butanol; and ethers, such as diethyl ether or tetrahydrofuran.

The reaction will take place over a wide range of temperatures, but we generally find it convenient to carry out the reaction at a temperature in the range from room temperature to the reflux temperature of the solvent employed. The time required may vary widely, but a period of from 30 minutes to 5 hours will normally suffice. After completion of the reaction, the desired product may be recovered from the reaction mixture by conventional means. For example, one suitable recovery technique comprises: if necessary, evaporating the solvent from the reaction mixture under reduced pressure; pouring the reaction mixture, either with or without evaporation of the solvent, into ice-water; if necessary, neutralizing the mixture; extracting the mixture with an appropriate organic solvent; washing the extract with water and then drying it; and then evaporating the solvent from the extract to give the desired product. This product may, if necessary, be further purified by such conventional techniques as recrystallization or the various chromatography techniques, notably silica gel column chromatography.

Protection of the hydroxy group may be carried out by conventional means by contacting the compound (XIX) with a protecting agent, before or after preparation of the ethynylene group. Preferred protecting agents include, for example: carboxylic acids and reactive derivatives thereof, such as acetic acid, propionic acid, butyric acid, benzoic acid or naphthoic acid; aralkyl halides, such as benzyl chloride, benzyl bromide, p-nitrobenzyl bromide or p-methoxybenzyl bromide; trityl halides, such as trityl chloride or trityl bromide; heterocyclic compounds containing 5-6 ring atoms, such as dihydropyran, dihydrothiopyran, dihydrothiophene or 4-methoxy-5,6-dihydro(2H) pyran; alkoxyalkyl, alkylthioalkyl and aralkyloxyalkyl halides, such as methoxymethyl chloride, methylthiomethyl chloride, ethoxyethyl chloride or benzyloxymethyl chloride; unsaturated ethers such as methyl vinyl ether or ethyl vinyl ether; and silyl compounds, such as hexamethyldisilazane, trimethylsilyl chloride, tripropylsilyl chloride, t-butyldimethylsilyl chloride or t-butyldiphenylsilyl chloride.

When a carboxylic acid is employed, the reaction is preferably carried out in the presence of a condensing agent, such as dicyclohexylcarbodiimide.

Examples of suitable reactive derivatives of carboxylic acids include: acid halides, such as acetyl chloride, acetyl bromide, benzoyl chloride, benzoyl bromide or naphthoyl chloride; and acid anhydrides, such as acetic anhydride, propionic anhydride or benzoic anhydride. When such a reactive derivative is used, the reaction is preferably carried out in the presence of an organic base, such as triethylamine, pyridine, 4-dimethylaminopyridine, quinoline or N,N-dimethylaniline.

Reaction with a carboxylic acid or reactive derivative thereof is preferably carried out in the presence of a solvent. The nature of the solvent is not critical, provided that it has no adverse effect on the reaction. Suitable solvents include: hydrocarbons, such as benzene, toluene, xylene or hexane; halogenated hydrocarbons, such as methylene chloride, chloroform, carbon tetrachloride or chlorobenzene; ethers, such as diethyl ether, tetrahydrofuran or dioxane; and ketones, such as acetone or methyl ethyl ketone. Of these, the hydrocarbons are preferred.

The reaction temperature is preferably within the range from 0° C. to 100° C. and the time required for the reaction, although varying depending upon the reagents, reaction temperature and other reaction conditions, is usually from 30 minutes to 6 hours.

When an aralkyl halide, a trityl halide, an alkoxyalkyl halide, an alkylthioalkyl halide, an aralkoxyalkyl halide or a silyl compound is used as the protecting reagent, the compound of formula (XIX) is preferably first converted to its alkali metal salt, for example by treatment with an alkali metal hydride such as sodium hydride or potassium hydride. This salt is then reacted with the appropriate halide or silylating agent (such as disilazane) in an inert solvent.

The nature of the solvent employed in this reaction is not critical, provided that it has no adverse effect upon the reaction. Examples of suitable solvents include: ethers, such as diethyl ether, tetrahydrofuran and dioxane; amides, such as dimethylformamide, dimethylacetamide or hexamethylphosphoric triamide; nitriles, such as acetonitrile or benzonitrile; and sulfoxides, such as dimethyl sulfoxide. Of these, the amides are preferred.

The reaction temperature is preferably from 0° C. to 100° C., and the time required for the reaction, although varying depending upon the nature of the reagents, the reaction temperature and other reaction conditions, is usually from 10 minutes to 3 hours.

The reaction of the compound of formula (XIX) may be carried out in the presence of an organic base, such as triethylamine, pyridine, 4-dimethylaminopyridine or imidazole, or an inorganic base, such as sodium hydroxide, potassium hydroxide or potassium carbonate.

When a 5- or 6-membered heterocyclic compound or an unsaturated ether is employed, the reaction may be conducted in the presence or absence of an inert solvent and is preferably conducted in the presence of a small amount of an acid. Suitable acids include mineral acids (such as hydrochloric acid or hydrobromic acid) and organic acids (such as picric acid, trifluoroacetic acid, benzenesulfonic acid, p-toluenesulfonic acid or camphorsulfonic acid).

The nature of the solvent employed in this reaction is not critical, provided that it does not interfere with the reaction and examples of suitable such solvents include: ethers, such as diethyl ether, tetrahydrofuran or dioxane; halogenated hydrocarbons, such as methylene chloride, chloroform or carbon tetrachloride; and aromatic hydrocarbons, such as benzene, toluene or xylene. Of these, the halogenated hydrocarbons are preferred. Alternatively, an excess of the heterocyclic compound or of the vinyl ether may serve as a solvent in the absence of any added solvent.

The reaction temperature is preferably from 0° C. to 50° C., and the time required for the reaction, although varying depending upon the nature of the reagents, the reaction temperature and other reaction conditions, is usually from 30 minutes to 3 hours.

After completion of the reaction, the resulting compound of formula (XX) in which the hydroxy groups are protected may be removed from the reaction mixture by conventional means. For example, one suitable recovery procedure comprises: pouring the reaction mixture into ice-water; separating insoluble materials, if any, by filtration; neutralizing the filtrate; extracting the desired compound with a water-immiscible organic solvent; and then removing the solvent by distillation. If required, the compound may be further purified by conventional means, for example by column chromatography, thin layer chromatography or recrystallization, or by any combination thereof.

Sometimes, in the course of the reactions outlined above, a substantial quantity of the compound of formula (XIX) having the 3$\beta$-hydroxy group in the $\omega$-chain is produced. Since the 3$\beta$-hydroxy compound is less important, this may be removed by conventional methods, for example, recrystallization, column chromatography or a combination thereof after, if desired, removing the hydroxy protecting group by $R^{11}$ and the 3$\alpha$-hydroxy compound thus obtained may be also protected.

Step 23

This comprises a sequence of optional steps as described in Steps 5 (Method A) and 8 (Method B1) and may be carried out as described in those steps.

The starting material of formula (XVII) employed in Method D may be prepared by Methods E, F or G, as illustrated by the following schemes:

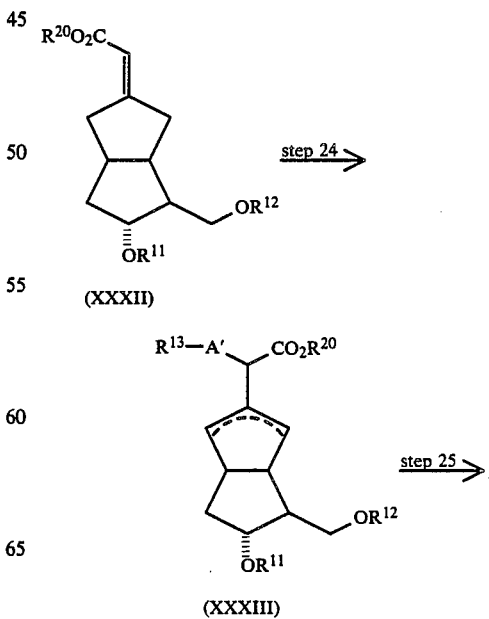

-continued
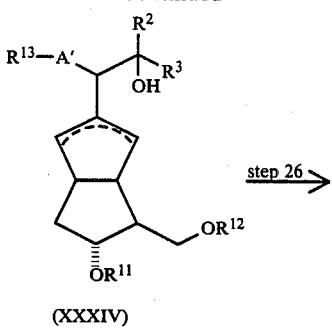
(XXXIV)
step 26 →
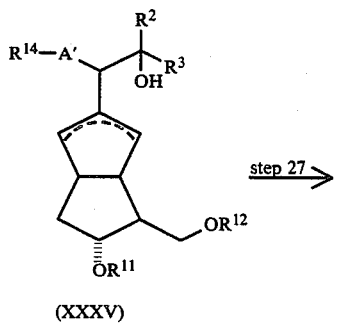
(XXXV)
step 27 →
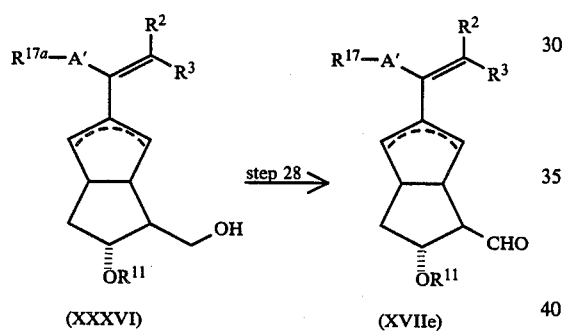
(XXXVI) (XVIIe)
step 28 →
-continued
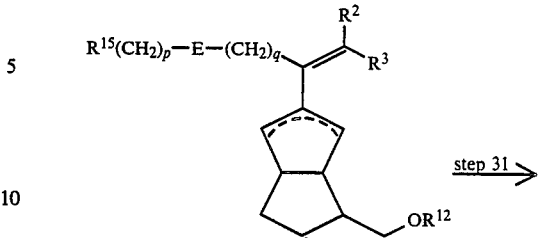
(XXXVIII)
step 31 →
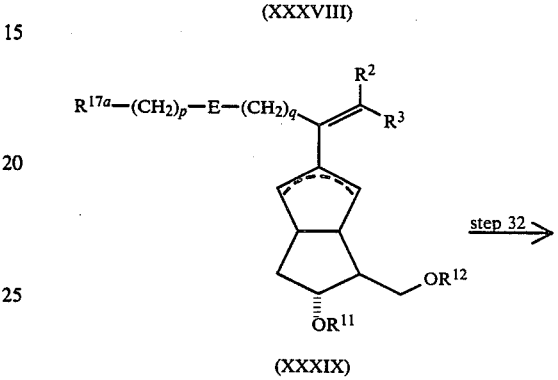
(XXXIX)
step 32 →
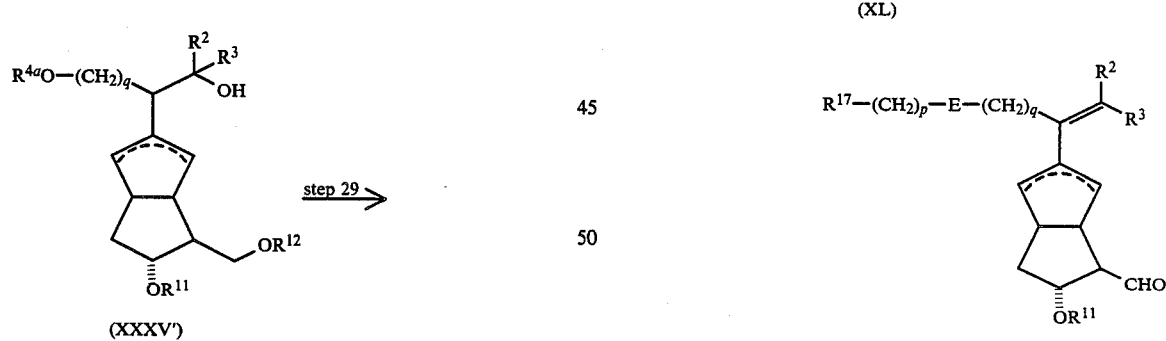
(XL) (XVIIf)
step 33 →
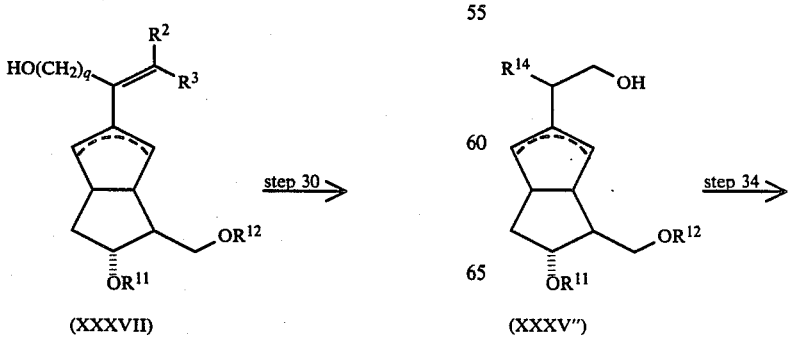
(XXXV') (XXXVII) (XXXV'')
step 29 → step 30 → step 34 →

-continued
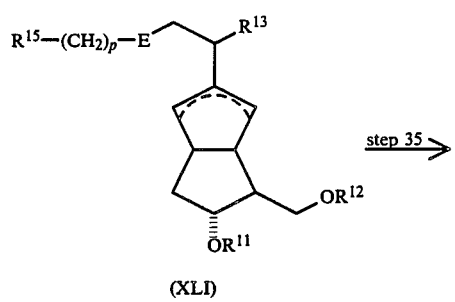
(XLI)
step 35 →
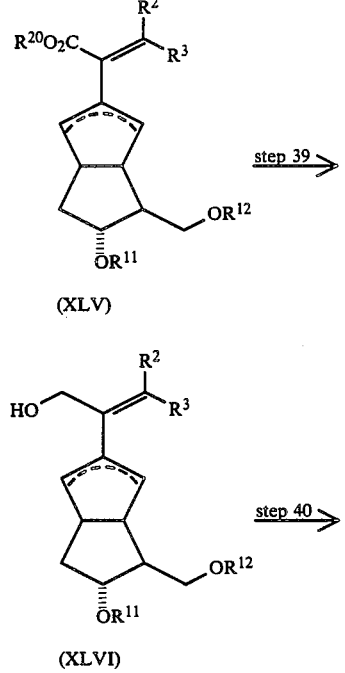
(XLII)
step 36 →
(XLIII)
(XXXII)
step 37 →
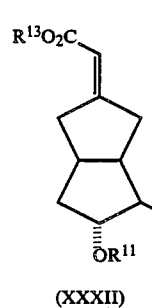
(XLIV)
step 38 →
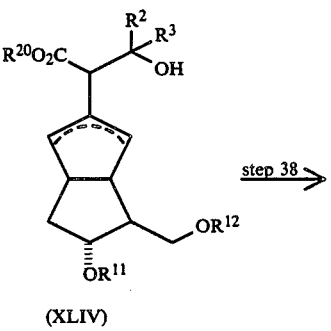
(XLV)
step 39 →
(XLVI)
step 40 →
(XLVII)
(XLVIII)
step 41 →
(XLIX)
step 42 →

-continued

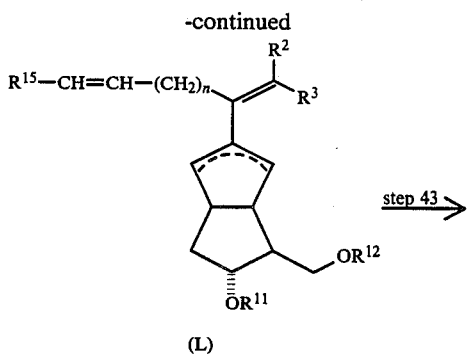

(L)

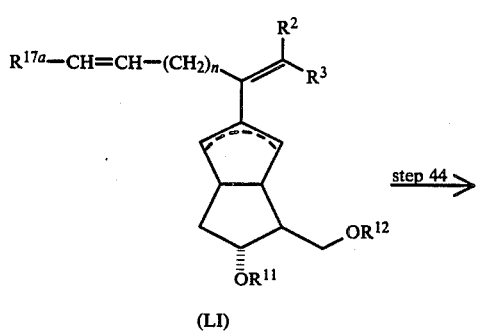

(LI)

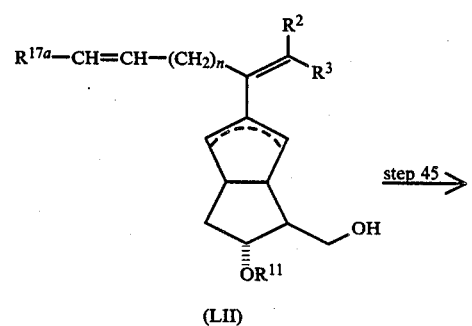

(LII)

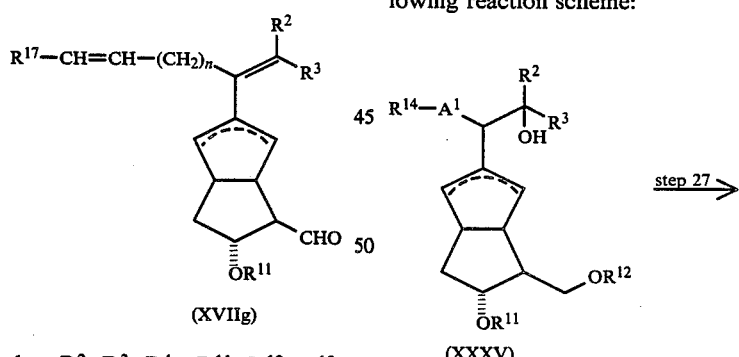

(XVIIg)

In the above formulae, $R^2$, $R^3$, $R^{4a}$, $R^{11}$, $R^{12}$, $R^{13}$, $R^{14}$, $R^{15}$, $R^{16}$, $R^{17}$, A′, E, W, n, p, q and the dotted line are as defined above. $R^{15a}$ represents a protected carboxy group or a tetrazolyl group, and $R^{17a}$ represents a protected carboxy group, a protected hydroxy group, a protected formyl group or a tetrazolyl group.

METHOD E

In this, a compound of formula (XVIIe) is prepared, corresponding to the compound of formula (XVII) employed as a starting material in Method D, in which A represents a single bond or a straight-chain $C_1$-$C_4$ alkylene group which is optionally fluorinated.

Steps 24–26

These are carried out as described in Steps 1–3 of Method A, to give a compound of formula (XXXU) from the starting material of formula (XXXII), via the intermediates of formulae (XXXIII) and (XXXIV).

Compounds (XXXII) are known or may be prepared from known compounds using known methods (see Chem. Pharm. Bull., 32, 3768 (1984) and European Patent Publication No. 136779).

Step 27

In this step, a compound of formula (XXXVI) is prepared by: first, either sulfonylating the hydroxy group of the compound of formula (XXXV) or replacing the hydroxy group with a halogen group; and then reacting the resulting compound with a base; and, if desired, subsequently eliminating the hydroxy-protecting group represented by $R^{12}$. If desired, if the hydroxy-protecting group protecting the protected hydroxymethyl group represented by $R^{14}$ is eliminated, this may be re-protected, the hydroxymethyl group may, if desired, be converted to a carboxy group and the carboxy group may, if desired, be protected.

Each of these reactions can be carried out in the same way as described in relation to the corresponding reactions in Steps 4 and 5 (Method A) or in Step 21 (Method D).

When $R^{11}$ and $R^{12}$ are such protecting groups that they can be eliminated simultaneously under the same reaction conditions, both groups will be removed when $R^{12}$ is eliminated. In this case, if desired, selective protection of the secondary hydroxy group can be achieved by making use of the difference in reactivity between primary and secondary hydroxy groups. For example, this may be achieved as illustrated in the following reaction scheme:

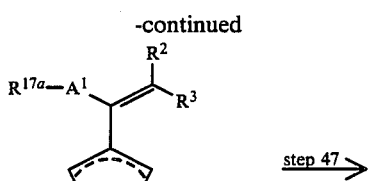

(LIV)

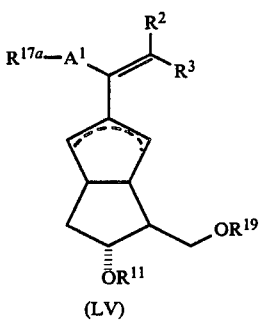

(LV)

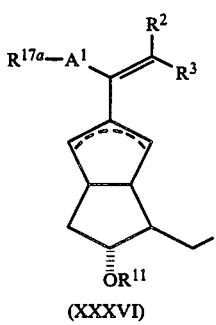

(XXXVI)

In the above formulae, $R^2$, $R^3$, $R^{17a}$, $R^{11}$, A' and the dotted line are all as defined above, and $R^{19}$ represents a reactive acyl group.

Steps 46 and 47

First, the compound of formula (LIII) in which both $R^{11}$ and $R^{12}$ have been eliminated is converted in Step 46 to a compound of formula (LIV) by reaction with a reactive acylating agent, such as trichloroacetyl chloride or trifluoroacetyl chloride. The primary hydroxy group, being the more reactive, is preferentially acylated. In Step 47, the free hydroxy group is then separated protected, to give the compound of formula (LV). These reactions may be carried out in the same way as the corresponding reactions in Step 22 (Method D). In Step 46, the reaction is preferably carried out under mild reaction conditions and without using any excess of the reactive acylating agent.

Step 48

In this step, the resulting di-protected compound is subjected to a mild hydrolysis reaction, to give the desired product of formula (XXXVI).

This is preferably effected by treating the compound (LV) with a weak base in the presence of an inert solvent and under mild reaction conditions.

Suitable bases include, for example: alkali metal bicarbonates, such as sodium bicarbonate or potassium bicarbonate; alkali metal salts of aliphatic carboxylic acids, such as sodium acetate or potassium acetate; basic alumina; and organic amines, such as triethylamine or pyridine. The alkali metal bicarbonates are preferred.

There is no particular restriction upon the nature of the solvent to be employed, provided that it does not interfere with the reaction. Suitable solvents include, for example: alcohols, such as methanol, ethanol, propanol or isopropanyl; ethers, such as diethyl ether, tetrahydrofuran, dioxane or ethylene glycol dimethyl ether; dialkyl sulfoxides, such as dimethyl sulfoxide; and mixtures of such organic solvents with water.

The reaction will take place over a wide range of temperatures and the precise reaction temperature chosen is not particularly critical. We generally prefer to carry out the reaction at the temperature in the range from room temperature to 50° C. The time required for the reaction may vary, depending upon many factors, notably the reaction temperature, but a period of from 1 to 12 hours will normally suffice.

Step 28

In this step, the compound of formula (XVIIe) is prepared by oxidizing the compound of formula (XXXVI). This may be carried out in the same way as the corresponding reaction described in Step 5 (Method A). If desired, carboxy-protecting groups and/or hydroxy-protecting groups may be eliminated.

METHOD F

This comprises either (1) Steps 29–33 inclusive or (2) Steps 34–36 inclusive or (3) Steps 37–40 inclusive. It is designed to prepare a compound of formula (XVIIf), which is a compound of formula (XVII) in which A represents a group of formula —(CH$_2$)$_p$—E—(CH$_2$)$_q$—, in which E, p and q are as defined above.

Steps 29 and 30

In these, a compound of formula (XXXVIII) is prepared from the starting material of formula (XXXV') [which corresponds to the compound of formula (XXXV) in which $R^{14}$—A'— is a group of formula $R^{4a}$—O—(CH$_2$)$_q$—] via the intermediate of formula (XXXVII). These steps are carried out in the same way as Steps 4 (Method A) and 6 and 7 (Method B).

Step 31

In this step, where $R^{15}$ in the compound of formula (XXXVIII) is a carboxy group, it is protected; alternatively, if the carboxy group of $R^{15}$ has been converted to a hydroxymethyl group, then the hydroxy group is protected. These reactions may be carried out as described in relation to the corresponding reactions in Steps 5 (Method A) and 22 (Method D).

Steps 32 and 33

A formyl compound of formula (XVIIf) is prepared by oxidizing a hydroxymethyl compound (XL) obtained by eliminating $R^{12}$ from the compound of formula (XXXIX) and these reactions are performed in the same way as the corresponding reactions in Steps 27 and 28 (Method E).

Method F2 provides a different process for preparing a compound of formula (XLIII) in which q in the compound of formula (XXXIX) is the integer 1.

Steps 34–36

These start with a compound of formula (XXXV'') [corresponding to the compound of formula (XXXV) in which $R^2$ and $R^3$ represent hydrogen atoms and n is 0] via intermediate compounds of formulae (XLI) and (XLII). These steps are performed in the same way as described in Steps 9 and 10 (Method B) and 31 (Method F).

Method F3 provides a different process for preparing a compound of formula (XLVII) corresponding to a compound of formula (XXXVIII) in which q is 1. In Steps 37–40 of this method, the starting material of formula (XXXII) is converted via intermediates of formulae (XLIV), (XLV) and (XLVI) to the compound of formula (XLVII). The reactions involved in these steps are precisely the same as those involved in Steps 12–15, respectively (Method B3).

METHOD G

In this method, a compound of formula (XVIIg) is prepared, corresponding to the compound of formula (XVII) in which A represents a group of formula —CH=CH—(CH$_2$)$_n$—, in which n is as defined above. The reactions involved in Steps 41–45 of this method are the same as those involved in Steps 17 and 18 (Method C) and 33–35 (Method F), respectively. The desired compound (VIIg) is prepared from a compound of formula (XLVIII) obtained prior to elimination of the protecting group R$^{12}$ in Step 27 (Method E) via intermediate compounds of formula (XLIX), (XL), (LI) and (LII).

When the desired compound obtained in each step is a mixture of various kinds of positional isomers, geometric isomers and optical isomers, the individual isomers can, if desired, be separated and resolved at any appropriate stage in the synthesis.

PHARMACOLOGICAL ACTIVITY

The compounds of the invention have shown excellent thrombocyte agglutination inhibitory, anti-ulcer, coronary blood vessel dilatory and bronchodilatory activities. Of these activities, the results of a study of thrombocyte agglutination inhibition will be discussed in more detail below.

The inhibition of platelet aggregation was assessed by Born's turbidimeteric method [Nature, 194, 927–929 (1962)].

Blood was collected from either rabbit or human sources and mixed with one tenth of its volume of a 3.8% w/v sodium citrate solution, and the mixture was centrifuged, to prepare a platelet-rich plasma. Platelet aggregation was determined by the following means: 0.05 ml of a test liquid (containing, in various concentrations, the compound whose inhibitory effect was to be tested) was added to 1 ml of this platelet-rich plasma; two minutes after the addition, 0.2 ml of a liquid containing adenosine diphosphate at a concentration of 5 $\mu$M was added; the increase in light transmission at 600 nm was determined by means of a platelet aggregometer manufactured by Bryston Co. Limited. The inhibition of platelet aggregation was assessed by comparing the increase in the amount of light transmitted through the test sample-treated platelet-rich plasma with a control platelet-rich plasma which had been treated in the same way except that the test compound was omitted. The concentration required for a 50% inhibition was calculated and the results are shown in the following Table. The compounds of the invention are identified by the numbers assigned to them in the foregoing list and are the isomers specifically listed as preferred compounds, whilst the prior art compounds also tested and whose results are also given are identified by the following codes:

Compound A: PGE$_1$, which has the formula:

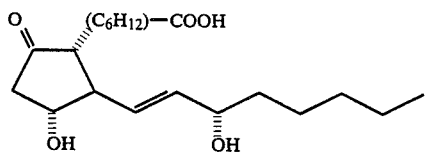

Compound B: carbacyclin, which has the formula:

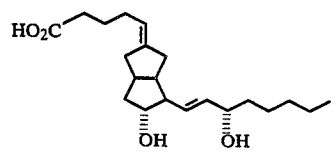

TABLE

| Test Compound | Concentration (ng/ml) for 50% inhibition | |
|---|---|---|
| | Rabbit blood | Human blood |
| 3a | 1.1 | 1.0 |
| 98b | 5.1 | 0.4 |
| 113b | 4.7 | 0.8 |
| 122a | 1.2 | 0.7 |
| A | 36 | 9.3 |
| B | 36 | 13.3 |

As can be seen from the results in the above Table, the activity of the compounds of the invention is substantially better than that of the prior art compounds and, accordingly, the compounds of the invention are useful for the inhibition of platelet aggregation and can be used for the prophylaxis and treatment of thrombotic diseases. The compounds may be administered orally or parenterally, for example as tablets, capsules, granules, powders, syrups or intravenous injections. The dose will depend upon the route of administration, as well as upon the symptoms, age and body weight of the patient, but the preferred dose for an adult human would normally be from 0.0001 mg to 1000 mg, more preferably from 0.01 mg to 100 mg, per day, which may be administered in a single dose or in divided doses.

The invention is further illustrated by the following Examples, which describe preparation of various compounds of the present invention. The preparation of starting materials for use in these Examples, except where the starting materials are otherwise well-known, is described in the following Preparations. All measurements of optical rotation were made using the sodium D-line, i.e. all are [$\alpha$]$_D$.

EXAMPLE 1

Mixture of
3-(1-methoxycarbonyl-5-benzyloxypentyl)-6$\beta$-[3$\alpha$-(2-tetrahydropyranyloxy)-5(R),9-dimethyl-1,8-decadienyl]-7$\alpha$-(2-tetrahydropyranyloxy)bicyclo[3.3.0]oct-2-ene and 3-(1-methoxycarbonyl-5-benzyloxypentyl)-6$\beta$-[3$\alpha$-(2-tetrahydropyranyloxy)-5(R),9-dimethyl-1,8-decadienyl]-7$\alpha$-(2-tetrahydropyranyloxy)bicyclo[3.3.0]oct-3-ene 1.9 ml of dicyclohexylamine was dissolved in 40 ml of anhydrous tetrahydrofuran, and the solution was cooled to −78° C. 5.8 ml of a 15% w/w solution of butyllithium in hexane were added dropwise to the solution, and the mixture was stirred for 10 minutes. 1.82 ml of hexamethylphosphoric triamide was added dropwise to this solution and the mixture was stirred for 5 minutes. Separately, 2.6 g of 3,3-(methoxycarbonylmethylene)-6β-[3α-(2-tetrahydropyranyloxy)-5β,9-dimethyl-1,8-decadienyl]-7α-(2-tetrahydropyranyloxy)bicyclo[3.3.0]octane (prepared following the procedures described in European Patent Publication No. 136779) were dissolved in 15 ml of tetrahydrofuran, and the resulting solution was added dropwise to the above-mentioned mixture and stirred for 10 minutes at −78° C. 2.32 g of 4-benzyloxybutyl bromide were added to this solution and the mixture was gradually restored to room temperature and then stirred for 1 hour at room temperature. 10 ml of a saturated aqueous solution of ammonium chloride were added to this reaction mixture, whilst stirring, and the reaction mixture was then diluted with 150 ml of water. This solution was extracted with ethyl acetate, and the extract was washed with water and dried over anhydrous sodium sulfate. The solvent was distilled off under reduced pressure, to yield 4.67 g of a residue, which was subjected to silica gel column chromatography, eluted with hexane containing from 20 to 30% v/v ethyl acetate, to give 2.7 g of a mixture of the title compounds.

Infrared Absorption Spectrum (liquid film) $\nu_{max}$cm$^{-1}$: 1025, 1120, 1740.

Nuclear Magnetic Resonance Spectrum (CDCl$_3$) δ ppm: 0.92 (3H, doublet); 3.62 (3H, singlet); 4.45 (2H, singlet); 4.9–5.7 (4H, multiplet); 7.30 (5H, singlet).

EXAMPLE 2

Mixture of
3-(1-hydroxymethyl-5-benzyloxypentyl)-6β-[3α-(2-tetrahydropyranyloxy)-5(R),9-dimethyl-1,8-decadienyl]-7α-(2-tetrahydropyranyloxy)bicyclo[3.3.0]oct-2-ene
and
3-(1-hydroxymethyl-5-benzyloxypentyl)-6β-(3α-(2-tetrahydropyranyloxy)-5(R),9-dimethyl-1,8-decadienyl]-7α-(2-tetrahydropyranyloxy)bicyclo[3.3.0]oct-3-ene 0.29 g of lithium aluminum hydride was suspended in 80 ml of anhydrous diethyl ether. While this suspension was stirred and ice-cooled, a solution of 2.7 g of the mixture of 3-(1-methoxycarbonyl-5-benzyloxypentyl)-6β-[3α-(2-tetrahydropyranyloxy)-5(R),9-dimethyl-1,8-decadienyl]-7α-(2-tetrahydropyranyloxy)bicyclo[3.3.-0]oct-2-ene and its oct-3-ene isomer, prepared as described in Example 1, dissolved in 15 ml of diethyl ether was added dropwise, and the mixture was stirred for 15 minutes at room temperature, 1.2 ml of a 4% w/v aqueous solution of sodium hydroxide was added dropwise to this solution, and the mixture was stirred for 1 hour at room temperature. The insoluble matter which precipitated out was filtered off using a Celite (trade mark) filter aid, and the filtrate was condensed by evaporation under reduced pressure. The resulting residue was subjected to silica gel column chromatography, eluted with hexane containing from 20 to 40% v/v ethyl acetate, yielding 2.53 g of a mixture of the title compounds.

Infrared Absorption Spectrum (liquid film) $\nu_{max}$cm$^{-1}$: 975, 1020, 1075, 1120, 3480.

Nuclear Magnetic Resonance Spectrum (CDCl$_3$) δ ppm: 0.95 (3H, doublet); 4.50 (2H, singlet); 4.70 (2H, broad singlet); 5.0–5.7 (4H, multiplet); 7.33 (5H, singlet).

EXAMPLE 3

Mixture of
3-(1-t-butyldimethylsilyloxymethyl-5-benzyloxypentyl)-6β-[3α-(2-tetrahydropyranyloxy)-5(R),9-dimethyl-1,8-decadienyl]-7α-(2-tetrahydropyranyloxy)bicyclo[3.3.0]oct-2-ene
and
3-(1-t-butyldimethylsilyloxymethyl-5-benzyloxypentyl)-6β-[3α-(2-tetrahydropyranyloxy)-5(R),9-dimethyl-1,8-decadienyl]-7α-(2-tetrahydropyranyloxy)bicyclo[3.3.0]oct-3-ene 2.53 g of the mixture of 3-(1-hydroxymethyl-5-benzyloxypentyl)-6β-[3α-(2-tetrahydropyranyloxy)-5(R),9-dimethyl-1,8-decadienyl]-7α-(2-tetrahydropyranyloxy)bicyclo[3.3.0]oct-2-ene and its oct-3-ene isomer, prepared as described in Example 2, were dissolved in 25 ml of dimethylformamide. 0.68 g of t-butyldimethylsilyl chloride, 0.30 g of imidazole and 54 mg of 4-dimethylaminopyridine were added to this solution, and the mixture was left standing for 5 hours at room temperature. The reaction mixture was then diluted with 150 ml of water, and this solution was extracted with ethyl acetate. The resulting extract was washed with water and dried with anhydrous sodium sulfate. The solvent was distilled off under reduced pressure. The resulting residue was subjected to silica gel column chromatography, eluted with hexane containing from 0 to 10% v/v ethyl acetate, yielding 2.99 g of a mixture of the title compounds.

Infrared Absorption Spectrum (liquid film) $\nu_{max}$cm$^{-1}$: 835, 1020, 1075, 1115.

Nuclear Magnetic Resonance Spectrum (CDCl$_3$) δppm: 4.50 (2H, singlet); 5.0–5.7 (4H, multiplet); 7.34 (5H, singlet).

EXAMPLE 4

Mixture of
3-(1-t-butyldimethylsilyloxymethyl-5-hydroxypentyl)-6β-[3α-(2-tetrahydropyranyloxy)-5(R),9-dimethyl-1,8-decadienyl]-7α-(2-tetrahydropyranyloxy)bicyclo[3.3.-0]oct-2-ene and
3-(1-t-butyldimethylsilyloxymethyl-5-hydroxypentyl)-6β-[3α-(2-tetrahydropyranyloxy)-5(R),9-dimethyl-1,8-decadienyl]-7α-(2-tetrahydropyranyloxy)bicyclo[3.3.-0]oct-3-ene A solution of 2.9 g of the mixture of 3-(1-t-butyldimethylsilyloxymethyl-5-benzyloxypentyl)-6β-[3α-(2-tetrahydropyranyloxy)-5(R),9-dimethyl-1,8-decadienyl]-7α-(2-tetrahydropyranyloxy)bicyclo[3.3.0]oct-2-ene and its oct-3-ene isomer, prepared as described in Example 3, dissolved in 50 ml of tetrahydrofuran was added to 50 ml of liquid ammonia cooled at −78° C. 0.6 g of metallic sodium was added to this solution, and the mixture was stirred for 15 minutes at −70° to −50° C. Approximately 5 g of ammonium chloride powder were then added to this mixture, and the temperature of the mixture was gradually raised up to room temperature to remove the ammonia. The remaining reaction mixture was diluted with 150 ml of water, and the diluted solution was extracted with ethyl acetate. The resulting extract was washed with water and dried with anhydrous sodium sulfate. The solvent was then distilled off under reduced pressure. The resulting residue was subjected to silica gel column chromatography, eluted with hexane containing from 15 to 20% v/v ethyl acetate, yielding 2.1 g of a mixture of the title compounds.

Infrared Absorption Spectrum (liquid film) $\nu_{max}$cm$^{-1}$: 840, 1025, 1080, 1120, 3470.

Nuclear Magnetic Resonance Spectrum (CDCl$_3$) δ ppm: 4.77 (2H, broad singlet); 4.95–5.7 (4H, multiplet).

EXAMPLE 5

Mixture of 3-(1-t-butyldimethylsilyloxymethyl-5-acetoxypentyl)-6β-[3α-(2-tetrahydropyranyloxy)-5(R),9-dimethyl-1,8-decadienyl]-7α-(2-tetrahydropyranyloxy)bicyclo[3.3.0]oct-2-ene and 3-(1-t-butyldimethylsilyloxymethyl-5-acetoxypentyl)-6β-[3-α-(2-tetrahydropyranyloxy)-5(R),9-dimethyl-1,8-decadienyl]-7α-(2-tetrahydropyranyloxy)bicyclo[3.3.-0]oct-3-ene 1.7 g of the mixture of 3-(1-t-butyldimethylsilyloxymethyl-5-hydroxypentyl)-6β-[3α-(2-tetrahydropyranyloxy)-5(R),9-dimethyl-1,8-decadienyl]-7α-(2-tetrahydropyranyloxy)bicyclo[3.3.0]oct-2-ene and its oct-3-ene isomer, prepared as described in Example 4, was dissolved in 6 ml of pyridine, and then 3 ml of acetic anhydride were added, and the mixture was left standing for 2 hours at room temperature. The reaction mixture was diluted with 100 ml of water, and subsequently shaken. The reaction mixture was then extracted with ethyl acetate, and the extract was washed with water, with dilute hydrochloric acid and then again with water and dried with anhydrous sodium sulfate. The solvent was distilled off under reduced pressure, yielding 1.8 g of a mixture of the title compounds.

Infrared Absorption Spectrum (liquid film) $\nu_{max}$cm$^{-1}$: 840, 1020, 1033, 1080, 1120, 1235, 1745.

Nuclear Magnetic Resonance Spectrum (CDCl$_3$) δ ppm: 2.03 (3H, singlet); 4.05 (2H, triplet).

EXAMPLE 6

Mixture of 3-(1-hydroxymethyl-5-acetoxypentyl)-6β-[3α-(2-tetrahydropyranyloxy)-5(R),9-dimethyl-1,8-decadienyl]-7α-(2-tetrahydropyranyloxy)bicyclo[3.3.0]-oct-2-ene and 3-(1-hydroxymethyl-5-acetoxypentyl)-6β-[3α-(2-tetrahydropyranyloxy)-5(R),9-dimethyl-1,8-decadienyl]-7α-(2-tetrahydropyranyloxy)bicyclo[3.3.0]oct-3-ene 1.8 g of the mixture of 3-(1-t-butyldimethylsilyloxymethyl-5-acetoxypentyl)-6β-[3α-(2-tetrahydropyranyloxy)-5(R),9-dimethyl-1,8-decadienyl]-7α-(2-tetrahydropyranyloxy)bicyclo[3.3.0]oct-2-ene and its oct-3-ene isomer, prepared as described in Example 5, was dissolved in 30 ml of tetrahydrofuran, and 4.9 ml of tetrabutylammonium fluoride (as a 1M solution in tetrahydrofuran) were added. The reaction mixture was stirred for 2 hours at room temperature and then diluted with 150 ml of water. It was then extracted with ethyl acetate. The extract was washed with water and dried with anhydrous sodium sulfate. The solvent was distilled off under reduced pressure, and the resulting residue was subjected to silica gel column chromatography, eluted with hexane containing from 20 to 40% v/v ethyl acetate, yielding 1.53 g a mixture of the title compounds.

Infrared Absorption Spectrum (liquid film) $\nu_{max}$cm$^{-1}$: 980, 1020, 1033, 1075, 1120, 1130, 1240, 1743, 3480

Nuclear Magnetic Resonance Spectrum (CDCl$_3$) δ ppm: 2.03 (3H, singlet); 4.05 (2H, triplet); 4.68 (2H, broad singlet); 5.05–5.7 (4H, multiplet).

EXAMPLE 7

Mixture of 3-(1-methanesulfonyloxymethyl-5-acetoxypentyl)-6β-[3α-(2-tetrahydropyranyloxy)-5(R),9-dimethyl-1,8-decadienyl]-7α-(2-tetrahydropyranyloxy)bicyclo[3.3.-0]oct-2-ene and 3-(1-methanesulfonyloxymethyl-5-acetoxypentyl)-6β-[3α-(2-tetrahydropyranyloxy)-5(R),9-dimethyl-1,8-decadienyl]-7α-(2-tetrahydropyranyloxy)bicyclo[3.3.-0]oct-3-ene 1.53 g of the mixture of 3-(1-hydroxymethyl-5-acetoxypentyl)-6β-[3α-(2-tetrahydropyranyloxy)-5(R),9-dimethyl-1,8-decadienyl]-7α-(2-tetrahydropyranyloxy)bicyclo[3.3.0]oct-2-ene and its oct-3-ene isomer, prepared as described in Example 6, was dissolved in 30 ml of pyridine, and 0.28 ml of methanesulfonyl chloride was added. The mixture was stirred for 1 hour at room temperature. The reaction mixture was then diluted with 150 ml of water and extracted with ethyl acetate. The extract was washed with dilute hydrochloric acid and then with water and was dried with anhydrous sodium sulfate. The solvent was distilled off from the extract under reduced pressure, yielding 1.7 g of a mixture of the title compounds.

Infrared Absorption Spectrum (liquid film) $\nu_{max}$cm$^{-1}$: 980, 1025, 1035, 1180, 1240, 1360, 1743

Nuclear Magnetic Resonance Spectrum (CDCl$_3$) δ ppm: 2.03 (3H, singlet); 2.95 (3H, singlet); 4.68 (2H, broad singlet); 5.0–5.7 (4H, multiplet).

EXAMPLE 8

Mixture of 3-(1,1-methylene-5-acetoxypentyl)-6β-[3α-(2-tetrahydropyranyloxy)-5(R),9-dimethyl-1,8-decadienyl]-7α-(2-tetrahydropyranyloxy)bicyclo[3.3.0]oct-2-ene and 3-(1,1-methylene-5-acetoxypentyl)-6β-[3α-(2-tetrahydropyranyloxy)-5(R),9-dimethyl-1,8-decadienyl]-7α-(2-tetrahydropyranyloxy)bicyclo[3.3.0]oct-3-ene 1.7 g of the mixture of 3-(1-methanesulfonyloxymethyl-5-acetoxypentyl)-6β-[3α-(2-tetrahydropyranyloxy)-5(R),9-dimethyl-1,8-decadienyl]-7α-(2-tetrahydropyranyloxy)bicyclo[3.3.0]oct-2-ene and its oct-3-ene isomer (prepared as described in Example 7) was dissolved in 30 ml of hexamethylphosphoric triamide. 3 ml of 1,8-diazabicyclo[5.4.0]undec-7-ene and 1.0 g of sodium iodide were added to the mixture, which was then stirred at 90° C. for 1 hour. The reaction mixture was cooled and diluted with 100 ml of water. The diluted solution was extracted with ethyl acetate. The extract was washed with dilute hydrochloric acid and then with water and dried over anhydrous sodium sulfate. The solvent was distilled off under reduced pressure. The resulting residue was subjected to silica gel column chromatography, eluted with hexane containing 5 to 10% v/v ethyl acetate, to give 1.2 g of a mixture of the title compounds.

Infrared Absorption Spectrum (liquid film) $\nu_{max}$cm$^{-1}$: 1020, 1030, 1235, 1590, 1620, 1742.

Nuclear Magnetic Resonance Spectrum (CDCl$_3$) δ ppm: 0.92 (3H, doublet); 2.02 (3H, singlet); 4.83 (2H, broad singlet); 5.71 (1H, broad singlet).

EXAMPLE 9

3-(1,1-Methylene-5-hydroxypentyl)-6β-[3α-(2-tetrahydropyranyloxy)-5(R),9-dimethyl-1,8-decadienyl]-7α-(2-tetrahydropyranyloxy)bicyclo[3.3.0]oct-2-ene and 3-(1,1-methylene-5-hydroxypentyl)-6β-[3α-(2-tetrahydropyranyloxy)-5(R),9-dimethyl-1,8-decadienyl]-7α-(2-tetrahydropyranyloxy)bicyclo[3.3.0]oct-3-ene 1.25 g of the mixture of 3-(1,1-methylene-5-acetoxypentyl)-6β-[3α-(2-tetrahydropyranyloxy)-5(R),9-dimethyl-1,8-decadienyl]-7α-(2-tetrahydropyranyloxy)-bicyclo[3.3.0]oct-2-ene and its oct-3-ene isomer (prepared as described in Example 8) was dissolved in 30 ml of methanol. 0.25 g of anhydrous potassium carbonate was added to the mixture, and the mixture was stirred for 2.5 hours at room temperature. The reaction mixture was then diluted with 150 ml of water, and the solution was extracted with ethyl acetate. The extract was washed with water and dried over anhydrous sodium sulfate. The solvent was distilled off under reduced pressure and the resulting residue was subjected to medium pressure liquid chromatography using a Lobar (trade mark) column (size C), eluted with a 1:2 by volume mixture of ethyl acetate and hexane, yielding 0.68 g of the oct-2-ene compound and 0.51 g of the oct-3-ene compound.

Oct-2-ene compound:
Infrared Absorption Spectrum (liquid film) $\nu_{max}$cm$^{-1}$: 980, 1025, 1035, 1080, 1595, 1625, 3470.

Nuclear Magnetic Resonance Spectrum (CDCl$_3$) δ ppm: 0.95 (3H, doublet); 4.73 (2H, broad singlet); 4.90 (2H, singlet); 5.0–5.65 (3H, multiplet); 5.70 (1H, singlet).

Oct-3-ene compound:
Infrared Absorption Spectrum (liquid film) $\nu_{max}$cm$^{-1}$: 975, 1025, 1080, 1597, 1625, 3470.

Nuclear Magnetic Resonance Spectrum (CDCl$_3$) δ ppm: 0.95 (3H, multiplet); 4.73 (2H, multiplet); 4.90 (2H, singlet); 5.0–5.65 (3H, multiplet); 5.72 (1H, multiplet).

EXAMPLE 10

3-(1,1-Methylene-4-methoxycarbonylbutyl)-6β-[3α-(2-tetrahydropyranyloxy)-5(R),9-dimethyl-1,8-decadienyl]-7α-(2-tetrahydropyranyloxy)bicyclo[3.3.0]oct-2-ene 0.45 g of 3-(1,1-methylene-5-hydroxypentyl)-6β-[3α-(2-tetrahydropyranyloxy)-5(R),9-dimethyl-1,8-decadienyl]-7α-(2-tetrahydropyranyloxy)bicyclo[3.3.0]oct-2-ene) (prepared as described in Example 9) was dissolved in 1 ml of pyridine, and a solution of 0.1 g of chromic anhydride in 0.1 ml of water was added dropwise. The mixture was then stirred for 20 hours at room temperature. The reaction mixture was then diluted with a 1:1 by volume mixture of diethyl ether and benzene, and the precipitating insoluble matter was filtered off with a Celite filter aid. The filtrate was washed with dilute hydrochloric acid and then water, and was then dried with anhydrous sodium sulfate. The solvent was distilled off under reduced pressure. An ethereal solution of diazomethane was gradually added to the resulting residue, until the yellowish color of diazomethane no longer diappeared, and then the ether was distilled off, yielding 0.40 g of an oily residue. This residue was subjected to silica gel column chromatography, eluted with hexane containing from 10 to 15% v/v ethyl acetate, yielding 0.24 g of the title compound.

Infrared Absorption Spectrum (liquid film) $\nu_{max}$cm$^{-1}$: 975, 1020, 1030, 1075, 1130, 1200, 1590, 1620, 1740.

Nuclear Magnetic Resonance Spectrum (CDCl$_3$) δ ppm: 3.67 (3H, singlet); 4.72 (2H, broad singlet); 4.92 (2H, singlet); 5.0–5.68 (3H, multiplet); 5.71 (1H, broad singlet).

EXAMPLE 11

3-(1,1-Methylene-4-methoxycarbonylbutyl)-6β-[3α-hydroxy-5(R),9-dimethyl-1,8-decadienyl]-7α-hydroxybicyclo[3.3.0]oct-2-ene 0.22 g of 3-(1,1-methylene-4-methoxycarbonylbutyl)-6β-[3α-(2-tetrahydropyranyloxy)-5(R),9-dimethyl-1,8-decadienyl]-7α-(2-tetrahydropyranyloxy)bicyclo[3.3.0]oct-2-ene (prepared as described in Example 10) was dissolved in 4 ml of tetrahydrofuran, and 8 ml of acetic acid were added to the resulting solution. 15 ml of water were then added dropwise to the mixture at 50° C., whilst stirring, at such a pace as not to cause any white turbidity, and the mixture was stirred for a further 3 hours. The reaction mixture was then diluted with 150 ml of water and extracted with ethyl acetate. The extract was mixed with an aqueous solution of sodium bicarbonate to remove acetic acid, and then washed with a saturated aqueous solution of sodium chloride and dried over anhydrous sodium sulfate. The solvent was distilled off under reduced pressure. The resulting residue was subjected to silica gel column chromatography, eluted with hexane containing from 50 to 70% v/v ethyl acetate, yielding 0.15 g of the title compound.

Infrared Absorption Spectrum (liquid film) $\nu_{max}$cm$^{-1}$: 965, 1087, 1150, 1430, 1590, 1620, 1740, 3350.

Nuclear Magnetic Resonance Spectrum (CDCl$_3$) δ ppm: 0.94 (3H, doublet); 1.62 (3H, singlet); 1.69 (3H, singlet); 3.69 (3H, singlet); 4.16 (1H, multiplet); 4.93 (2H, singlet); 5.13 (1H, triplet); 5.6 (2H, multiplet); 5.74 (1H, singlet).

EXAMPLE 12

3-(1,1-Methylene-4-carboxybutyl)-6β-[3α-hydroxy-5(R),9-dimethyl-1,8-decadienyl]-7α-hydroxybicyclo[3.3.0]oct-2-ene 0.13 g of 3-(1,1-methylene-4-methoxycarbonylbutyl)-6β-[3α-hydroxy-5(R),9-dimethyl-1,8-decadienyl]-7α-hydroxybicyclo[3.3.0]oct-2-ene (prepared as described in Example 11) was dissolved in 7 ml of methanol, 3 ml of a 5% w/v aqueous solution of sodium hydroxide were added, and the mixture was stirred for 1 hour at room temperature. The reaction mixture was then diluted with 100 ml of water, acidified with dilute hydrochloric acid and extracted with ethyl acetate. The extract was washed with a saturated aqueous solution of sodium chloride and dried over anhydrous sodium sulfate. The solvent was distilled off under reduced pressure, yielding 0.12 g of the title compound.

Infrared Absorption Spectrum (liquid film) $\nu_{max}$cm$^{-1}$: 965, 1085, 1230, 1450, 1595, 1623, 1707, 2630, 3320.

Nuclear Magnetic Resonance Spectrum (CDCl$_3$+D$_2$O) δ ppm: 0.94 (3H, doublet); 1.61 (3H, singlet); 1.69 (3H, singlet); 3.13 (1H, multiplet); 3.77 (1H, multiplet); 4.18 (1H, multiplet); 4.94 (2H, singlet); 5.13 (1H, triplet, J=7.5 Hz); 5.55 (2H, multiplet); 5.74 (1H, singlet).

EXAMPLE 13

3-(1,1-Methylene-4-methoxycarbonylbutyl)-6β-[3α-(2-tetrahydropyranyloxy)-5(R),9-dimethyl-1,8-decadienyl]-7α-(2-tetrahydropyranyloxy)bicyclo[3.3.0]oct-3-ene 0.29 g of 3-(1,1-methylene-5-hydroxypentyl)-6β-[3α-(2-tetrahydropyranyloxy)-5(R),9-dimethyl-1,8-decadienyl]-7α-(2-tetrahydropyranyloxy)bicyclo[3.3.0]oct-3-ene (prepared as described in Example 9) was treated in the same manner as described in Example 10, yielding 0.18 g of the title compound.

Infrared Absorption Spectrum (liquid film) $\nu_{max}$cm$^{-1}$: 970, 1020, 1075, 1130, 1200, 1435, 1595, 1623, 1740.

Nuclear Magnetic Resonance Spectrum (CDCl$_3$) δ ppm: 0.95 (3H, multiplet); 3.67 (3H, singlet); 4.73 (2H, broad singlet); 4.90 (2H, singlet); 5.0–5.8 (4H, multiplet).

EXAMPLE 14

3-(1,1-Methylene-4-methoxycarbonylbutyl)-6β-[3α-hydroxy-5(R),9-dimethyl-1,8-decadienyl]-7α-hydroxybicyclo[3.3.0]oct-3-ene 0.16 g of 3-(1,1-methylene-4-methoxycarbonylbutyl)-6β-[3α-(2-tetrahydropyranyloxy)-5(R),9-dimethyl-1,8-decadienyl]-7α-(2-tetrahydropyranyloxy)bicyclo[3.3.0]oct-3-ene (prepared as described in Example 13) was treated in the same manner as described in Example 11, to obtain 0.11 g of the title compound.

Infrared Absorption Spectrum (liquid film) $\nu_{max}$cm$^{-1}$: 970, 1085, 1150, 1430, 1590, 1623, 1740, 3350.

Nuclear Magnetic Resonance Spectrum (CDCl$_3$) δ ppm: 0.92 (3H, doublet); 1.59 (3H, singlet); 1.65 (3H, singlet); 3.62 (3H, singlet); 4.12 (1H, multiplet); 4.84 (2H, singlet); 5.03 (1H, triplet, J=7.5 Hz); 5.43–5.63 (3H, multiplet).

EXAMPLE 15

3-(1,1-Methylene-4-carboxybutyl)-6β-[3α-hydroxy-5(R),9-dimethyl-1,8-decadienyl]-7α-hydroxybicyclo[3.3.0]oct-3-ene 0.11 g of 3-(1,1-methylene-4-methoxycarbonylbutyl)-6β-[3α-hydroxy-5(R),9-dimethyl-1,8-decadienyl]-7α-hydroxybicyclo[3.3.0]oct-3-ene (prepared as described in Example 14) was treated in the same manner as described in Example 12, to obtain 0.15 g of the title compound.

Infrared Absorption Spectrum (liquid film) $\nu_{max}$cm$^{-1}$: 970, 1080, 1240, 1450, 1590, 1623, 1705, 2630, 3320.

Nuclear Magnetic Resonance Spectrum (CDCl$_3$) δ ppm: 0.94 (3H, doublet); 1.61 (3H, singlet); 1.69 (3H, singlet); 3.78 (1H, multiplet); 4.23 (1H, multiplet); 4.95 (2H, singlet); 5.13 (1H, triplet, J=7.5 Hz); 5.63 (2H, multiplet); 5.77 (1H, singlet).

$[\alpha]^{24}$+100.2° (C=1.0, CHCl$_3$).

EXAMPLE 16

Mixture of
3-(1-methoxycarbonyl-5-benzyloxypentyl)-6β-[3α-(2-tetrahydropyranyloxy)-1-octenyl]-7α-(2-tetrahydropyranyloxy)bicyclo[3.3.0]oct-2-ene and 3-(1-methoxycarbonyl-5-benzyloxypentyl)-6β-[3α-(2-tetrahydropyranyloxy)-1-octenyl]-7α-(2-tetrahydropyranyloxy)bicyclo[3.3.0]oct-3-ene 1.97 g of 3,3-methoxycarbonylmethylene-6β-[3α-(2-tetrahydropyranyloxy)-1-octenyl]-7α-(2-tetrahydropyranyloxy)bicyclo[3.3.0]octane was treated in the same manner as described in Example 1, to obtain 2.15 g of a mixture of the title compounds.

Infrared Absorption Spectrum (liquid film) $\nu_{max}$cm$^{-1}$: 1020, 1075, 1740.

Nuclear Magnetic Resonance Spectrum (CDCl$_3$) δ ppm: 3.64 (3H, singlet); 4.45 (2H, singlet); 4.70 (2H, multiplet); 5.3–5.7 (3H, multiplet); 7.32 (5H, singlet).

EXAMPLE 17

Mixture of
3-(1-hydroxymethyl-5-benzyloxypentyl)-6β-[3α-(2-tetrahydropyranyloxy)-1-octenyl]-7α-(2-tetrahydropyranyloxy)bicyclo[3.3.0]oct-2-ene and 3-(1-hydroxymethyl-5-benzyloxypentyl)-6β-[3α-(2-tetrahydropyranyloxy)-1-octenyl]-7α-(2-tetrahydropyranyloxy)bicyclo[3.3.0]oct-3-ene 2.1 g of the mixture of 3-(1-methoxycarbonyl-5-benzyloxypentyl)-6β-[3α-(2-tetrahydropyranyloxy)-1-octenyl]-7α-(2-tetrahydropyranyloxy)bicyclo[3.3.0]oct-2-ene and its oct-3-ene isomer (prepared as described in Example 16) were treated in the same manner as described in Example 2, to obtain 2.0 g of a mixture of the title compounds.

Infrared Absorption Spectrum (liquid film) $\nu_{max}$cm$^{-1}$: 1025, 1080, 3490.

Nuclear Magnetic Resonance Spectrum (CDCl$_3$) δ ppm: 0.94 (3H, multiplet); 4.50 (2H, singlet); 4.70 (2H, singlet); 5.3–5.7 (3H, multiplet); 7.36 (5H, singlet).

EXAMPLE 18

Mixture of
3-(1-t-butyldimethylsilyloxymethyl-5-benzyloxypentyl)-6β-[3α-(2-tetrahydropyranyloxy)-1-octenyl]-7α-(2-tetrahydropyranyloxy)bicyclo[3.3.0]oct-2-ene and 3-(1-t-butyldimethylsilyloxymethyl-5-benzyloxypentyl)-6β-[3α-(2-tetrahydropyranyloxy)-1-octenyl]-7α-(2-tetrahydropyranyloxy)bicyclo[3.3.0]oct-3-ene 1.95 g of the mixture of 3-(1-hydroxymethyl-5-benzyloxypentyl)-6β-[3α-(2-tetrahydropyranyloxy)-1-octenyl]-7α-(2-tetrahydropyranyloxy)bicyclo[3.3.0]oct-2-ene and its oct-3-ene isomer (prepared as described in Example 17) was treated in the same manner as described in Example 3, to obtain 2.32 g of a mixture of the title compounds.

Infrared Absorption Spectrum (liquid film) $\nu_{max}$cm$^{-1}$: 1020, 1075.

Nuclear Magnetic Resonance Spectrum (CDCl$_3$) δ ppm: 0.88 (9H, singlet); 4.50 (2H, singlet); 4.73 (2H, multiplet); 5.2–5.8 (3H, multiplet); 7.36 (5H, singlet).

EXAMPLE 19

Mixture of
3-(1-t-butyldimethylsilyloxymethyl-5-hydroxypentyl)-6β-[3α-(2-tetrahydropyranyloxy)-1-octenyl]-7α-(2-tetrahydropyranyloxy)bicyclo[3.3.0]oct-2-ene and 3-(1-t-butyldimethylsilyloxymethyl-5-hydroxypentyl)-6β-[3α-(2-tetrahydropyranyloxy)-1-octenyl]-7α-(2-tetrahydropyranyloxy)bicyclo[3.3.0]oct-3-ene 2.28 g of the mixture of 3-(1-t-butyldimethylsilyloxymethyl-5-benzyloxypentyl)-6β-[3α-(2-tetrahydropyranyloxy)-1-octenyl]-7α-(2-tetrahydropyranyloxy)bicyclo[3.3.0]oct-2-ene and its oct-3-ene isomer (prepared as described in Example 18) were treated in the same manner as described in Example 4, to obtain 1.72 g of a mixture of the title compounds.

Infrared Absorption Spectrum (liquid film) $\nu_{max}$cm$^{-1}$: 840, 980, 1020, 1080, 1120, 1255, 3480.

Nuclear Magnetic Resonance Spectrum (CDCl$_3$) δ ppm: 0.88 (9H, singlet); 4.74 (2H, multiplet); 5.2–5.8 (3H, multiplet).

EXAMPLE 20

Mixture of
3-(1-t-butyldimethylsilyloxymethyl-5-acetoxypentyl)-6β-[3α-tetrahydropyranyloxy)-1-octenyl]-7α-(2-tetrahydropyranyloxy)bicyclo[3.3.0]oct-2-ene and 3-(1-t-butyldimethylsilyloxymethyl-5-acetoxypentyl)-6β-[3α-(2-tetrahydropyranyloxy)-1-octenyl]-7α-(2-tetrahydropyranyloxy)bicyclo[3.3.0]oct-3-ene 1.69 g of the mixture of 3-(1-t-butyldimethylsilyloxymethyl-5-hydroxypentyl)-6β-[3α-(2-tetrahydropyranyloxy)-1-octenyl]-7α-(2-tetrahydropyranyloxy)bicyclo[3.3.0]oct-2-ene and its oct-3-ene isomer (prepared as described in Example 19) was treated in the same manner as described in Example 5, to obtain 1.80 g of a mixture of the title compounds.

Infrared Absorption Spectrum (liquid film) $\nu_{max}$cm$^{-1}$: 840, 980, 1020, 1030, 1080, 1120, 1230, 1745.

Nuclear Magnetic Resonance Spectrum (CDCl$_3$) δ ppm: 0.90 (9H, singlet); 2.03 (3H, singlet); 4.05 (2H, triplet, J=6 Hz); 4.74 (2H, multiplet); 5.3–5.8 (3H, multiplet).

EXAMPLE 21

Mixture of
3-(1-hydroxymethyl-5-acetoxypentyl)-6β-[3α-(2-tetrahydropyranyloxy)-1-octenyl]-7α-(2-tetrahydropyranyloxy)bicyclo[3.3.0]oct-2-ene and 3-(1-hydroxymethyl-5-acetoxypentyl)-6β-[3α-(2-tetrahydropyranyloxy)-1-octenyl]-7α-(2-tetrahydropyranyloxy)bicyclo[3.3.0]oct-3-ene 1.83 g of the mixture of 3-(1-t-butyldimethylsilyloxymethyl-5-acetoxypentyl)-6β-[3α-(2-tetrahydropyranyloxy)-1-octenyl]-7α-(2-tetrahydropyranyloxy)bicyclo[3.3.0]oct-2-ene and its oct-3-ene isomer (prepared as described in Example 20) were treated in the same manner as described in Example 6, to obtain 1.50 g of a mixture of the title compounds.

Infrared Absorption Spectrum (liquid film) $\nu_{max}$cm$^{-1}$: 980, 1020, 1030, 1745, 3480.

Nuclear Magnetic Resonance Spectrum (CDCl$_3$) δ ppm: 0.88 (3H, multiplet); 2.03 (3H, singlet); 4.05 (2H, triplet, J=6 Hz); 4.70 (2H, multiplet); 5.2–5.7 (3H, multiplet).

EXAMPLE 22

Mixture of
3-(1-methanesulfonyloxymethyl-5-acetoxypentyl)-6β-[3α-(2-tetrahydropyranyloxy)-1-octenyl]-7α-(2-tetrahydropyranyloxy)bicyclo[3.3.0]oct-2-ene and 3-(1-methanesulfonyloxymethyl-5-acetoxypentyl)-6β-[3α-(2-tetrahydropyranyloxy)-1-octenyl]-7α-(2-tetrahydropyranyloxy)bicyclo[3.3.0]oct-3-ene 1.55 g of the mixture of 3-(1-hydroxymethyl-5-acetoxypentyl)-6β-[3α-(2-tetrahydropyranyloxy)-1-octenyl]-7α-(2-tetrahydropyranyloxy)bicyclo[3.3.0]oct-2-ene and its oct-3-ene isomer (prepared as described in Example 21) was treated in the same manner as described in Example 7, to obtain 1.75 g of a mixture of the title compounds.

Infrared Absorption Spectrum (liquid film) $\nu_{max}$cm$^{-1}$: 975, 1020, 1030, 1740.

Nuclear Magnetic Resonance Spectrum (CDCl$_3$) δ ppm: 0.86 (3H, multiplet); 2.03 (3H, singlet); 2.97 (3H, singlet); 4.73 (3H, multiplet); 5.3–5.7 (3H, multiplet).

EXAMPLE 23

Mixture of
3-(1,1-methylene-5-acetoxypentyl)-6β-[3α-(2-tetrahydropyranyloxy)-1-octenyl]-7α-(2-tetrahydropyranyloxy)bicyclo[3.3.0]oct-2-ene and 3-(1,1-methylene-5-acetoxypentyl)-6β-[3α-(2-tetrahydropyranyloxy)-1-octenyl]-7α-(2-tetrahydropyranyloxy)bicyclo[3.3.0]oct-3-ene 1.75 g of the mixture of 3-(1-methanesulfonyloxymethyl-5-acetoxypentyl)-6β-[3α-(2-tetrahydropyranyloxy)-1-octenyl]-7α-(2-tetrahydropyranyloxy)bicyclo[3.3.0]oct-2-ene and its oct-3-ene isomer (prepared as described in Example 22) was treated in the same manner as described in Example 8, to obtain 1.33 g of a mixture of the title compounds.

Infrared Absorption Spectrum (liquid film) $\nu_{max}$cm$^{-1}$: 980, 1020, 1030, 1080, 1135, 1240, 1595, 1625, 1745.

Nuclear Magnetic Resonance Spectrum (CDCl$_3$) δ ppm: 0.89 (3H, triplet); 2.03 (3H, singlet); 4.90 (2H, singlet); 5.2–5.8 (3H, multiplet).

EXAMPLE 24

3-(1,1-Methylene-5-hydroxypentyl)-6β-[3α-(2-tetrahydropyranyloxy)-1-octenyl]-7α-(2-tetrahydropyranyloxy)bicyclo[3.3.0]oct-2-ene and 3-(1,1-methylene-5-hydroxypentyl)-6β-[3α-(2-tetrahydropyranyloxy)-1-octenyl]-7α-(2-tetrahydropyranyloxy)bicyclo[3.3.0]oct-3-ene 1.35 g of the mixture of 3-(1,1-methylene-5-acetoxypentyl)-6β-[3α-(2-tetrahydropyranyloxy)-1-octenyl]-7α-(2-tetrahydropyranyloxy)bicyclo[3.3.0]oct-2-ene and its oct-3-ene isomer (prepared as described in Example 23) was treated in the same manner as described in Example 9, to obtain 0.73 g of the oct-2-ene compound (with the higher polarity) and 0.54 g of the oct-3-ene compound (with the lower polarity).

Oct-2-ene compound:
Infrared Absorption Spectrum (liquid film) $\nu_{max}$cm$^{-1}$: 980, 1020, 1035, 1080, 1595, 1625, 3450.

Nuclear Magnetic Resonance Spectrum (CDCl$_3$) δ ppm: 0.90 (3H, multiplet); 3.10 (1H, multiplet); 4.73 (2H, broad singlet); 4.92 (2H, singlet); 5.2–5.8 (3H, multiplet).

Oct-3-ene compound:

Infrared Absorption Spectrum (liquid film) $\nu_{max}$cm$^{-1}$: 975, 1020, 1080, 1595, 1625, 3460.

Nuclear Magnetic Resonance Spectrum (CDCl$_3$) δ ppm: 0.90 (3H, multiplet); 4.74 (2H, broad singlet); 4.92 (2H, singlet); 5.2–5.8 (3H, multiplet).

EXAMPLE 25

3-(1,1-Methylene-4-methoxycarbonylbutyl)-6β-[3α-(2-tetrahydropyranyloxy)-1-octenyl]-7α-(2-tetrahydropyranyloxy)bicyclo[3.3.0]oct-2-ene 0.7 g of 3-(1,1-methylene-5-hydroxypentyl)-6β-[3α-(2-tetrahydropyranyloxy)-1-octenyl]-7α-(2-tetrahydropyranyloxy)bicyclo[3.3.0]oct-2-ene (prepared as described in Example 24) was treated in the same manner as described in Example 10, to obtain 0.4 g of the title compound.

Infrared Absorption Spectrum (liquid film) $\nu_{max}$cm$^{-1}$: 975, 1020, 1075, 1135, 1200, 1595, 1625, 1740.

Nuclear Magnetic Resonance Spectrum (CDCl$_3$) δ ppm: 0.85 (3H, multiplet); 3.67 (3H, singlet); 4.73 (2H, broad singlet); 4.92 (2H, singlet); 5.70 (1H, broad singlet).

EXAMPLE 26

3-(1,1-Methylene-4-methoxycarbonylbutyl)-6β-(3α-hydroxy-1-octenyl)-7α-hydroxybicyclo[3.3.0]oct-2-ene 0.36 g of 3-(1,1-methylene-4-methoxycarbonylbutyl)-6β-[3α-(2-tetrahydropyranyloxy)-1-octenyl]-7α-(2-tetrahydropyranyloxy)bicyclo[3.3.0]oct-2-ene (prepared as described in Example 25) was treated in the same manner as described in Example 11, and then the product was recrystallized from a mixture of ethyl acetate and hexane, to obtain 0.15 g of the title compound, melting at 69°–70° C.

Infrared Absorption Spectrum (Nujol-trademark-mull) $\nu_{max}$cm$^{-1}$: 970, 1065, 1180, 1210, 1590, 1620, 1730, 1745, 3440.

Nuclear Magnetic Resonance Spectrum (CDCl$_3$) δ ppm: 0.90 (3H, triplet); 3.10 (1H, multiplet); 3.68 (3H, singlet); 4.93 (2H, singlet); 5.57 (2H, multiplet); 5.74 (1H, broad singlet).

$[\alpha]^{23}$ −31.1° (C=1.0, CHCl$_3$).

EXAMPLE 27

3-(1,1-Methylene-4-carboxybutyl)-6β-(3α-hydroxy-1-octenyl)-7α-hydroxybicyclo[3.3.0]oct-2-ene 0.18 g of 3-(1,1-methylene-4-methoxycarbonylbutyl)-6β-(3α-hydroxy-1-octenyl)-7α-hydroxybicyclo[3.3.0]oct-2-ene (prepared as described in Example 26) was treated in the same manner as described in Example 12, and the product was then recrystallized from a mixture of ethyl acetate and hexane, to obtain 0.15 g of the title compound, melting at 78°–80° C.

Infrared Absorption Spectrum (Nujol mull) $\nu_{max}$cm$^{-1}$: 970, 1080, 1595, 1625, 1680, 1725, 1745, 2620, 3400.

Nuclear Magnetic Resonance Spectrum (CDCl$_3$) δ ppm: 0.90 (3H, triplet); 3.07 (1H, triplet); 3.6–4.2 (2H, multiplet); 4.94 (2H, singlet); 5.55 (2H, multiplet); 5.74 (1H, singlet).

$[\alpha]^{24}$ −33.4° (C=1.0, CDCl$_3$).

EXAMPLE 28

3-(1,1-Methylene-4-methoxycarbonylbutyl)-6β-[3α-(2-tetrahydropyranyloxy)-1-octenyl]-7α-(2-tetrahydropyranyloxy)bicyclo[3.3.0]oct-3-ene 0.52 g of 3-(1,1-methylene-5-hydroxypentyl)-6β-[3α-(2-tetrahydropyranyloxy)-1-octenyl]-7α-(2-tetrahydropyranyloxy)bicyclo[3.3.0]oct-3-ene (prepared as described in Example 24) was treated in the same manner as described in Example 10, to obtain 0.40 g of the title compound.

Infrared Absorption Spectrum (liquid film) $\nu_{max}$cm$^{-1}$: 975, 1020, 1075, 1595, 1625, 1740.

Nuclear Magnetic Resonance Spectrum (CDCl$_3$) δ ppm: 0.93 (3H, multiplet); 3.67 (3H, singlet); 4.73 (2H, multiplet); 4.70 (2H, singlet); 5.3–5.7 (3H, multiplet).

EXAMPLE 29

3-(1,1-Methylene-4-methoxycarbonylbutyl)-6β-(3α-hydroxy-1-octenyl)-7α-hydroxybicyclo[3.3.0]oct-3-ene 0.38 g of 3-(1,1-methylene-4-methoxycarbonylbutyl)-6β-[3α-(2-tetrahydropyranyloxy)-1-octenyl]-7α-(2-tetrahydropyranyloxy)bicyclo[3.3.0]oct-3-ene (prepared as described in Example 28) was treated in the same manner as described in Example 11, to obtain 0.25 g of the title compound.

Infrared Absorption Spectrum (liquid film) $\nu_{max}$cm$^{-1}$: 970, 1090, 1595, 1625, 1740, 3360.

Nuclear Magnetic Resonance Spectrum (CDCl$_3$) δ ppm: 0.90 (3H, triplet); 3.67 (3H, singlet); 4.94 (2H, singlet); 5.62 (2H, multiplet); 5.75 (1H, singlet).

$[\alpha]^{23}$ +121.0° (C=1.0, CHCl$_3$).

EXAMPLE 30

3-(1,1-Methylene-4-carboxybutyl)-6β-(3α-hydroxy-1-octenyl)-7α-hydroxybicyclo[3.3.0]oct-3-ene 0.23 g of 3-(1,1-methylene-4-methoxycarbonylbutyl)-6β-(3α-hydroxy-1-octenyl)-7α-hydroxybicyclo[3.3.0]oct-3-ene (prepared as described in Example 29) was treated in the same manner as described in Example 12, and the product was then recrystallized from a mixture of ethyl acetate and hexane, to obtain 0.20 g of the title compound, melting at 88°–89° C.

Infrared Absorption Spectrum (Nujol mull) $\nu_{max}$cm$^{1}$: 965, 1080, 1180, 1595, 1625, 1710, 1730, 3380.

Nuclear Magnetic Resonance Spectrum (CDCl$_3$) δ ppm: 0.88 (3H, triplet); 3.5–4.2 (2H, multiplet); 4.93 (2H, singlet); 5.58 (2H, multiplet); 5.75 (1H, singlet).

$[\alpha]^{24}$ +137.4° (C=1.0, CHCl$_3$).

EXAMPLE 31

3-(1,1-Methylene-5-hydroxypentyl)-6β-[3α-(2-tetrahydropyranyloxy)-4-methyl-1-octenyl]-7α-(2-tetrahydropyranyloxy)bicyclo[3.3.0]oct-2-ene and 3-(1,1-methylene-5-hydroxypentyl)-6β-[3α-(2-tetrahydropyranyloxy)-4-methyl-1-octenyl]-7α-(2-tetrahydropyranyloxy)bicyclo[3.3.0]oct-3-ene Using 3,3-methoxycarbonylmethylene-6β-[3α-(2-tetrahydropyranyloxy)-4-methyl-1-octenyl]-7α-(2-tetrahydropyranyloxy)bicyclo[3.3.0]octane (prepared following the procedures described in European Patent Publication No. 136779) as the starting material, the same reactions as described in Examples 1 through 9 are carried out in order, to obtain the title compound.

EXAMPLE 32

3-(1,1-Methylene-4-carboxybutyl)-6β-(3α-hydroxy-4-methyl-1-octenyl)-7α-hydroxybicyclo[3.3.0]oct-2-ene By subjecting 3-(1,1-methylene-5-hydroxypentyl)-6β-[3α-(2-tetrahydropyranyloxy)-4-methyl-1-octenyl]-7α-(2-tetrahydropyranyloxy)bicyclo[3.3.0]oct-2-ene (prepared as described in Example 31) to the same reactions as described in Examples 10, 11 and 12 in order, the title compound is obtained.

EXAMPLE 33

3-(1,1-Methylene-5-hydroxypentyl)-6β-[3α-(2-tetrahydropyranyloxy)-4,4-dimethyl-1-octenyl]-7α-(2-tetrahydropyranyloxy)bicyclo[3.3.0]oct-2-ene and 3-(1,1-methylene-5-hydroxypentyl)-6β-[3α-(2-tetrahydropyranyloxy)-4,4-dimethyl-1-octenyl]-7α-(2-tetrahydropyranyloxy)bicyclo[3.3.0]oct-3-ene Using 3,3-(methoxycarbonylmethylene)-6β-[3α-(2-tetrahydropyranyloxy)-4,4-dimethyl-1-octenyl]-7α-(2-tetrahydropyranyloxy)bicyclo[3.3.0]octane (prepared following the procedures described in European Patent Publication No. 136779) as the starting material, the same reactions as described in Examples 1 through 9 are carried out in order, to obtain the title compound.

EXAMPLE 34

3-(1,1-Methylene-4-carboxybutyl)-6β-(3α-hydroxy-4,4-dimethyl-1-octenyl)-7α-hydroxybicyclo[3.3.0]oct-2-ene By using 3-(1,1-methylene-5-hydroxypentyl)-6β-[3α-(2-tetrahydropyranyloxy)-4,4-dimethyl-1-octenyl]-7α-(2-tetrahydropyranyloxy)bicyclo[3.3.0]oct-2-ene (prepared as described in Example 33), the same reactions described in Examples 10, 11 and 12 are carried out in order, to obtain the title compound.

EXAMPLE 35

3-(1,1-Methylene-4-carboxybutyl)-6β-(3α-hydroxy-4,4-dimethyl-1,8-nonadienyl)-7α-hydroxybicyclo[3.3.0]oct-2-ene Using 3,3-(methoxycarbonylmethylene)-6β-[3α-(2-tetrahydropyranyloxy)-4,4-dimethyl-1,8-nonadienyl]-7α-(2-tetrahydropyranyloxy)bicyclo[3.3.0]octane (prepared following the procedures described in European Patent Publication No. 136779) as the starting material, the same reactions as described in the Examples 1 through 12 are carried out in order, to obtain the title compound.

EXAMPLE 36

3-(1,1-Methylene-4-carboxybutyl)-6β-(3α-hydroxy-4-methyl-1,7-octadienyl)-7α-hydroxybicyclo[3.3.0]oct-2-ene Using 3,3-(methoxycarbonylmethylene)-6β-[3α-(2-tetrahydropyranyloxy)-4-methyl-1,7-octadienyl]-7α-hydroxybicyclo[3.3.0]octane (prepared following the procedures described in European Patent Publication No. 136779) as the starting material, the same reactions as described in Examples 1 through 12 are carried out in order to obtain the title compound.

EXAMPLE 37

3-(1,1-Methylene-4-carboxybutyl)-6β-(3α-hydroxy-5α-methylnona-1-enyl)-7α-hydroxybicyclo[3.3.0]oct-2-ene Using 3,3-(methoxycarbonylmethylene)-6β-[3α-(2-tetrahydropyranyloxy)-5α-methylnona-1-enyl]-7α-(2-tetrahydropyranyloxy)bicyclo[3.3.0]oct-2-ene (prepared following the procedures described in European Patent Publication No. 136779) as the starting material, the same reactions as described in Examples 1 through 12 are carried out in order, to obtain the title compound.

EXAMPLE 38

Mixture of
3-(1-methoxycarbonyl-5-benzyloxypentyl)-6β-[3α-(2-tetrahydropyranyloxy)-3-cyclohexyl-1-propenyl]-7α-(2-tetrahydropyranyloxy)bicyclo[3.3.0]oct-2-ene and 3-(1-methoxycarbonyl-5-benzyloxypentyl)-6β-[3α-(2-tetrahydropyranyloxy)-3-cyclohexyl-1-propenyl]-7α-(2-tetrahydropyranyloxy)bicyclo[3.3.0]oct-3-ene By treating 2.7 g of 3,3-(methoxycarbonylmethylene)-6β-[3α-(2-tetrahydropyranyloxy)-3-cyclohexyl-1-propenyl]-7α-(2-tetrahydropyranyloxy)bicyclo[3.3.0]-octane (prepared following the procedures described in European Patent Publication No. 136779) in the same manner as described in Example 1, 3.4 g of the title compound were obtained.

Infrared Absorption Spectrum (liquid film) $\nu_{max}$cm$^{-1}$; 980, 1025, 1035, 1080, 1740.

Nuclear Magnetic Resonance Spectrum (CDCl$_3$) δ ppm: 3.65 (3H, singlet); 4.50 (2H, singlet); 5.3–5.7 (3H, multiplet); 7.34 (5H, singlet).

EXAMPLE 39

Mixture of 3-(1-hydroxymethyl-5-benzyloxypentyl)-6β-[3α-(2-tetrahydropyranyloxy)-3-cyclohexyl-1-propenyl]-7α-(2-tetrahydropyranyloxy)bicyclo[3.3.0]oct-2-ene and 3-(1-hydroxymethyl-5-benzyloxypentyl)-6β-[3α-(2-tetrahydropyranyloxy)-3-cyclohexyl-1-propenyl]-7α-(2-tetrahydropyranyloxy)bicyclo[3.3.0]oct-3-ene 3.3 g of the mixture of 3-(1-methoxycarbonyl-5-benzyloxypentyl)-6β-[3α-(2-tetrahydropyranyloxy)-3-cyclohexyl-1-propenyl]-7α-(2-tetrahydropyranyloxy)-bicyclo[3.3.0]oct-2-ene and its oct-3-ene isomer (prepared as described in Example 38) were treated in the same manner as described in Example 2, to obtain 3.1 g of a mixture of the title compounds.

Infrared Absorption Spectrum (liquid film) $\nu_{max}$cm$^{-1}$: 975, 1020, 1030, 1075, 3480.

Nuclear Magnetic Resonance Spectrum (CDCl$_3$) δ ppm: 4.50 (2H, singlet); 4.68 (2H, broad singlet); 5.3–5.7 (3H, multiplet); 7.34 (5H, singlet).

EXAMPLE 40

Mixture of
3-(1-t-butyldimethylsilyloxymethyl-5-benzyloxypentyl)-6β-[3α-(2-tetrahydropyranyloxy)-3-cyclohexyl-1-propenyl]-7α-(2-tetrahydropyranyloxy)bicyclo[3.3.0]oct-2-ene and 3-(1-t-butyldimethylsilyloxymethyl-5-benzyloxypentyl)-6β-[3α-(2-tetrahydropyranyloxy)-3-cyclohexyl-1-propenyl]-7α-(2-tetrahydropyranyloxy)bicyclo[3.3.0]oct-3-ene 3.1 g of the mixture of 3-(1-hydroxymethyl-5-benzyloxypentyl)-6β-[3α-(2-tetrahydropyranyloxy)-3-cyclohexyl-1-propenyl]-7α-(2-tetrahydropyranyloxy)-bicyclo[3.3.0]oct-2-ene and its oct-3-ene isomer (prepared as described in Example 39) were treated in the same manner as described in Example 3, to obtain 3.6 g of a mixture of the title compounds.

Infrared Absorption Spectrum (liquid film) $\nu_{max}$cm$^{-1}$: 980, 1025, 1035.

Nuclear Magnetic Resonance Spectrum (CDCl$_3$) δ ppm: 0.88 (9H, singlet); 4.50 (2H, singlet); 4.70 (2H, broad singlet); 5.1–5.7 (3H, multiplet); 7.36 (5H, singlet).

EXAMPLE 41

Mixture of
3-(1-t-butyldimethylsilyloxymethyl-5-hydroxypentyl)-6β-[3α-(2-tetrahydropyranyloxy)-3-cyclohexyl-1-propenyl]-7α-(2-tetrahydropyranyloxy)bicyclo[3.3.0]oct-2-ene and 3-(1-t-butyldimethylsilyloxymethyl-5-hydroxypentyl)-6β-[3α-(2-tetrahydropyranyloxy)-3-cyclohexyl-1-propenyl]-7α-(2-tetrahydropyranyloxy)bicyclo[3.3.0]oct-3-ene 3.6 g of the mixture of 3-(1-t-butyldimethylsilyloxymethyl-5-benzyloxypentyl)-6β-[3α-(2-tetrahydropyranyloxy)-3-cyclohexyl-1-propenyl]-7α-(2-tetrahydropyranyloxy)bicyclo[3.3.0]oct-2-ene and its oct-3-ene isomer (prepared as described in Example 40) were treated in the same manner as described in Example 4, to obtain 2.5 g of a mixture of the title compounds.

Infrared Absorption Spectrum (liquid film) $\nu_{max}$cm$^{-1}$: 980, 1020, 1030, 1080, 1120, 3480.

Nuclear Magnetic Resonance Spectrum (CDCl$_3$) δ ppm: 0.87 (9H, singlet); 4.70 (2H, multiplet); 5.3–5.7 (3H, multiplet).

EXAMPLE 42

Mixture of
3-(1-t-butyldimethylsilyloxymethyl-5-acetoxypentyl)-6β-[3α-(2-tetrahydropyranyloxy)-3-cyclohexyl-1-propenyl]-7α-(2-tetrahydropyranyloxy)bicyclo[3.3.0]oct-2-ene and 3-(1-t-butyldimethylsilyloxymethyl-5-acetoxypentyl)-6β-[3α-(2-tetrahydropyranyloxy)-3-cyclohexyl-1-propenyl]-7α-(2-tetrahydropyranyloxy)bicyclo[3.3.0]oct-3-ene 1.85 g of the mixture of 3-(1-t-butyldimethylsilyloxymethyl-5-hydroxypentyl)-6β-[3α-(2-tetrahydropyranyloxy)-3-cyclohexyl-1-propenyl]-7α-(2-tetrahydropyranyloxy)bicyclo[3.3.0]oct-2-ene and its oct-3-ene isomer (prepared as described in Example 41) was treated in the same manner as described in Example 5, to obtain 1.95 g of a mixture of the title compounds.

Infrared Absorption Spectrum (liquid film) $\nu_{max}$cm$^{-1}$: 835, 975, 1020, 1030, 1075, 1120, 1230, 1743.

Nuclear Magnetic Resonance Spectrum (CDCl$_3$) δ ppm: 0.88 (9H, singlet); 2.03 (3H, singlet); 4.07 (2H, triplet, J=6 Hz); 4.74 (2H, multiplet); 5.3–5.7 (3H, multiplet).

EXAMPLE 43

Mixture of 3-(1-hydroxymethyl-5-acetoxypentyl) 6β-[3α-(2-tetrahydropyranyloxy)-3-cyclohexyl-1-propenyl]-7α-(2-tetrahydropyranyloxy)bicyclo[3.3.0]oct-2-ene and 3-(1-hydroxymethyl-5-acetoxypentyl)-6β-[3α-(2-tetrahydropyranyloxy)-3-cyclohexyl-1-propenyl]-7α-(2-tetrahydropyranyloxy)bicyclo[3.3.0]oct-3-ene 1.9 g of the mixture of 3-(1-t-butyldimethysilyloxymethyl-5-acetoxypentyl)-6β-[3α-(2-tetrahydropyranyloxy)-3-cyclohexyl-1-propenyl]-7α-(2-tetrahydropyranyloxy)bicyclo[3.3.0]oct-2-ene and its oct-3-ene isomer (prepared as described in Example 42) was treated in the same manner as described in Example 6, to obtain 1.6 g of a mixture of the title compounds.

Infrared Absorption Spectrum (liquid film) $\nu_{max}$cm$^{-1}$: 975, 1020, 1030, 1075, 1120, 1130, 1240, 1740, 3470.

Nuclear Magnetic Resonance Spectrum (CDCl$_3$) δ ppm: 2.03 (3H, singlet); 4.06 (2H, triplet, J=6 Hz); 4.68 (2H, broad singlet); 5.3–5.7 (3H, multiplet).

EXAMPLE 44

Mixture of
3-(1-methanesulfonyloxymethyl-5-acetoxypentyl)-6β-[3α-(2-tetrahydropyranyloxy)-3-cyclohexyl-1-propenyl]-7α-(2-tetrahydropyranyloxy)bicyclo[3.3.0]oct-2-ene and 3-(1-methanesulfonyloxymethyl-5-acetoxypentyl)-6β-[3α-(2-tetrahydropyranyloxy)-3-cyclohexyl-1-propenyl]-7α-(2-tetrahydropyranyloxy)bicyclo[3.3.0]oct-3-ene 1.53 g of the mixture of 3-(1-hydroxymethyl-5-acetoxypentyl)-6β-[3α-(2-tetrahydropyranyloxy)-3-cyclohexyl-1-propenyl]-7α-(2-tetrahydropyranyloxy)bicyclo[3.3.0]oct-2-ene and its oct-3-ene isomer (prepared as described in Example 43) was treated in the same manner as described in Example 7, to obtain 1.7 g of a mixture of the title compounds.

Infrared Absorption Spectrum (liquid film) $\nu_{max}$cm$^{-1}$: 975, 1020, 1030, 1175, 1240, 1360, 1740.

Nuclear Magnetic Resonance Sectrum (CDCl$_3$) δ ppm: 2.03 (3H, singlet); 2.97 (3H, singlet); 4.70 (2H, broad singlet); 5.3–5.7 (3H, multiplet).

EXAMPLE 45

Mixture of
3-(1,1-methylene-5-acetoxypentyl)-6β-[3α-(2-tetrahydropyranyloxy)-3-cyclohexyl-1-propenyl]-7α-(2-tetrahydropyranyloxy)bicyclo[3.3.0]oct-2-ene and 3-(1,1-methylene-5-acetoxypentyl)-6β-[3α-(2-tetrahydropyranyloxy)-3-cyclohexyl-1-propenyl]-7α-(2-tetrahydropyranyloxy)bicyclo[3.3.0]oct-3-ene 1.8 g of the mixture of 3-(1-methanesulfonyloxymethyl-5-acetoxypentyl)-6β-[3α-(2-tetrahydropyranyloxy)-3-cyclohexyl-1-propenyl]-7α-(2-tetrahydropyranyloxy)bicyclo[3.3.0]oct-2-ene and its oct-3-ene isomer (prepared as described in Example 44) was treated in the same manner as described in Example 8, to obtain 1.43 g of a mixture of the title compounds.

Infrared Absorption Spectrum (liquid film) $\nu_{max}$cm$^{-1}$: 975, 1020, 1030, 1080, 1240, 1595, 1625, 1740.

Nuclear Magnetic Resonance Spectrum (CDCl$_3$) δ ppm: 2.03 (3H, singlet); 4.70 (2H, multiplet); 4.90 (2H, singlet); 5.2–5.8 (3H, multiplet).

EXAMPLE 46

3-(1,1-Methylene-5-hydroxypenyl)-6β-[3α-(2-tetrahydropyranyloxy)-3-cyclohexyl-1-propenyl]-7α-(2-tetrahydropranyloxy)bicyclo[3.3.0]oct-2-ene and 3-(1,1-methylene-5-hydroxypentyl)-6β-[3α-(2-tetrahydropyranyloxy)-3-cyclohexyl-1-propenyl]-7α-(2-tetrahydropyranyloxy)bicyclo[3.3.0]oct-3-ene 1.38 g of the mixture of 3-(1,1-methylene-5-acetoxypentyl)-6β-[3α-(2-tetrahydropyranyloxy)-3-cyclohexyl-1-propenyl[-7α-(2-tetrahydropyranyloxy)bicyclo[3.3.0]oct-2-ene and its oct-3-ene isomer (prepared as described in Example 45) was treated in the same manner as described in Example 9, to obtain 0.89 g of the oct-2-ene compound (an isomer with a higher polarity) and 0.38 g of the oct-3-ene compound (an isomer with a lower polarity).

Oct-2-ene compound:
Infrared Absorption Spectrum (liquid film) $\nu_{max}$cm$^{-1}$: 975, 1020, 1030, 1075, 1120, 1135, 1200, 1450, 1595, 1625, 3470.
Nuclear Magnetic Resonance Spectrum (CDCl$_3$) δ ppm: 4.72 (2H, multiplet); 4.92 (2H, singlet); 5.70 (1H, broad singlet).

Oct-3-ene compound:
Infrared Absorption Spectrum (liquid film) $\nu_{max}$cm$^{-1}$: 975, 1020, 1080, 1120, 1135, 1205, 1455, 1595, 1625, 3480.
Nuclear Magnetic Resonance Spectrum (CDCl$_3$) δ ppm: 4.70 (2H, multiplet); 4.90 (2H, singlet); 5.2–5.8 (3H, multiplet).

EXAMPLE 47

3-(1,1-Methylene-4-methoxycarbonylbutyl)-6β-[3α-(2-tetrahydropyranyloxy)-3-cyclohexyl-1-propenyl]-7α-(2-tetrahydropyranyloxy)bicyclo[3.3.0]oct-2-ene By treating 0.86 g of 3-(1,1-methylene-5-hydroxypentyl)-6β-[3α-(2-tetrahydropyranyloxy)-3-cyclohexyl-1-propenyl]-7α-(2-tetrahydropyranyloxy)bicyclo[3.3.-0]oct-2-ene (prepared as described in Example 46) in the same manner as described in Example 10, 0.54 g of the title compound was obtained.

Infrared Absorption Spectrum (liquid film) $\nu_{max}$cm$^{-1}$: 980, 1025, 1035, 1080, 1205, 1595, 1625, 1745.
Nuclear Magnetic Resonance Spectrum (CDCl$_3$) δ ppm: 3.67 (3H, singlet); 4.73 (2H, broad singlet); 4.93 (2H, singlet); 5.3–5.8 (3H, multiplet).

EXAMPLE 48

3-(1,1-Methylene-4-methoxycarbonylbutyl)-6β-(3α-hydroxy-3-cyclohexyl-1-propenyl)-7α-hydroxybicyclo[3.3.0]oct-2-ene By treating 0.51 g of 3-(1,1-methylene-4-methoxycarbonylbutyl)-6β-[3α-(2-tetrahydropranyloxy)-3-cyclohexyl-1-propenyl]-7α-(2-tetrahydropyranyloxy)-bicyclo[3.3.0]oct-2-ene (prepared as described in Example 47) in the same manner as described in Example 11 and then recrystallizing the product from a mixture of ethyl acetate and hexane, 0.20 g of the title compound, melting at 76°–78° C., was obtained.

Infrared Absorption Spectrum (Nujol mull) $\nu_{max}$cm$^{-1}$: 1590, 1620, 1720, 1735, 3460.
Nuclear Magnetic Resonance Spectrum (CDCl$_3$) δ ppm: 3.14 (1H, multiplet); 3.67 (3H, singlet); 3.6–3.9 (2H, multiplet); 4.94 (2H, singlet); 5.55 (2H, multiplet); 5.75 (1H, singlet).
[α]$^{24}$ −18.3° (C=1.0, CHCl$_3$).

EXAMPLE 49

3-(1,1-Methylene-4-carboxybutyl)-6β-(3α-hydroxy-3-cyclohexyl-1-propenyl)-7α-hydroxybicyclo[3.3.0]oct-2-ene By treating 0.25 g of 3-(1,1-methylene-4-methoxycarbonylbutyl)-6β-(3α-hydroxy-3-cyclohexyl-1-propenyl)-7α-hydroxybicyclo[3.3.0]oct-2-ene (prepared as described in Example 48) in the same manner as described in Example 12 and then recrystallizing the product from a mixture of ethyl acetate and hexane, 0.20 g of the title compound, melting at 60°–65° C., was obtained.

Infrared Absorption Spectrum (Nujol mull) $\nu_{max}$cm$^{-1}$: 980, 1080, 1595, 1625, 1710, 2670, 2730, 3280.
Nuclear Magnetic Resonance Spectrum (CDCl$_3$) δ ppm: 3.10 (1H, multiplet); 3.6–3.9 (2H, multiplet); 4.94 (2H, singlet); 5.55 (2H, multiplet); 5.75 (1H, singlet).
[α]$^{23}$ −22.6° (C=1.0, CHCl$_3$).

EXAMPLE 50

3-(1,1-Methylene-4-methoxycarbonylbutyl)-6β-[3α-(2-tetrahydropyranyloxy)-3-cyclohexyl-1-propenyl]-7α-(2-tetrahydropyranyloxy)bicyclo[3.3.0]oct-3-ene By treating 0.36 g of 3-(1,1-methylene-5-hydroxypentyl)-6β-[3α-(2-tetrahydropyranyloxy)-3-cyclohexyl-1-propenyl]-7α-(2-tetrahydropyranyloxy)bicyclo[3.3.-0]oct-3-ene compound (prepared as described in Example 46) in the same manner as described in Example 10, 0.30 g of the title compound was obtained.

Infrared Absorption Spectrum (liquid film) $\nu_{max}$cm$^{-1}$: 975, 1025, 1080, 1135, 1205, 1450, 1595, 1625, 1745.
Nuclear Magnetic Resonance Spectrum (CDCl$_3$) δ ppm: 3.67 (3H, singlet); 4.73 (2H, multiplet); 4.93 (2H, singlet); 5.3–5.9 (3H, multiplet).

EXAMPLE 51

3-(1,1-Methylene-4-methoxycarbonylbutyl)-6β-(3α-hydroxy-3-cyclohexyl-1-propenyl)-7α-hydroxybicyclo[3.3.0]oct-3-ene By treating 0.27 g of 3-(1,1-methylene-4-methoxycarbonylbutyl)-6β-[3α-(2-tetrahydropyranyloxy)-3-cyclohexyl-1-propenyl]-7α-(2-tetrahydropyranyloxy)-bicyclo[3.3.0]oct-3-ene (prepared as described in Example 50) in the same manner as described in Example 11 and then recrystallizing the product from a mixture of ethyl acetate and hexane, 0.13 g of the title compound, melting at 80°–82° C., was obtained.

Infrared Absorption Spectrum (Nujol mull) $\nu_{max}$cm$^{-1}$: 960, 1080, 1150, 1210, 1590, 1620, 1740, 3420.
Nuclear Magnetic Resonance Spectrum (CDCl$_3$) δ ppm: 3.67 (3H, singlet); 4.94 (2H, singlet); 5.6 (2H, multiplet); 5.76 (1H, broad singlet).
[α]$^{24}$ +137.8° (C=1.0, CHCl$_3$).

EXAMPLE 52

3-(1,1-Methylene-4-carboxybutyl)-6β-(3a-hydroxy-3-cyclohexyl-1-propenyl)-7α-hydroxybicyclo[3.3.0]oct-3-ene By treating 0.12 g of 3-(1,1-methylene-4-methoxycarbonylbutyl)-6β-(3α-hydroxy-3-cyclohexyl-1-propenyl)-

7α-hydroxybicyclo[3.3.0]oct-3-ene (prepared as described in Example 51) in the same manner as described in Example 12, and then recrystallizing the product from a mixture of ethyl acetate and hexane, 0.10 g of the title compound, melting at 102°–107° C., was obtained.

Infrared Absorption Spectrum (Nujol mull) $\nu_{max}$cm$^{-1}$: 970, 1595, 1625, 1690, 1710, 1750, 3280, 3400.

Nuclear Magnetic Resonance Spectrum (CDCl$_3$) δ ppm: 3.8 (2H, multiplet); 4.94 (2H, singlet); 5.6 (2H, multiplet); 5.76 (1H, singlet).

$[\alpha]^{23}$ +141.7° (C=1.0, CHCl$_3$).

EXAMPLE 53

3-(1,1-Methylene-4-formylbutyl)-6β-(3α-hydroxy-3-cyclohexyl-1-propenyl)bicyclo[3.3.0]oct-2-ene 241 mg of 3-(1,1-methylene-5-hydroxypentyl)-6β-[3α-(2-tetrahydropyranyloxy)-3-cyclohexyl-1-propenyl]-7α-(2-tetrahydropyranyloxy)bicyclo[3.3.0]oct-2-ene (prepared as described in Example 46) were dissolved in 3 ml of dimethyl sulfoxide, and then 0.7 ml of triethylamine was added. 3 ml of a solution of 730 mg of a complex of pyridine and sulfur trioxide in dimethyl sulfoxide were added dropwise to this mixture at room temperature and with stirring. The stirring was continued for 30 minutes, and then the solution was poured into ice-water. The resulting solution was extracted with ethyl acetate. The extract was washed with a saturated aqueous solution of sodium chloride, cold 1% w/v hydrochloric acid, a dilute aqueous solution of sodium bicarbonate and a saturated aqueous solution of sodium chloride, in that order, and then dried over anhydrous sodium sulfate. On distilling off the solvent, 239 mg of an oily aldehyde compound [Infrared Absorption Spectrum (liquid film) $\nu_{max}$cm$^{-1}$: 2720, 1717] was obtained. By treating this aldehyde compound in the same manner as described in Example 11, 103 mg of the title compound were obtained.

Infrared Absorption Spectrum (CHCl$_3$)$\nu_{max}$cm$^{-1}$: 970, 1590, 1620, 1718, 3350.

EXAMPLE 54

3-(1,1-Methylene-4-carboxybutyl)-6β-(3α-hydroxy-4-cyclopentyl-1-butenyl)-7α-hydroxybicyclo[3.3.0]oct-2-ene Using 3,3-(methoxycarbonylmethylene)-6β-[3α-(2-tetrahydropyranyloxy)-4-cyclopentyl-1-butenyl]-7α-(2-tetrahydropyranyloxy)bicyclo[3.3.0]octane as the starting material, the same reactions as described in Examples 1 through 12 are conducted to give the title compound.

EXAMPLE 55

3-(1,1-Methylene-4-carboxybutyl)-6β-(3α-hydroxy-4-phenoxy-1-butenyl)-7α-hydroxybicyclo[3.3.0]oct-2-ene Using 3,3-(methoxycarbonylmethylene)-6β-[3α-(2-tetrahydropyranyloxy)-4-phenoxy-1-butenyl]-7α-(2-tetrahydropyranyloxy)bicyclo[3.3.0]octane as the starting material, the same reactions as described in Examples 1 through 12 were conducted in order, yielding the title compound.

Infrared Absorption Spectrum (CHCl$_3$) $\nu_{max}$cm$^{-1}$: 956, 1230, 1595, 1600, 1624, 1704, 3320.

EXAMPLE 56

Mixture of 3-(1-methoxycarbonyl-2-benzyloxyethyl)-6β-[3α-(2-tetrahydropyranyloxy)-5(R),9-dimethyl-1,8-decadienyl]-7α-(2-tetrahydropyranyloxy)bicyclo[3.3.0]oct-2-ene and 3-(1-methoxycarbonyl-2-benzyloxyethyl)-6β-[3α-(2-tetrahydropyranyloxy)-5(R),9-dimethyl-1,8-decadienyl]-7α-(2-tetrahydropyranyloxy)bicyclo[3.3.0]oct-3-ene 2.74 ml of dicyclohexylamine were dissolved in 50 ml of anhydrous tetrahydrofuran, and the solution was cooled down to −78° C. 8.38 ml of a 15% w/w solution of butyllithium in hexane were added dropwise, and the mixture was stirred for 10 minutes. 2.3 ml of hexamethylphosphoric triamide were added dropwise to this solution, and the mixture was stirred for 10 minutes. 5.0 g of 3,3-(methoxycarbonylmethylene)-6β-[3α-(2-tetrahydropyranyloxy)-5(R),9-dimethyl-1,8-decadienyl]-7α-(2-tetrahydropyranyloxy)bicyclo[3.3.0]octane was dissolved in 10 ml of tetrahydrofuran, and this solution was added dropwise to the above-mentioned mixture. The mixture was stirred for 10 minutes at −78° C. 1.91 ml of monochloromethyl benzyl ether was dissolved in 5 ml of tetrahydrofuran, and this solution was added dropwise to the above-mentioned solution. The mixture was stirred for 30 minutes at −30° to −25° C. 5 ml of a saturated aqueous solution of ammonium chloride were added to the reaction product, and the mixture was stirred for 10 minutes. The resulting solution was restored to room temperature, diluted with 500 ml of water and extracted with ethyl acetate. The extract was washed with water, dilute hydrochloric acid, and then water, in that order, and dried over anhydrous sodium sulfate. The solvent was distilled off under reduced pressure. The resulting residue was subjected to silica gel column chromatography, eluted with hexane containing from 15 to 20% v/v ethyl acetate, giving 3.0 g of the title compound.

Infrared Absorption Spectrum (liquid film) $\nu_{max}$cm$^{-1}$: 975, 1020, 1030, 1080, 1120, 1200, 1743.

Nuclear Magnetic Resonance Spectrum (CDCl$_3$) δ ppm: 3.70 (3H, singlet); 4.55 (2H, singlet); 4.70 (2H, broad singlet); 5.15 (1H, triplet, J=7.5 Hz); 5.35–5.7 (3H, multiplet); 7.36 (5H, singlet).

EXAMPLE 57

Mixture of
3-(1-hydroxymethyl-2-benzyloxyethyl)-6β-[3α-(2-tetrahydropyranyloxy)-5(R),9-dimethyl-1,8-decadienyl]-7α-(2-tetrahydropyranyloxy)bicyclo[3.3.0]oct-2-ene and 3-(1-hydroxymethyl-2-benzyloxyethyl)-6β-[3α-(2-tetrahydropyranyloxy)-5(R),9-dimethyl-1,8-decadienyl]-7α-(2-tetrahydropyranyloxy)bicyclo[3.3.0]oct-3-ene A solution of 3.1 g of the mixture of 3-(1-methoxycarbonyl-2-benzyloxyethyl)-6β-[3α-(2-tetrahydropyranyloxy)-5(R),9-dimethyl-1,8-decadienyl]-7α-(2-tetrahydropyranyloxy)bicyclo[3.3.0]oct-2-ene and its oct-3-ene isomer (prepared as described in Example 56) in 10 ml of tetrahydrofuran was added dropwise, whilst ice-cooling, to a suspension of 0.3 g of lithium aluminum hydride in 50 ml of anhydrous tetrahydrofuran, and the mixture was stirred for 10 minutes. Subsequently, 1.2 ml of a 5% w/v aqueous solution of sodium hydroxide was added dropwise to the mixture, which was then stirred for a further 1.5 hours at room temperature. The precipitating insoluble matter was removed by filtration through a Celite filter aid, and the filtrate was condensed to obtain 2.9 g of the title compound.

Infrared Absorption Spectrum (liquid film) $v_{max}$cm$^{-1}$: 980, 1020, 1030, 1075, 1120, 1200, 1450, 3470.

Nuclear Magnetic Resonance Spectrum (CDCl$_3$) δ ppm: 0.95 (3H, multiplet); 4.53 (2H, singlet); 4.70 (2H, broad singlet); 5.0–5.9 (4H, multiplet); 7.36 (5H, singlet).

EXAMPLE 58

Mixture of
3-(1-benzyloxymethyl-2-carboxymethoxyethyl)-6β-[3α-(2-tetrahydropyranyloxy)-5(R),9-dimethyl-1,8-decadienyl]-7α-(2-tetrahydropyranyloxy)bicyclo[3.3.0]oct-2-ene and 3-(1-benzyloxymethyl-2-carboxymethoxyethyl)-6β-[3α-(2-tetrahydropyranyloxy)-5(R),9-dimethyl-1,8-decadienyl]-7α-(2-tetrahydropyranyloxy)bicyclo[3.3.0]oct-3-ene 2.9 g of the mixture of 3-(1-hydroxymethyl-2-benzyloxyethyl)-6β-[3α-(2-tetrahydropyranyloxy)-5(R),9-dimethyl-1,8-decadienyl]-7α-(2-tetrahydropyranyloxy)bicyclo[3.3.0]oct-2-ene and its oct-3-ene isomer (prepared as described in Example 57) were dissolved in 12 ml of anhydrous tetrahydrofuran, and 3.8 ml of a 15% w/w solution of butyllithium in hexane were added dropwise, whilst ice-cooling and stirring. The mixture was stirred for 5 minutes, and then 6 ml of dimethylformamide, 0.69 g of the lithium salt of monochloroacetic acid, 6 ml of dimethyl sulfoxide and 2.05 g anhydrous sodium iodide were added in this order, and the mixture was carefully heated up to 40° C., and then stirred for 16 hours at room temperature. The reaction product was diluted with 150 ml of ice-water, acidified with hydrochloric acid and then extracted with ethyl acetate. The extract was washed with water and dried over anhydrous sodium sulfate. The solvent was then distilled off under reduced pressure, and the residue was subjected to silica gel column chromatography, eluted with hexane containing from 20 to 80% v/v ethyl acetate, yielding 2.2 g of the title compound.

Infrared Absorption Spectrum (liquid film) $v_{max}$cm$^{-1}$: 980, 1020, 1130, 1735, 1760, 3200.

Nuclear Magnetic Resonance Spectrum (CDCl$_3$) δ ppm: 4.08 (2H, singlet); 4.53 (2H, singlet); 5.15 (1H, triplet, J=7.5 Hz); 5.3–5.7 (3H, multiplet); 7.36 (5H, singlet); 8.73 (1H, broad singlet).

EXAMPLE 59

Mixture of
3-(1-hydroxymethyl-2-methoxycarbonylmethoxyethyl)-6β-[3α-(2-tetrahydropyranyloxy)-5(R),9-dimethyl-1,8-decadienyl]-7α-(2-tetrahydropyranyloxy)bicyclo[3.3.0]oct-2-ene and 3-(1-hydroxymethyl-2-methoxycarbonylmethoxyethyl)-6β-[3α-(2-tetrahydropyranyloxy)-5(R),9-dimethyl-1,8-decadienyl]-7α-(2-tetrahydropyranyloxy)bicyclo[3.3.0]oct-3-ene 2.2 g of the mixture of 3-(1-benzyloxymethyl-2-carboxymethoxyethyl)-6β-[3α-(2-tetrahydropyranyloxy)-5(R),9-dimethyl-1,8-decadienyl]-7α-(2-tetrahydropyranyloxy)bicyclo[3.3.0]oct-2-ene and its oct-3-ene isomer (prepared as described in Example 58) were treated in the same manner as described in Example 4 (dilution with water in the post-treatment and acidification with hydrochloric acid, followed by extraction). An ethereal solution of diazomethane was added to the resulting residue until the yellowish color of diazomethane no longer disappeared. Diethyl ether was then distilled off, and the residue was subjected to silica gel column chromatography, eluted with hexane containing from 30 to 45% v/v ethyl acetate, to obtain 1.1 g of the title compound.

Infrared Absorption Spectrum (liquid film) $v_{max}$cm$^{-1}$: 980, 1020, 1030, 1075, 1130, 1200, 1440, 1740, 1760, 3500.

Nuclear Magnetic Resonance Spectrum (CDCl$_3$) δ ppm: 3.70 (3H, singlet); 4.13 (2H, singlet); 4.73 (2H, broad singlet); 5.15 (1H, triplet, J=7.5 Hz); 5.4–5.7 (3H, multiplet).

EXAMPLE 60

3-(1-Methanesulfonyloxymethyl-2-methoxycarbonylmethoxyethyl)-6β-[3α-(2-tetrahydropyranyloxy)-5(R),9-dimethyl-1,8-decadienyl]-7α-(2-tetrahydropyranyloxy)bicyclo[3.3.0]oct-2-ene and 3-(1-methanesulfonyloxymethyl-2-methoxycarbonylmethoxyethyl)-6β-[3α-(2-tetrahydropyranyloxy)-5(R),9-dimethyl-1,8-decadienyl]-7α-(2-tetrahydropyranyloxy)bicyclo[3.3.0]oct-3-ene By treating 0.87 g of the mixture of 3-(1-hydroxymethyl-2-methoxycarbonylmethoxyethyl)-6β-[3α-(2-tetrahydropyranyloxy)-5(R),9-dimethyl-1,8-decadienyl]-7α-(2-tetrahydropyranyloxy)bicyclo[3.3.0]oct-2-ene and its oct-3-ene isomer (prepared as described in Example 59) in the same manner as described in Example 7, 0.97 g of the title compound was obtained.

Infrared Absorption Spectrum (liquid film) $v_{max}$cm$^{-1}$: 980, 1025, 1140, 1180, 1360, 1760.

Nuclear Magnetic Resonance Spectrum (CDCl$_3$) δ ppm: 3.0 (3H, singlet); 3.77 (3H, singlet); 4.10 (2H, singlet); 4.39 (2H, doublet, J=6 Hz); 4.73 (2H, broad singlet); 5.0–5.7 (4H, multiplet).

EXAMPLE 61

3-(1,1-Methylene-2-methoxycarbonylmethoxyethyl)-6β-[3α-(2-tetrahydropyranyloxy)-5(R),9-dimethyl-1,8-decadienyl]-7α-(2-tetrahydropyranyloxy)bicyclo[3.3.0]oct-2-ene and 3-(1,1-methylene-2-methoxycarbonylmethoxyethyl)-6β-[3α-(2-tetrahydropyranyloxy)-5(R),9-dimethyl-1,8-decadienyl]-7α-(2-tetrahydropyranyloxy)bicyclo[3.3.0]oct-3-ene By treating 0.95 g of the mixture of 3-(1-methanesulfonyloxy-2-methoxycarbonylmethoxyethyl)-6β-[3α-(2-tetrahydropyranyloxy)-5(R),9-dimethyl-1,8-decadienyl]-7α-(2-tetrahydropyranyloxy)bicyclo[3.3.0]oct-2-ene and its oct-3-ene isomer (prepared as described in Example 60) in the same manner as described in Example 8, 0.46 g of the oct-2-ene isomer and 0.25 g of the oct-3-ene isomer of the title compound were obtained and were separated by medium pressure liquid chromatography using a Lobar column (size B), eluted with a 1:3 by volume mixture of ethyl acetate and hexane.

Oct-2-ene compound:
Infrared Absorption Spectrum (liquid film) $v_{max}$cm$^{-1}$: 980, 1020, 1030, 1075, 1130, 1200, 1440, 1595, 1630, 1760.

Nuclear Magnetic Resonance Spectrum (CDCl$_3$) δ ppm: 0.95 (3H, multiplet); 3.77 (3H, singlet); 4.08 (2H, singlet); 4.30 (2H, singlet); 4.73 (2H, broad singlet); 5.12 (1H, singlet); 5.24 (1H, singlet); 5.88 (1H, broad singlet).

Oct-3-ene compound:

Infrared Absorption Spectrum (liquid film) $\nu_{max}$cm$^{-1}$: 975, 1025, 1080, 1135, 1205, 1440, 1745, 1760.

Nuclear Magnetic Resonance Spectrum (CDCl$_3$) δ ppm: 3.77 (3H, singlet); 4.10 (2H, singlet); 4.30 (2H, singlet); 5.10 (1H, singlet); 5.23 (1H, singlet); 5.88 (1H, broad singlet).

EXAMPLE 62

3-(1,1-Methylene-2-methoxycarbonylmethoxyethyl)-6β-[3α-hydroxy-5(R),9-dimethyl-1,8-decadienyl]-7α-hydroxybicyclo[3.3.0]oct-2-ene 0.43 g of 3-(1,1-methylene-2-methoxycarbonylmethoxyethyl)-6β-[3α-(2-tetrahydropyranyloxy)-5(R),9-dimethyl-1,8-decadienyl]-7α-(2-tetrahydropyranyloxy)-bicyclo[3.3.0]oct-2-ene prepared as described in Example 61) was dissolved in 7.5 ml of tetrahydrofuran, and 15 ml of acetic acid were added; the mixture was then stirred at 50° C. Whilst the stirring continued, 20 ml of water were slowly added dropwise at such a pace as not to cause white turbidity, and the stirring was then continued for a further 30 minutes. The reaction product was then diluted with 150 ml of water, and extracted with ethyl acetate. The extract was treated with an aqueous solution of sodium bicarbonate to remove the acetic acid, washed with a saturated aqueous solution of sodium chloride and then dried with anhydrous sodium sulfate. The solvent was distilled off under reduced pressure. The residue was subjected to silica gel column chromatography, eluted with hexane containing from 50 to 80% v/v ethyl acetate, to obtain 0.28 g of the title compound.

Infrared Absorption Spectrum (liquid film) $\nu_{max}$ cm$^{-1}$: 970, 1090, 1130, 1210, 1440, 1595, 1630, 1755, 3370.

Nuclear Magnetic Resonance Spectrum (CDCl$_3$) δ ppm: 0.94 (3H, doublet, J=6 Hz); 1.62 (3H, singlet); 1.68 (3H, singlet); 3.77 (3H, singlet); 4.10 (2H, singlet); 4.30 (2H, singlet); 5.10 (1H, singlet); 5.23 (1H, singlet); 5.57 (2H, multiplet); 5.90 (1H, singlet).

EXAMPLE 63

3-(1,1-Methylene-2-carboxymethoxyethyl)-6β-[3α-hydroxy-5(R),9-dimethyl-1,8-decadienyl]-7α-hydroxybicyclo[3.3.0]oct-2-ene By treating 0.26 g of 3-(1,1-methylene-2-methoxycarbonylmethoxyethyl)-6β-[3α-hydroxy-5(R),9-dimethyl-1,8-decadienyl]-7α-hydroxybicyclo[3.3.0]oct-2-ene (prepared as described in Example 62) in the same manner as described in Example 12, 0.25 g of the title compound was obtained.

Infrared Absorption Spectrum (liquid film) $\nu_{max}$cm$^{-1}$: 970, 1090, 1120, 1210, 1380, 1450, 1600, 1630, 1735 2630, 3350.

Nuclear Magnetic Resonance Spectrum (CDCl$_3$) δ ppm: 0.94 (3H doublet, J=6 Hz); 1.60 (3H, singlet); 1.68 (3H, singlet); 4.08 (2H, singlet); 4.32 (2H, singlet); 5.13 (1H, singlet); 5.26 (1H, singlet); 5.5 (2H, multiplet); 5.90 (1H, broad singlet).

[α]$^{25}$ −23.9° (C=1.0, CHCl$_3$).

EXAMPLE 64

3-(1,1-Methylene-2-methoxycarbonylmethoxyethyl)-6β-[3α-hydroxy-5(R),9-dimethyl-1,8-decadienyl]-7α-hydroxybicyclo[3.3.0]oct-3-ene By treating 0.22 g of 3-(1,1-methylene-2-methoxycarbonylmethoxyethyl)-6β-[3α-(2-tetrahydropyranyloxy)-5(R),9-dimethyl-1,8-decadienyl]-7α-(2-tetrahydropyranyloxy)bicyclo[3.3.0]oct-3-ene (prepared as described in Example 61) in the same manner as in the Example 62, 0.15 g of the title compound was obtained.

Infrared Absorption Spectrum (liquid film) $\nu_{max}$cm$^{-1}$: 970, 1090, 1130, 1210, 1440, 1600, 1635, 1760, 3380.

Nuclear Magnetic Resonance Spectrum (CDCl$_3$) δ ppm: 0.94 (3H, doublet, J=6 Hz); 1.61 (3H, singlet); 1.68 (3H, singlet); 3.77 (3H, singlet); 4.10 (2H, singlet); 4.30 (2H, singlet); 5.13 (1H, singlet); 5.24 (1H, singlet); 5.64 (2H, multiplet); 5.90 (1H, singlet).

EXAMPLE 65

3-(1,1-Methylene-2-carboxymethoxyethyl)-6β-[3α-hydroxy-5(R),9-dimethyl-1,8-decadienyl]-7α-hydroxybicyclo[3.3.0]oct-3-ene By treating 0.12 g of 3-(1,1-methylene-2-methoxycarbonylmethoxyethyl)-6β-[3α-hydroxy-5(R),9-dimethyl-1,8-decadienyl]-7α-hydroxybicyclo[3.3.0]oct-3-ene (prepared as described in Example 64) in the same manner as described in Example 12, 0.11 g of the title compound was obtained.

Infrared Absorption Spectrum (liquid film) $\nu_{max}$cm$^{-1}$: 970, 1090, 1125, 1220, 1380, 1450, 1600, 1635, 1740, 2650, 3350.

Nuclear Magnetic Resonance Spectrum (CDCl$_3$) δ ppm: 0.93 (3H, doublet, J=6 Hz); 1.60 (3H, singlet); 1.68 (3H, singlet); 4.06 (2H, singlet); 4.30 (2H, singlet); 5.13 (1H, singlet); 5.23 (1H, singlet); 5.6 (2H, multiplet); 5.93 (1H, broad singlet).

[α]$^{25}$ +92.7° (C=1.0, CHCl$_3$).

EXAMPLE 66

3-(1,1-Methylene-2-carboxymethoxyethyl)-6β-(3α-hydroxy-4-methylnona-1,8-dienyl)-7α-hydroxybicyclo[3.3.0]oct-2-ene Using 3,3-(methoxycarbonylmethylene)-6β-[3α-(2-tetrahydropyranyloxy)-4-methylnona-1,8-dienyl]-7α-(tetrahydropyranyloxy)bicyclo[3.3.0]octane as the starting material, the same reactions as described in Examples 56 through 63 are conducted, to give the title compound.

EXAMPLE 67

3-(1,1-Methylene-2-carboxymethoxyethyl)-6β-(3α-hydroxy-4,4-dimethylnona-1,8-dienyl)-7α-hydroxybicyclo[3.3.0]oct-2-ene Using 3,3-(methoxycarbonylmethylene)-6β-[3α-(2-tetrahydropyranyloxy)-4,4-dimethylnona-1,8-dienyl]-7α-(tetrahydropyranyloxy)bicyclo[3.3.0]octane as the starting material, the same reactions as described in Examples 56 through 63 are conducted, to give the title compound.

EXAMPLE 68

3-(1,1-Methylene-2-carboxymethoxyethyl)-6β-(3α-hydroxy-1-octenyl)-7α-hydroxybicyclo[3.3.0]oct-2-ene Using 3,3-(methoxycarbonylmethylene)-6β-[3α-(2-tetrahydropyranyloxy)-1-octenyl]-7α-(2-tetrahydropyranyloxy)bicyclo[3.3.0]octane as the starting material, the same reactions as described in Examples 56 through 63 were conducted, to give the title compound, melting at 45°–47° C.

Infrared Absorption Spectrum (KBr) $\nu_{max}$cm$^{-1}$: 900, 970, 1090, 1125, 1630, 1730, 3400.

Nuclear Magnetic Resonance Spectrum (CDCl$_3$) δ ppm: 0.90 (3H, triplet); 3.10 (1H, multiplet); 4.07 (2H, singlet); 4.31 (2H, singlet); 5.12 (1H, singlet); 5.20 (1H, singlet); 5.55 (2H, multiplet); 5.90 (1H, singlet). $[\alpha]^{25} -32.5°$ (C=1.0, CHCl$_3$).

EXAMPLE 69

3-(1,1-Methylene-2-carboxymethoxyethyl)-6β-(3α-hydroxy-3-cyclohexyl-1-propenyl)-7α-hydroxybicyclo[3.3.0]oct-2-ene Using 3,3-(methoxycarbonylmethylene)-6β-[3α-(2-tetrahydropyranyloxy)-3-cyclohexyl-1-propenyl]-7α-(2-tetrahydropyranyloxy)bicyclo[3.3.0]octane as the starting material, the same reactions as conducted in Examples 56 through 63 are conducted, yielding the title compound.

EXAMPLE 70

3-(1,1-Methylene-2-carboxymethoxyethyl)-6β-(3α-hydroxy-4-phenoxy-1-butenyl)-7α-hydroxybicyclo[3.3.0]oct-2-ene Using 3,3-(methoxycarbonylmethylene)-6β-[3α-(2-tetrahyropyranyloxy)-4-phenoxy-1-butenyl]-7α-(2-tetrahydropyranyloxy)bicyclo[3.3.0]octane as the starting material, the same reactions as described in Examples 56 through 63 are conducted, yielding the title compound.

Infrared Absorption Spectrum (liquid film) $\nu_{max}$cm$^{-1}$: 1735.

EXAMPLE 71

3-(1,1-Methylene-2-methoxycarbonylmethoxyethyl)-6β-(3-oxo-5,9-dimethyl-1,8-decadienyl)-7α-(2-tetrahydropyranyloxy)bicyclo[3.3.0]oct-2-ene 88 mg of a 55% w/w suspension of sodium hydride in mineral oil was washed with hexane, and then 10 ml of tetrahydrofuran was added, followed by 750 mg of dimethyl 2-oxo-4,8-dimethyl-7-nonenylphosphonate, with ice cooling. The mixture was then stirred for 1 hour at room temperature. The mixture was then cooled with ice, after which 500 mg of 3-(1,1-methylene-2-methoxycarbonylmethoxyethyl)-6β-formyl-7α-hydroxybicyclo[3.3.0]oct-2-ene (prepared as described in Preparation 8) were added, and the mixture was allowed to react for 2 hours. At the end of this time, the reaction product was poured into ice-water and extracted with ethyl acetate. The extract was washed with water and dried over anhydrous sodium sulfate. The solvent of the extract was then distilled off. The resulting residue was purified by silica gel column chromatography, eluted with hexane containing from 20 to 30% v/v ethyl acetate, to give 527 mg of the title compound as an oil.

Infrared Absorption Spectrum (liquid film) $\nu_{max}$cm$^{-1}$: 1595, 1630, 1670, 1692, 1750.

EXAMPLE 72

3-(1,1-Methylene-2-methoxycarbonylmethoxyethyl)-6β-(3-hydroxy-5,9-dimethyl-1,8-decadienyl)-7α-(2-tetrahydropyranyloxy)bicyclo[3.3.0]oct-2-ene 510 mg of cerium chloride heptahydrate were dissolved in 5 ml of methanol, and 5 ml of a methanolic solution of 515 mg of 3-(1,1-methylene-2-methoxycarbonylmethoxyethyl)-6β-(3-oxo-5,9-dimethyl-1,8-decadienyl)-7α-(2-tetrahydropyranyloxy)bicyclo[3.3.0]oct-2-ene (prepared as described in Example 71) were added at 0°–5° C. 100 mg of sodium borohydride were added to this reaction mixture at 0°–3° C., with stirring, and the mixture was reacted with 30 minutes. At the end of this time, water was added to the reaction mixture, and the mixture was extracted with ethyl acetate. The extract was washed with water and dried over anhydrous sodium sulfate. The solvent was then distilled off. The resulting residue was purified by silica gel column chromatography, eluted with hexane containing from 20 to 30% v/v ethyl acetate, to give 501 mg of the title compound (a mixture of the 3α- and 3β-isomers) as an oil.

Infrared Absorption Spectrum (CHCl$_3$) $\nu_{max}$cm$^{-1}$: 1020, 1595, 1620, 1750, 3450.

EXAMPLE 73

3-(1,1-Methylene-2-methoxycarbonylmethoxyethyl)-6β-(3α-hydroxy-5,9-dimethyl-1,8-decadienyl)-7α-hydroxybicyclo[3.3.0]oct-2-ene and its 3β-hydroxy isomer 495 mg of 3-(1,1-methylene-2-methoxycarbonylmethoxyethyl)-6β-(3α/β-hydroxy-5,9-dimethyl-1,8-decadienyl)-7α-(2-tetrahydropyranyloxy)bicyclo[3.3.0]oct-2-ene (prepared as described in Example 72) were reacted in the same manner as described in the Example 11. From the portion with the higher polarity, eluted with hexane containing from 45 to 60% v/v ethyl acetate, 101 mg of the 3α-hydroxy compound were obtained; 70 mg of the 3β-hydroxy compound were obtained from the portion with the smaller polarity, eluted with hexane containing from 40 to 45% v/v ethyl acetate.

3β-Hydroxy compound:
Infrared Absorption Spectrum (liquid film) $\nu_{max}$cm$^{-1}$: 970, 1090, 1130, 1210, 1440, 1595, 1630, 1755, 3370.

3α-Hydroxy compound:
Infrared Absorption Spectrum (liquid film) $\nu_{max}$cm$^{-1}$: 970, 1090, 1130, 1210, 1440, 1595, 1630, 1755, 3370.

EXAMPLE 74

3-(1,1-Methylene-2-methoxycarbonylmethoxyethyl)-6β-(3-oxo-4-methyloct-1-en-6-ynyl)-7α-(2-tetrahydropyranyloxy)bicyclo[3.3.0]oct-2-ene 510 mg of 3-(1,1-methylene-2-methoxycarbonylmethoxyethyl)-6β-formyl-7α-hydroxybicyclo[3.3.0]oct-2-ene (prepared as described in Preparation 8) and 770 mg of dimethyl 2-oxo-3-methylhept-5-ynylphosphonate were reacted as described in Example 72, to give 523 mg of the title compound as an oil.

Infrared Absorption Spectrum (liquid film) $\nu_{max}$cm$^{-1}$: 1595, 1630, 1670, 1692, 1750.

EXAMPLE 75

3-(1,1-Methylene-2-methoxycarbonylmethoxyethyl)-6β-(3-hydroxy-4-methyloct-1-en-6-ynyl)-7α-(2-tetrahydropyranyloxy)bicyclo[3.3.0]oct-2-ene 510 mg of 3-(1,1-methylene-2-methoxycarbonylmethoxyethyl)-6β-(3-oxo-4-methyloct-1-en-6-ynyl)-7α-(2-tetrahydropyranyloxy)bicyclo[3.3.0]oct-2-ene (prepared as described in Example 74), 100 mg of sodium borohydride and 520 mg of cerium chloride heptahydrate were subjected to the same reaction as described in Example 73, to give 501 mg of the title compound as an oil.

Infrared Absorption Spectrum (CHCl$_3$) $\nu_{max}$cm$^{-1}$: 1020, 1595, 1622, 1750, 3450.

EXAMPLE 76

3-(1,1-Methylene-2-methoxycarbonylmethoxyethyl)-6β-(3-hydroxy-4-methyloct-1-en-6-ynyl)-7α-hydroxybicyclo[3.3.0]oct-2-ene 500 mg of 3-(1,1-methylene-2-methoxycarbonylmethoxyethyl)-6β-(3-hydroxy-4-methyloct-1-en-6-ynyl)-7α-(2-tetrahydropyranyloxy)bicyclo[3.3.0]oct-2-ene (prepared as described in Example 75) were subjected to the same reaction as described in Example 73, to obtain 157 mg of the title compound as an oil.

Infrared Absorption Spectrum (liquid film) $\nu_{max}$cm$^{-1}$: 970, 1250, 1595, 1625, 1750, 3370.

EXAMPLE 77

3-(1,1-Methylene-2-carboxymethoxyethyl)-6β-(3-hydroxy-4-methyloct-1-en-6-ynyl)-7α-hydroxybicyclo[3.3.0]oct-2-ene 150 mg of 3-(1,1-methylene-2-methoxycarbonylmethoxyethyl)-6β-(3-hydroxy-4-methyloct-1-en-6-ynyl)-7α-hydroxybicyclo[3.3.0]oct-2-ene (prepared as described in Example 76) were subjected to the same reaction as described in Example 12, to obtain 131 mg of the title compound as an oil. This was a mixture of the steroisomers at the 3- and 4-positions of the octenyl group.

Infrared Absorption Spectrum (liquid film) $\nu_{max}$cm$^{-1}$: 970, 1600, 1630, 1733, 3350.

EXAMPLE 78

3-(1,1-Methylene-2-methoxycarbonylmethoxyethyl)-6β-(3α-hydroxy-1-octenyl)-7α-hydroxybicyclo[3.3.0]oct-2-ene Using 3-(1,1-methylene-2-methoxycarbonylmethoxyethyl)-6β-formyl-7α-hydroxybicyclo[3.3.0]oct-2-ene (prepared as described in Preparation 8) and dimethyl 2-oxoheptylphosphonate as the starting materials, the reactions described in Examples 71 through 73 were repeated, to give the title compound as crystals melting at 64°–65° C.

Infrared Absorption Spectrum (KBr) $\nu_{max}$cm$^{-1}$: 910, 970, 1125, 1205, 1625, 1720, 1750, 1765, 3430.

Nuclear Magnetic Resonance Spectrum (CDCl$_3$) δ ppm: 0.90 (3H, triplet); 3.13 (1H, multiplet); 3.75 (3H, singlet); 4.10 (2H, singlet); 4.30 (2H, singlet); 5.10 (1H, singlet); 5.22 (1H, singlet); 5.57 (2H, multiplet); 5.90 (1H, broad singlet). [α]$^{25}$ −28.3° (C=1.0, CHCl$_3$).

EXAMPLE 79

3-(1,1-Methylene-2-carboxymethoxyethyl)-6β-(3α-hydroxy-3-cyclopentyl-1-propenyl)-7α-hydroxybicyclo[3.3.0]oct-2-ene 0.70 g of 3-(1,1-methylene-2-methoxycarbonylmethoxyethyl)-6β-formyl-7α-hydroxybicyclo[3.3.0]oct-2-ene (prepared as described in Preparation 8) and dimethyl 2-oxo-2-cyclopentylethylphosphonate were treated successively as described in Examples 71, 72, 73 and 12 to give a residue, which was recrystallized from a mixture of ethyl acetate and hexane, to afford 0.15 g of the title compound as pale crystals, melting at 140° C. (with decomposition).

Infrared Absorption Spectrum (KBr) $\nu_{max}$cm$^{-1}$: 900, 970, 1070, 1130, 1220, 1440, 1630, 1745, 3440.

Nuclear Magnetic Resonance Spectrum (CD$_3$OD) δ ppm: 4.05 (2H, singlet); 4.30 (2H, singlet); 5.12 (1H, singlet); 5.24 (1H, singlet); 5.6 (2H, multiplet); 5.92 (1H, singlet).

[α]$^{26}$ −11.8° (C=1.0, methanol).

EXAMPLE 80

3-(1,1-Methylene-2-carboxymethoxyethyl)-6β-(3α-hydroxy-4-methyl-1-octenyl)-7α-hydroxybicyclo[3.3.0]oct-2-ene 0.70 g of 3-(1,1-methylene-2-methoxycarbonylmethoxyethyl)-6β-formyl-7α-hydroxybicyclo[3.3.0]oct-2-ene (prepared as described in Preparation 8) and dimethyl 2-oxo-3-methylheptylphosphonate were treated successively as described in Examples 71, 72, 73 and 12, to give 0.33 g of the title compound, in the form of an oil, which was a mixture of the 6β-(4α-methyloctenyl) isomer and the 6β-(4β-methyloctenyl) isomer.

Infrared Absorption Spectrum (liquid film) $\nu_{max}$cm$^{-1}$: 880, 970, 1045, 1090, 1125, 1220, 1595, 1630, 1730, 3330.

Nuclear Magnetic Resonance Spectrum (CDCl$_3$) δppm: 0.8–1.0 (6H, multiplet); 3.1 (1H, multiplet); 4.10 (2H, singlet); 4.31 (2H, singlet); 5.12 (1H, singlet); 5.22 (1H, singlet); 5.55 (2H, multiplet); 5.92 (1H, singlet).

[α]$^{24}$ −17.0° (C=1.0, CHCl$_3$).

EXAMPLE 81

3-(1,1-Methylene-2-carboxymethoxyethyl)-6β-(3α-hydroxy-4,4-dimethyl-1-octenyl)-7α-hydroxybicyclo[3.3.0]oct-2-ene 0.64 g of 3-(1,1-methylene-2-methoxycarbonylmethoxyethyl)-6β-formyl-7α-hydroxybicyclo[3.3.0]oct-2-ene (prepared as described in Preparation 8) and dimethyl 2-oxo-3,3-dimethylheptylphosphonate were treated successively as described in Examples 71, 72, 73 and 12, to afford 0.32 g of the title compound as an oil.

Infrared Absorption Spectrum (liquid film) $\nu_{max}$cm$^{-1}$: 880, 970, 1045, 1090, 1125, 1220, 1380, 1595, 1630, 1735, 3350.

Nuclear Magnetic Resonance Spectrum (CDCl$_3$) δppm: 0.90 (9H, multiplet); 3.1 (1H, multiplet); 4.08 (2H, singlet); 4.30 (2H, singlet); 5.12 (1H, singlet); 5.21 (1H, singlet); 5.55 (2H, multiplet); 5.90 (1H, singlet).

[α]$^{25}$ −7.8° (C=1.0, CHCl$_3$).

EXAMPLE 82

Mixture of
3-(1-methoxycarbonyl-2-hydroxypropyl)-6β-[3α-(2-tetrahydropyranyloxy)-1-octenyl]-7α-(2-tetrahydropyranyloxy)bicyclo[3.3.0]oct-2-ene and its oct-3-ene isomer 0.81 ml of dicyclohexylamine was dissolved in 18 ml of tetrahydrofuran, and 2.48 ml of a 15% w/w solution of butyllithium in hexane were added dropwise at −70° C. to the solution. The mixture was stirred for 10 minutes at the same temperature, and then 0.78 ml of hexamethylphosphoric triamide was added dropwise and the mixture was stirred for a further 10 minutes. 1.0 g of 3,3-methoxycarbonylmethylene-6β-[3α-(2-tetrahydropyranyloxy)-1-octenyl]-7α-(2-tetrahydropyranyloxy)bicyclo[3.3.0]octane (prepared following the procedures described in European Patent Publication No. 136779) dissolved in 5 ml of tetrahydrofuran was added dropwise to the solution, and the mixture was stirred for 15 minutes. 0.23 ml of acetaldehyde was then added dropwise thereto. The mixture was stirred for 30 minutes at −70° C., and then 5 ml of a saturated aqueous solution of ammonium chloride were added thereto and the mixture was warmed gradually to room temperature. 150 ml of water were added to the mixture, and the mixture was extracted with ethyl acetate. The extract was washed with dilute hydrochloric acid and water, and dried over anhydrous sodium sulfate. Evaporation of the solvent under reduced pressure gave 1.2 g of a residue, which was purified by silica gel column chromatography, eluted with hexane containing from 15 to 30% v/v ethyl acetate, to afford 1.05 g of a mixture of the title compounds as an oil.

Infrared Absorption Spectrum (liquid film) $\nu_{max}$cm$^{-1}$: 980, 1025, 1080, 1120, 1160, 1205, 1740, 3470.

Nuclear Magnetic Resonance Spectrum (CDCl$_3$) δppm: 3.70 (3H, singlet); 4.70 (2H, broad singlet); 5.3–5.7 (3H, multiplet).

EXAMPLE 83

Mixture of
3-(1-methoxycarbonyl-2-methanesulfonyloxypropyl)-6β-[3α-(2-tetrahydropyranyloxy)-1-octenyl]-7α-(2-tetrapyranyloxy)bicyclo[3.3.0]oct-2-ene and its oct-3-ene isomer 2.18 g of the mixture of
3-(1-methoxycarbonyl-2-hydroxypropyl)-6β-[3α-(2-tetrahydropyranyloxy)-1-octenyl]-7α-(2-tetrahydropyranyloxy)bicyclo[3.3.0]oct-2-ene and its oct-3-ene isomer (prepared as described in Example 82) were treated as described in Example 7, to afford 2.72 g of a mixture of the title compounds as an oil.

Infrared Absorption Spectrum (liquid film) $\nu_{max}$cm$^{-1}$: 905, 980, 1025, 1035, 1080, 1125, 1180, 1205, 1360, 1740.

Nuclear Magnetic Resonance Spectrum (CDCl$_3$) δppm: 2.98 (3H, singlet); 3.71 (3H, singlet); 4.70 (2H, broad singlet); 5.2 (1H, multiplet), 5.4–5.7 (3H, multiplet).

EXAMPLE 84

Mixture of
3-(1-methoxycarbonyl-1-propenyl)-6β-[3α-(2-tetrahydropyranyloxy)-1-octenyl]-7α-(2-tetrahydropyranyloxy)bicyclo[3.3.0]oct-2-ene and its oct-3-ene isomer 2.72 g of the mixture of 3-(1-methoxycarbonyl-2-methanesulfonyloxypropyl)-6β-[3α-(2-tetrahydropyranyloxy)-1-octenyl]-7α-(2-tetrahydropyranyloxy)bicyclo[3.3.0]oct-2-ene and its oct-3-ene isomer (prepared as described in Example 83) were treated as described in Example 8, to afford 1.84 g of a mixture of the title compounds as an oil.

Infrared Absorption Spectrum (liquid film) $\nu_{max}$cm$^{-1}$: 980, 1025, 1035, 1080, 1140, 1205, 1260, 1440, 1625, 1725.

Nuclear Magnetic Resonance Spectrum (CDCl$_3$) δppm: 0.9 (3H, triplet); 1.82 (3H, doublet); 3.77 (3H, doublet); 4.73 (2H, broad singlet), 5.3–5.9 (4H, multiplet).

EXAMPLE 85

3-(1-Hydroxymethyl-1propenyl)-6β-[3α-(2-tetrahydropyranyloxy)-1-octenyl]-7α-(2-tetrahydropyranyloxy)bicyclo[3.3.0]oct-2-ene 0.4 g of lithium aluminum hydride was suspended in 20 ml of diethyl ether, and a solution of 0.46 g of aluminum chloride in 10 ml of diethyl ether was added dropwise, with ice-cooling, thereto. The mixture was then stirred for 20 minutes. To the mixture was added dropwise a solution of 1.84 g of the mixture of 3-(1-methoxycarbonyl-1propenyl)-6β-[3α-(2-tetrahydropyranyloxy)-1-octenyl]-7α-(2-tetrahydropyranyloxy)bicyclo[3.3.0]oct-2-ene and its oct-3-ene isomer (prepared as described in Example 84) in 10 ml of diethyl ether, and the mixture was stirred for 20 minutes at room temperature. 1.64 ml of a 4% w/v aqueous solution of sodium hydroxide was added, and the mixture was stirred for 30 minutes at room temperature. The insoluble materials were filtered off using a Celite filter aid, and the filtrate was concentrated by evaporation under reduced pressure to give a residue, which was purified by silica gel column chromatography, eluted with hexane containing from 20 to 25% v/v ethyl acetate, to afford 0.58 g of the title compound.

Infrared Absorption Spectrum (Liquid film) $\nu_{max}$cm$^{-1}$: 815, 870, 980, 1020, 1080, 1120, 1135, 1205, 3450.

Nuclear Magnetic Resonance Spectrum (CDCl$_3$) δppm: 1.83 (3H, doublet); 4.4 (2H, broad singlet); 4.7 (2H, broad singlet), 5.2–5.8 (4H, multiplet).

EXAMPLE 86

3-(1-Carboxymethoxymethyl-1-propenyl)-6β-[3α-(2-tetrahydropyranyloxy)-1-octenyl]-7α-(2-tetrahydropyranyloxy)bicyclo[3.3.0]oct-2-ene 0.57 g of 3-(1-hydroxymethyl-1-propenyl)-6β-[3α-(2-tetrahydropyranyloxy)-1-octenyl]-7α-(2-tetrahydropyranyloxy)bicyclo[3.3.0]oct-2-ene (prepared as described in Example 85) was treated as described in Example 58, to afford 0.25 g of the title compound as an oil.

Infrared Absorption Spectrum (liquid film) $\nu_{max}$cm$^{-1}$: 980, 1020, 1120, 1730, 1760.

Nuclear Magnetic Resonance Spectrum (CDCl$_3$) δppm: 4.07 (2H, singlet); 4.4 (2H, singlet); 4.72 (2H, broad singlet), 5.4–5.9 (4H, multiplet).

EXAMPLE 87

3-(1-Carboxymethoxymethyl-1-propenyl)-6β-(3α-hydroxy-1-octenyl)-7α-hydroxybicyclo[3.3.0]oct-2-ene 0.24 g of 3-(1-carboxymethoxymethyl-1-propenyl)-6β-[3α-(2-tetrahydropyranyloxy)-1-octenyl]-7α-(2-tetrahydropyranyloxy)bicyclo[3.3.0]oct-2-ene (prepared as described in Example 86) was treated as described in Example 62, to afford a residue which was purified by recrystallization from a mixture of ethyl acetate and hexane, to give 0.095 g of the title compound as crystals, melting at 100°–102° C.

Infrared Absorption Spectrum (KBr) $\nu_{max}$cm$^{-1}$: 815, 970, 1125, 1630, 1740, 3430.

Nuclear Magnetic Resonance Spectrum (CDCl$_3$) δppm: 0.9 (3H, triplet); 1.82 (3H, doublet); 3.1 (1H, multiplet); 4.03 (2H, singlet), 4.4 (2H, singlet); 5.16 (3H, singlet); 5.4–5.9 (4H, multiplet).

$[\alpha]^{25}$ −18.9° (C=1.0, CHCl$_3$).

PREPARATION 1

Mixture of
3-(1-methoxycarbonyl-2-benzyloxyethyl)-6β-(2-tetrahydropyranyloxymethyl)-7α-(2-tetrahydropyranyloxy)bicyclo[3.3.0]oct-2-ene and 3-(1-Methoxycarbonyl-2-benzyloxyethyl)-6β-(2-tetrahydropyranyloxymethyl)-7α-(2-tetrahydropyranyloxy)bicyclo[3.3.0]oct-3-ene By treating 0.5 g of 3,3-methoxycarbonylmethylene-6β-(2-tetrahydropyranyloxymethyl)-7α-(2-tetrahydropyranyloxy)bicyclo[3.3.0]octane in the same manner as described in Example 56, 0.35 g of the title compound was obtained.

Infrared Absorption Spectrum (liquid film) $\nu_{max}$cm$^{-1}$: 1030, 1080, 1120, 1140, 1205, 1350, 1745.

Nuclear Magnetic Resonance Spectrum (CDCl$_3$) δppm: 3.67 (3H, singlet); 4.49 (2H, singlet); 5.48 (1H, multiplet); 7.3 (5H, singlet).

PREPARATION 2

Mixture of
3-(1-hydroxymethyl-2-benzyloxyethyl)-6β-(2-tetrahydropyranyloxymethyl)-7α-(2-tetrahydropyranyloxy)bicyclo[3.3.0]oct-2-ene and 3-(1-hydroxymethyl-2-benzyloxyethyl)-6β-(2-tetrahydropyranyloxymethyl)-7α-(2-tetrahydropyranyloxy)bicyclo[3.3.0]oct-3-ene By treating 0.35 g of the mixture of 3-(1-methoxycarbonyl-2-benzyloxyethyl)-6β-(2-tetrahydropyranyloxymethyl)-7α-(2-tetrahydropyranyloxy)bicyclo[3.3.0]oct-2-ene and its oct-3-ene isomer (prepared as described in Preparation 1) in the same manner as described in Example 57, 0.29 g of the title compound was obtained.

Infrared Absorption Spectrum (liquid film) $\nu_{max}$cm$^{-1}$: 1030, 1080, 1120, 3470.

Nuclear Magnetic Resonance Spectrum (CDCl$_3$) δppm: 4.54 (2H, singlet);4.64 (2H, broad singlet); 5.45 (1H, multiplet); 7.36 (5H, singlet).

PREPARATION 3

Mixture of
3-(1-benzyloxymethyl-2-carboxymethoxyethyl)-6β-(2-tetrahydropyranyloxymethyl)-7α-(2-tetrahydropyranyloxy)bicyclo[3.3.0]oct-2-ene and 3-(1-benzyloxymethyl-2-carboxymethoxyethyl)-6β-(2-tetrahydropyranyloxymethyl)-7α-(2-tetrahydropyranyloxy)bicyclo[3.3.0]oct-3-ene By treating 1.2 g of the mixture of 3-(1-hydroxymethyl-2-benzyloxyethyl)-6β-(2-tetrahydropyranyloxymethyl)-7α-(2-tetrahydropyranyloxy)bicyclo[3.3.0]oct-2-ene and its oct-3-ene isomer (prepared as described in Preparation 2) in the same manner as described in Example 58, 1.25 g of the title compound was obtained.

Infrared Absorption Spectrum (liquid film) $\nu_{max}$cm$^{-1}$: 975, 1020, 1030, 1075, 1120, 1130, 1200, 1260, 1350, 1455, 1740, 1760, 2650, 3200.

Nuclear Magnetic Resonance Spectrum (CDCl$_3$) δppm: 4.07 (2H, singlet); 4.43 (1H, multiplet); 4.54 (2H, singlet); 4.65 (2H, broad singlet); 7.36 (5H, singlet).

PREPARATION 4

Mixture of
3-(1-hydroxymethyl-2-methoxycarbonylmethoxyethyl)-6β-(2-tetrahydropyranyloxymethyl)-7α-(2-tetrahydropyranyloxy)bicyclo[3.3.0]oct-2-ene and 3-(1-hydroxymethyl-2-methoxycarbonylmethoxyethyl)-6β-(2-tetrahydropyranyloxymethyl)-7α-(2-tetrahydropyranyloxy)bicyclo[3.3.0]oct-3-ene By treating 1.26 g of the mixture of 3-(1-benzyloxymethyl-2-carboxymethoxyethyl)-6β-(2-tetrahydropyranyloxymethyl)-7α-(2-tetrahydropyranyloxy)bicyclo[3.3.0]oct-2-ene and its oct-3-ene isomer (prepared as described in Preparation 3) in the same manner as described in Example 59, 0.78 g of the title compound was obtained.

Infrared Absorption Spectrum (liquid film) $\nu_{max}$cm$^{-1}$: 1030, 1740, 1760, 3480.

Nuclear Magnetic Resonance Spectrum (CDCl$_3$) δppm: 3.76 (3H, singlet); 4.10 (2H, singlet); 4.63 (2H, broad singlet); 5.47 (1H, multiplet).

PREPARATION 5

Mixture of
3-(1-methanesulfonyloxymethyl-2-methoxycarbonylmethoxyethyl)-6β-(2-tetrahydropyranyloxymethyl)-7α-(2-tetrahydropyranyloxy)bicyclo[3.3.0]oct-2-ene and 3-(1-methanesulfonyloxymethyl-2-methoxycarbonylmethoxyethyl)-6β-(2-tetrahydropyranyloxymethyl)-7α-(2-tetrahydropyranyloxy)bicyclo[3.3.0]oct-3-ene By treating 0.77 g of the mixture of 3-(1-hydroxymethyl-2-methoxycarbonylmethoxyethyl)-6β-(2-tetrahydropyranyloxymethyl)-7α-(2-tetrahydropyranyloxy)bicyclo[3.3.0]oct-2-ene and its oct-3-ene isomer (prepared as described in Preparation 4) in the same manner as described in Example 7, 0.85 g of the title compound was obtained.

Infrared Absorption Spectrum (liquid film) $\nu_{max}$cm$^{-1}$: 1030, 1075, 1760.

Nuclear Magnetic Resonance Spectrum (CDCl$_3$) δppm: 3.0 (3H, singlet); 3.75 (3H, singlet); 4.08 (2H, singlet); 4.37 (2H, doublet, J=6 Hz); 4.53 (1H, multiplet); 4.64 (2H, broad singlet).

PREPARATION 6

Mixture of
3-(1,1-methylene-2-methoxycarbonylmethoxyethyl)-
6β-(2-tetrahydropyranyloxymethyl)-7α-(2-tetrahydropyranyloxy)bicyclo[3.3.0]oct-2-ene and 3-(1,1-methylene-2-methoxycarbonylmethoxyethyl)-
6β-(2-tetrahydropyranyloxymethyl)-7α-(2-tetrahydropyranyloxy)bicyclo[3.3.0]oct-3-ene By treating 0.83 g of the mixture of 3-(1-methanesulfonyloxymethyl-2-methoxycarbonylmethoxyethyl)-6β-(2-tetrahydropyranyloxymethyl)-7α-(2-tetrahydropyranyloxy)bicyclo[3.3.0]oct-2-ene and its oct-3-ene isomer (prepared as described in Preparation 5) in the same manner as described in Example 8, 0.52 g of the title compound was obtained.

Infrared Absorption Spectrum (liquid film) $\nu_{max}$cm$^{-1}$: 1025, 1030, 1595, 1630, 1740, 1760.

Nuclear Magnetic Resonance Spectrum (CDCl$_3$) δppm: 3.76 (3H, singlet); 4.08 (2H, singlet); 4.39 (2H, singlet); 4.66 (2H, broad singlet); 5.10 (1H, singlet); 5.19 (1H, singlet); 5.90 (1H broad singlet).

PREPARATION 7

3-(1,1-Methylene-2-methoxycarbonylmethoxyethyl)-
6β-hydroxymethyl-7α-hydroxybicyclo[3.3.0]oct-2-ene and 3-(1,1-methylene-2-methoxycarbonylmethoxyethyl)-
6β-hydroxymethyl-7α-hydroxybicyclo[3.3.0]oct-3-ene By treating 0.52 g of the mixture of 3-(1,1-methylene-2-methoxycarbonylmethoxyethyl)-6β-(2-tetrahydropyranyloxymethyl)-7α-(2-tetrahydropyranyloxy)-bicyclo[3.3.0]oct-2-ene and its oct-3-ene isomer (prepared as described in Preparation 6) in the same manner as described in Example 11, 0.20 g of the oct-2-ene isomer (the compound with the lower polarity) of the title compound was obtained from the fractions eluted with hexane containing from 40–50% v/v ethyl acetate, and 0.10 g of the oct-3-ene isomer (the compound with the higher polarity) of the title compound was obtained from the fractions eluted with hexane containing from 50 to 70% v/v ethyl acetate.

Oct-2-ene compound:
Melting at 60°–61° C. (after recrystallization from a mixture of ethyl acetate and hexane).

Infrared Absorption Spectrum (molten film) $\nu_{max}$cm$^{-1}$: 1740, 3400.

Nuclear Magnetic Resonance Spectrum (CDCl$_3$) δ ppm: 3.76 (3H, singlet); 4.10 (2H, singlet); 4.31 (2H, singlet); 5.12 (1H, singlet); 5.23 (1H, singlet); 5.94 (1H, broad singlet).

Oct-3-ene compound:
Infrared Absorption Spectrum (liquid film) $\nu_{max}$cm$^{-1}$: 1010, 1040, 1080, 1120, 1215, 1440, 1595, 1630, 1750, 3400.

Nuclear Magnetic Resonance Spectrum (CDCl$_3$) δ ppm: 3.76 (3H, singlet); 4.10 (2H, singlet); 4.32 (2H, singlet); 5.13 (1H, singlet); 5.24 (1H, singlet); 5.94 (1H, singlet).

PREPARATION 8

3-(1,1-Methylene-2-methoxycarbonylmethoxyethyl)-
6β-formyl-7α-tetrahydropyranyloxybicyclo[3.3.0]oct-2-ene 0.51 g of 3-(1,1-methylene-2-methoxycarbonylmethoxyethyl)-6β-hydroxymethyl-7α-hydroxybicyclo[3.3.0]oct-2-ene (prepared as described in Preparation 7) and 0.44 ml of trimethylamine were dissolved in 10 ml of benzene. A solution of 0.20 ml of trichloroacetyl chloride in 5 ml of benzene was added dropwise to this solution, with ice cooling, and the mixture was stirred for 20 minutes. The reaction mixture was then diluted with ice-water and extracted with ethyl acetate. The extract was washed with water and then dried over anhydrous sodium sulfate. The solvent was then distilled off, yielding 0.52 g of the mono(trichloroacetyl) compound. 0.52 g of this acetyl compound and 0.16 ml of dihydropyran were dissolved in 2 ml of methylene chloride, and p-toluenesulfonic acid was added. The mixture was stirred at room temperature for 10 minutes. The reaction mixture was then diluted with ethyl acetate, washed with water and dried over anhydrous sodium sulfate. The solvent was distilled off from the extract. The resulting pyranyl compound was dissolved in 15 ml of methanol, to which 1 ml of a saturated aqueous solution of sodium bicarbonate was added, and the mixture was stirred for 2 hours at 30°–40° C. The reaction product was diluted with a saturated aqueous solution of sodium chloride and extracted with ethyl acetate. The extract was washed with water and dried over anhydrous sodium sulfate. The solvent was then distilled off from the extract. The resulting residue was purified by silica gel column chromatography, eluted with hexane containing from 30 to 50% v/v ethyl acetate, to give 0.39 g of the corresponding alcohol compound, as an oil.

Infrared Absorption Spectrum (liquid film) $\nu_{max}$cm$^{-1}$: 1020, 1750, 3420.

0.37 g of this alcohol compound was dissolved in 0.5 ml of dimethyl sulfoxide and 1.5 ml of triethylamine was added to the resulting solution. 900 mg of a complex of sulfur trioxide and pyridine in 3 ml of dimethyl sulfoxide was added dropwise with stirring at room temperature. The mixture was stirred for 30 minutes, diluted with ice-water, and extracted with ethyl acetate. The extract was then washed with water and dried over anhydrous sodium sulfate. The solvent was then distilled off from the extract, giving 0.36 g of the title compound as an oil.

Infrared Absorption Spectrum (liquid film) $\nu_{max}$cm$^{-1}$: 1030, 1595, 1630, 1720, 1750, 2720

We claim:

1. A compound of formula (I):

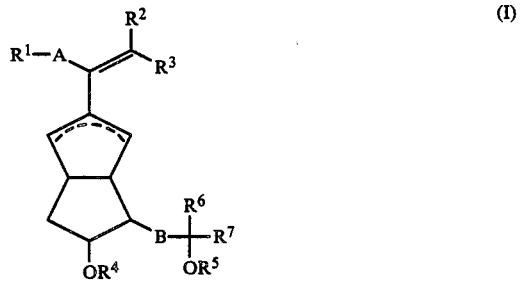

in which:
the dotted line represents a double bond at either the 2-position or the 3-position;

$R^1$ represents a carboxy group, an ester thereof selected from the group consisting of a $C_1$–$C_{10}$ alkyl ester, a $C_3$–$C_7$ cycloalkyl ester, a ($C_6$ or $C_{10}$ carbocyclic aryl)-$C_1$–$C_3$ alkyl ester, a phenyl ester, a phenyl ester having at least one substituent selected from the group consisting of $C_1$-$C_4$ alkyl groups and benzoylamino groups, a benzhydryl ester, a phenacyl ester and a geranyl ester, a tetrazolyl group, a carbamoyl group, a carbamoyl group having 1 or 2 substituents selected from the group consisting of substituents (a):

(a) $C_1$-$C_4$ alkyl groups, $C_1$-$C_6$ aliphatic carboxylic acyl groups, $C_6$ or $C_{10}$ carbocyclic aryl carboxylic acyl groups, $C_1$-$C_4$ alkanesulfonyl groups, $C_6$-$C_{10}$ carbocyclic arylsulfonyl groups, phenyl groups and phenyl groups having at least one $C_1$-$C_4$ alkyl substituent, a formyl group, a group of formula

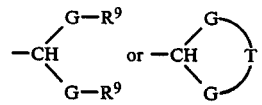

where:

G represents an oxygen or a sulfur atom;

$R^9$ represents a $C_1$-$C_4$ alkyl group; and

T represents a $C_2$-$C_5$ alkylene group, or a group of formula —$CH_2OR^{10}$ or —$COCH_2OR^{10}$ where:

$R^{10}$ represents a hydrogen atom, a $C_2$-$C_5$ aliphatic acyl group, a $C_6$ or $C_{10}$ carbocyclic aryl carboxylic acyl group, a ($C_6$ or $C_{10}$ carbocyclic aryl)-$C_1$-$C_3$ alkyl group, a heterocyclic group having 5 or 6 ring atoms of which 1 or 2 are heteroatoms selected from the group consisting of oxygen and sulfur atoms, a ($C_1$-$C_4$ alkoxy)methyl group, an alkylthioalkyl group in which each alkyl part is $C_1$-$C_4$, a ($C_6$ or $C_{10}$ carbocyclic aryl)-$C_1$-$C_3$ alkoxymethyl group or a tri-substituted silyl group, said three substituents being the same or different and are $C_1$-$C_4$ alkyl, phenyl or naphthyl group;

$R^2$ and $R^3$ are independently selected from the group consisting of hydrogen atoms and $C_1$-$C_4$ alkyl groups or $R^2$ and $R^3$, together with the carbon atom to which they are attached, represent a $C_3$-$C_7$ cycloalkyl group;

$R^4$ and $R^5$ are independently selected from the group consisting of groups of formula —$R^{10}$;

$R^6$ represents a hydrogen atom or a $C_1$-$C_4$ alkyl group;

$R^7$ represents a $C_1$-$C_{12}$ alkyl group, a $C_1$-$C_{12}$ alkyl group having at least one substituent selected from the group consisting of substituents (b):

(b) halogen atoms, $C_1$-$C_4$ alkoxy groups, groups of formula —$OR^{10}$, $C_1$-$C_6$ aliphatic carboxylic acyl groups and $C_6$ or $C_{10}$ carbocyclic aryl carboxycyclic acyl groups, a $C_3$-$C_{12}$ alkenyl group, a $C_3$-$C_{12}$ alkenyl group having at least one substituent selected from the group consisting of substituents (b), a $C_3$-$C_{12}$ alkynyl group, a $C_3$-$C_{12}$ alkynyl group having at least one substituent selected from the group consisting of substituents (b) or a group of formula —$D$—$R^8$, where:

D represents a single bond, a $C_1$-$C_6$ alkylene group, a $C_2$-$C_6$ alkenylene group or a $C_1$-$C_6$ alkylene or alkenylene group in which the carbon chain is interrupted by at least one oxygen or sulfur atom, or by a $C_3$-$C_7$ cycloalkylene group; and $R^8$ represents a $C_3$-$C_{10}$ cycloalkyl group, a $C_3$-$C_{10}$ cycloalkyl group having at least one $C_1$-$C_6$ alkyl substituent, a $C_5$-$C_{10}$ cycloalkenyl group, a $C_6$ or $C_{10}$ carbocyclic aryl group or a 5- or 6-membered heterocyclic group having 1 or 2 oxygen and/or sulfur hetero atoms;

A represents a single bond, a $C_1$-$C_7$ alkylene group, a $C_1$-$C_7$ alkylene group having at least one fluorine substituent, a group of formula —$CH=CH$—$(CH_2)_n$— where n is 0 or an integer from 1 to 5, or a group of formula —$(CH_2)_p$—$E$—$(CH_2)_q$—, where:

p is 0 or an integer from 1 to 3, q is an integer from 1 to 3, and

E is an oxygen or sulfur atom; and

B represents a group of formula —$CH_2CH_2$—, —$CH=CH$— or —$C\equiv C$—, and pharmaceutically acceptable salts thereof.

2. A compound as claimed in claim 1, wherein:

$R^1$ represents a carboxy group, a carbamoyl group, a carbamoyl group having 1 or 2 substituents selected from the group consisting of $C_1$-$C_4$ alkyl, phenyl and methanesulfonyl substituents, a formyl group, a group of formula

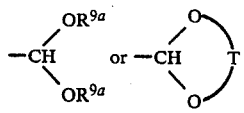

in which:

$R^9$ represents a $C_1$-$C_4$ alkyl group; and

T represents an ethylene, trimethylene or 2,2-dimethyltrimethylene group, a hydroxymethylcarbonyl group or a hydroxymethyl group, and, where $R^1$ represents a carboxy group, $C_1$-$C_{10}$ alkyl esters thereof.

3. A compound as claimed in claim 1, wherein:

$R^2$ and $R^3$ are independently selected from the group consisting of hydrogen atoms and $C_1$-$C_4$ alkyl groups.

4. A compound as claimed in claim 1, wherein:

$R^4$ and $R^5$ are independently selected from the group consisting of hydrogen atoms, tetrahydropyranyl groups, dimethyl-t-butylsilyl groups and benzoyl groups.

5. A compound as claimed in claim 1, wherein:

$R^6$ represents a hydrogen atom or a methyl group.

6. A compound as claimed in claim 1, wherein:

$R^7$ represents a $C_3$-$C_{10}$ alkyl group, a $C_3$-$C_{10}$ alkyl group having at least one substituent selected from the group consisting of fluorine, chlorine and $C_1$-$C_4$ alkoxy substituents, a $C_3$-$C_{10}$ alkenyl group, a $C_3$-$C_8$ alkynyl group, a group of formula —$D$—$R^8$ in which:

D represents a single bond, a $C_1$-$C_4$ alkylene group, an oxymethylene group or a thiomethylene group, and $R^8$ represents a $C_3$-$C_{10}$ cycloalkyl group, a $C_3$-$C_{10}$ cycloalkyl group having at least one $C_1$-$C_4$ alkyl substituent, a $C_5$-$C_6$ cycloalkenyl group, a thienyl group, a phenyl group or a phenyl group having at least one substituent selected from the group consisting of $C_1$-$C_4$ alkyl, $C_1$-$C_4$ alkoxy, trifluoromethyl and halogen substituents.

7. A compound as claimed in claim 1, wherein:
A represents a single bond, a straight chain $C_1$-$C_7$ alkylene group, a fluorinated $C_1$-$C_7$ alkylene group or a group of formula —CH=CH—$CH_2$— or —$(CH_2)_p$—E—$(CH_2)_q$—
in which:
p is 0 or an integer from 1 to 3,
q is an integer from 1 to 3, and
E is an oxygen or sulfur atom.

8. A compound as claimed in claim 1, wherein:
B is a trans-vinylene group.

9. A compound as claimed in claim 1, wherein the bond represented by the dotted line is a double bond at the 2-position.

10. A compound as claimed in claim 1, wherein:
$R^1$ represents a carboxy group, a hydroxymethyl group, a carbamoyl group or a carbamoyl group having a phenyl substituent, and, where $R^1$ represents a carboxy group, $C_1$-$C_{10}$ alkyl esters thereof;
$R^2$ and $R^3$ are independently selected from the group consisting of hydrogen atoms and $C_1$-$C_4$ alkyl groups;
$R^4$ and $R^5$ are independently selected from the group consisting of hydrogen atoms, tetrahydropyranyl groups, dimethyl-t-butylsilyl groups and benzoyl groups;
$R^6$ represents a hydrogen atom or a methyl group;
$R^7$ represents a $C_3$-$C_{10}$ alkyl group, a $C_3$-$C_{10}$ alkyl group having a $C_1$-$C_4$ alkoxy substituent, a $C_3$-$C_{10}$ alkenyl group, a $C_3$-$C_8$ alkynyl group or a group of formula —D—$R^8$, where
D represents a single bond, a $C_1$-$C_4$ alkylene group, an oxymethylene group or a thiomethylene group, and
$R^8$ represents a $C_3$-$C_{10}$ cycloalkyl group, a thienyl group, a phenyl group or a substituted phenyl group having at least one substituent selected from the group consisting of halogen atom, $C_1$-$C_4$ alkyl and trifluoromethyl substituents;
A represents a $C_1$-$C_5$ alkylene group, a fluorinated $C_1$-$C_5$ alkylene group or a group of formula —$(CH_2)_p$—E—$(CH_2)_q$— where:
E represents an oxygen or sulfur atom,
p is 1 or 2, and
q is 1 or 2; and
the dotted line represents a double bond at the 2-position.

11. A compound as claimed in claim 1, wherein:
$R^1$ represents a carboxy group and methyl esters thereof;
$R^2$, $R^3$, $R^4$ and $R^5$ all represent hydrogen atoms;
$R^6$ represents a hydrogen atom or a methyl group;
$R^7$ represents a $C_5$-$C_{10}$ alkyl group, a $C_5$-$C_{10}$ alkenyl group, a $C_5$-$C_8$ alkynyl group or a group of formula —D—$R^8$, where
D represents a single bond, a methylene group or an oxymethylene group, and
$R^8$ represents a $C_3$-$C_7$ cycloalkyl group or a phenyl group;
A represents a trimethylene group, a methyleneoxymethylene group or a methylenethiomethylene group;
B represents a vinylene (—CH=CH—) group, preferably a trans-vinylene group; and
the dotted line represents a double bond at the 2-position.

12. A compound as claimed in claim 1, selected from the group consisting of 3-(1,1-methylene-4-carboxybutyl)-6β-(3α-hydroxy-1-octenyl)-7α-hydroxybicyclo[3.3.0]oct-2-ene and pharmaceutically acceptable salts and esters thereof.

13. A compound as claimed in claim 1, selected from the group consisting of 3-(1,1-methylene-4-carboxybutyl)-6β-(3α-hydroxy-4-methyl-1-octenyl)-7α-hydroxybicyclo[3.3.0]oct-2-ene and pharmaceutically acceptable salts and esters thereof.

14. A compound as claimed in claim 1, selected from the group consisting of 3-(1,1-methylene-4-carboxybutyl)-6β-(3α-hydroxy-5-methyl-1-nonenyl)-7α-hydroxybicyclo[3.3.0]oct-2-ene and pharmaceutically acceptable salts and esters thereof.

15. A compound as claimed in claim 1, selected from the group consisting of 3-(1,1-methylene-4-carboxybutyl)-6β-(3α-hydroxy-4,4-dimethyl-1-octenyl)-7α-hydroxybicyclo[3.3.0]oct-2-ene and pharmaceutically acceptable salts and esters thereof.

16. A compound as claimed in claim 1, selected from the group consisting of 3-(1,1-methylene-4-carboxybutyl)-6β-(3α-hydroxy-4,4-dimethyl-1,8-nonadietnyl)-7α-hydroxybicyclo[3.3.0]oct-2-ene and pharmaceutically acceptable salts and esters thereof.

17. A compound as claimed in claim 1, selected from the group consisting of 3-(1,1-methylene-4-carboxybutyl)-6β-(3α-hydroxy-5,9-dimethyl-1,8-decadienyl)-7α-hydroxybicyclo-[3.3.0]oct-2-ene and pharmaceutically acceptable salts and esters thereof.

18. A compound as claimed in claim 1, selected from the group consisting of 3-(1,1-methylene-2-carboxymethoxyethyl)-6β-(3α-hydroxy-4-methyloct-1-en-6-ynyl)-7α-hydroxy-bicyclo[3.3.0]ect-2-ene and pharmaceutically acceptable salts and esters thereof.

19. A compound as claimed in claim 1, selected from the group consisting of 3-(1,1-methylene-2-carboxymethoxyethyl)-6β-(3α-hydroxy-3-cyclopentyl-1-propenyl)-7α-hydroxy-bicyclo[3.3.0]oct-2-ene and pharmaceutically acceptable salts and esters thereof.

20. A compound as claimed in claim 1, selected from the group consisting of 3-(1,1-methylene-4-carboxybutyl)-6β-(3α-hydroxy-3-cyclohexyl-1-propenyl)-7α-hydroxybicyclo-[3.3.0]oct-2-ene and pharmaceutically acceptable salts and esters thereof.

21. A compound as claimed in claim 1, selected from the group consisting of 3-(1,1-methylene-2-carboxymethoxyethyl)-6β-(3α-hydroxy-3-cyclohexyl-1-propenyl)-7α-hydroxy-bicyclo[3.3.0]oct-2-ene and pharmaceutically acceptable salts and esters thereof.

22. A compound as claimed in claim 1, selected from the group consisting of 3-(1,1-methylene-2-carboxymethoxyethyl)-6β-(3α-hydroxy-4-phenoxy-1-butenyl)-7α-hydroxy-bicyclo[3.3.0]oct-2-ene and pharmaceutically acceptable salts and esters thereof.

23. A pharmaceutical composition comprising an effective amount of a prostaglandin derivative to treat a thrombotic or ulcerative condition in admixture with a pharmaceutically acceptable carrier or diluent wherein the prostaglandin derivative is selected from the group consisting of formula (I):

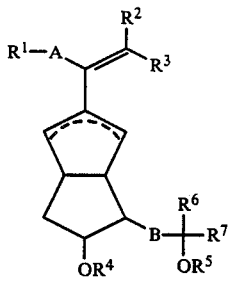
(I)

in which:
the dotted line represents a double bond at either the 2-position or the 3-position;

$R^1$ represents a carboxy group, an ester thereof selected from the group consisting of a $C_1$-$C_{10}$ alkyl ester, a $C_3$-$C_7$ cycloalkyl ester, a ($C_6$ or $C_{10}$ carbocyclic aryl)-$C_1$-$C_3$ alkyl ester, a phenyl ester, a phenyl ester having at least one substituent selected from the group consisting of $C_1$-$C_4$ alkyl groups and benzoylamino groups, a benzhydryl ester, a phenacyl ester and a geranyl ester, a tetrazolyl group, a carbamoyl group, a carbamoyl group having 1 or 2 substituents selected from the group consisting of substituents (a):
(a) $C_1$-$C_4$ alkyl groups, $C_1$-$C_6$ aliphatic carboxylic acyl groups, $C_6$ or $C_{10}$ carbocyclic aryl carboxylic acyl groups, $C_1$-$C_4$ alkanesulfonyl groups, $C_6$-$C_{10}$ carbocyclic arylsulfonyl groups, phenyl groups and phenyl groups having at least one $C_1$-$C_4$ alkyl substituent, a formyl group, a group of formula

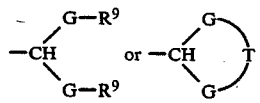

where:
G represents an oxygen or a sulfur atom;
$R^9$ represents a $C_1$-$C_4$ alkyl group; and
T represents a $C_2$-$C_5$ alkylene group,
or a group of formula $-CH_2OR^{10}$ or $-COCH_2OR^{10}$
where:
$R^{10}$ represents a hydrogen atom, a $C_2$-$C_5$ aliphatic acyl group, a $C_6$ or $C_{10}$ carbocyclic aryl carboxylic acyl group, a ($C_6$ or $C_{10}$ carbocyclic aryl)-$C_1$-$C_3$ alkyl group, a heterocyclic group having 5 or 6 ring atoms of which 1 or 2 are heteroatoms selected from the group consisting of oxygen and further atoms, a ($C_1$-$C_4$ alkoxy)methyl group, an alkylthioalkyl group in which each alkyl part is $C_1$-$C_4$, a ($C_6$ or $C_{10}$ carbocyclic aryl)-$C_1$-$C_3$ alkoxymethyl group or a tri-substituted silyl group, said three substituents being the same or different and are $C_1$-$C_4$ alkyl, phenyl or naphthyl group;

$R^2$ and $R^3$ are independently selected from the group consisting of hydrogen atoms and $C_1$-$C_4$ alkyl groups or $R^2$ and $R^3$, together with the carbon atom to which they are attached, represent a $C_3$-$C_7$ cycloalkyl group;

$R^4$ and $R^5$ are independently selected from the group consisting of groups of formula $-R^{10}$;

$R^6$ represents a hydrogen atom or a $C_1$-$C_4$ alkyl group;

$R^7$ represents a $C_1$-$C_{12}$ alkyl group, a $C_1$-$C_{12}$ alkyl group having at least one substituent selected from the group consisting of substituents (b):
(b) halogen atoms, $C_1$-$C_4$ alkoxy groups, groups of formula $-OR^{10}$, $C_1$-$C_6$ aliphatic carboxylic acyl groups and $C_6$ or $C_{10}$ carbocyclic aryl carboxycyclic acyl groups, a $C_3$-$C_{12}$ alkenyl group, a $C_3$-$C_{12}$ alkenyl group having at least one substituent selected from the group consisting of substituents (b), a $C_3$-$C_{12}$ alkynyl group, a $C_3$-$C_{12}$ alkynyl group having at least one substituent selected from the group consisting of substituents (b) or a group of formula $-D-R^8$,
where:
D represents a single bond, a $C_1$-$C_6$ alkylene group, a $C_2$-$C_6$ alkenylene group or a $C_1$-$C_6$ alkylene or alkenylene group in which the carbon chain is interrupted by at least one oxygen or sulfur atom, or by a $C_3$-$C_7$ cycloalkylene group; and $R^8$ represents a $C_3$-$C_{10}$ cycloalkyl group, a $C_3$-$C_{10}$ cycloalkyl group having at least one $C_1$-$C_6$ alkyl substituent, a $C_5$-$C_{10}$ cycloalkenyl group, a $C_6$ or $C_{10}$ carbocyclic aryl group or a 5- or 6-membered heterocyclic group having 1 or 2 oxygen and/or sulfur hetero atoms;

A represents a single bond, a $C_1$-$C_7$ alkylene group, a $C_1$-$C_7$ alkylene group having at least one fluorine substituent, a group of formula $-CH=CH-(CH_2)_n-$ where n is 0 or an integer from 1 to 5, or a group of formula $-(CH_2)_p-E-(CH_2)_q-$, where:
p is 0 or an integer from 1 to 3,
q is an integer from 1 to 3, and
E is an oxygen or sulfur atom; and B represents a group of formula $-CH_2CH_2-$, $-CH=CH-$ or $-C\equiv C-$,
and pharmaceutically acceptable salts thereof.

24. A composition as claimed in claim 23, wherein the bond represented by the dotted line is a double bond at the 2-position.

25. A composition as claimed in claim 23, wherein:
$R^1$ represents a carboxy group, a hydroxymethyl group, a carbamoyl group or a carbamoyl group having a phenyl substituent, and, where $R^1$ represents a carboxy group, $C_1$-$C_{10}$ alkyl esters thereof;
$R^2$ and $R^3$ are independently selected from the group consisting of hydrogen atoms and $C_1$-$C_4$ alkyl groups;
$R^4$ and $R^5$ are independently selected from the group consisting of hydrogen atoms, tetrahydropyranyl groups, dimethyl-t-butylsilyl groups and benzoyl groups;
$R^6$ represents a hydrogen atom or a methyl group;
$R^7$ represents a $C_3$-$C_{10}$ alkyl group, a $C_3$-$C_{10}$ alkyl group having a $C_1$-$C_4$ alkoxy substituent, a $C_3$-$C_{10}$ alkenyl group, a $C_3$-$C_8$ alkynyl group or a group of formula $-D-R^8$, where
D represents a single bond, a $C_1$-$C_4$ alkylene group, an oxymethylene group or a thiomethylene group, and
$R^8$ represents a $C_3$-$C_{10}$ cycloalkyl group, a thienyl group, a phenyl group or a substituted phenyl group having at least one substituent selected from the group consisting of halogen atom, $C_1$-$C_4$ alkyl and trifluoromethyl substituents;

A represents a $C_1$–$C_5$ alkylene group, a fluorinated $C_1$–$C_5$ alkylene group or a group of formula —$(CH_2)_p$—E—$(CH_2)_q$— where:
E represents an oxygen or sulfur atom,
p is 1 or 2, and
p is 1 or 2; and
the dotted line represents a double bond at the 2-position.

26. A composition as claimed in claim 23, wherein said prostaglandin derivative is selected from the group consisting of:
3-(1,1-methylene-4-carboxybutyl)-6β-(3α-hydroxy-1-octenyl)-7α-hydroxybicyclo[3.3.0]oct-2-ene
3-(1,1-methylene-4-carboxybutyl)-6β-(3α-hydroxy-4-methyl-1-octenyl)-7α-hydroxybicyclo[3.3.0]oct-2-ene
3-(1,1-methylene-4-carboxybutyl)-6β-(3α-hydroxy-5-methyl-1-nonenyl)-7α-hydroxybicyclo[3.3.0]oct-2-ene
3-(1,1-methylene-4-carboxybutyl)-6β-(3α-hydroxy-4,4-dimethyl-1-octenyl)-7α-hydroxybicyclo[3.3.0]oct-2-ene
3-(1,1-methylene-4-carboxybutyl)-6β-(3α-hydroxy-4,4-dimethyl-1,8-nonadienyl)-7α-hydroxybicyclo[3.3.0]oct-2-ene
3-(1,1-methylene-4-carboxybutyl)-6β-(3α-hydroxy-5,9-dimethyl-1,8-decadienyl)-7α-hydroxybicyclo[3.3.0]oct-2-ene
3-(1,1-methylene-2-carboxymethoxyethyl)-6β-(3α-hydroxy-4-methyloct-1-en-6-ynyl)-7α-hydroxybicyclo[3.3.0]oct-2-ene
3-(1,1-methylene-2-carboxymethoxyethyl)-6β-(3α-hydroxy-3-cyclopentyl-1-propenyl)-7α-hydroxybicyclo[3.3.0]oct-2-ene
3-(1,1-methylene-4-carboxybutyl)-6β-(3α-hydroxy-3-cyclohexyl-1-propenyl)-7α-hydroxybicyclo[3.3.0]oct-2-ene
3-(1,1-methylene-2-carboxymethoxyethyl)-6β-(3α-hydroxy-3-cyclohexyl-1-propenyl)-7α-hydroxybicyclo[3.3.0]oct-2-ene
3-(1,1-methylene-2-carboxymethoxyethyl)-6β-(3α-hydroxy-4-phenoxy-1-butenyl)-7α-hydroxybicyclo[3.3.0]oct-2-ene
and pharmaceutically acceptable salts and esters thereof.

27. A method of treating a mammal suffering from a thrombotic or ulcerative condition by administering thereto an effective amount of a prostaglandin derivative, wherein the prostaglandin derivative is selected from the group consisting of compounds of formula (I):

(I)

in which:
the dotted line represents a double bond at either the 2-position or the 3-position;
$R^1$ represents a carboxy group, an ester thereof selected from the group consisting of a $C_1$–$C_{10}$ alkyl ester, a $C_3$–$C_7$ cycloalkyl ester, a ($C_6$ or $C_{10}$ carbocyclic aryl)-$C_1$–$C_3$ alkyl ester, a phenyl ester, a phenyl ester having at least one substituent selected from the group consisting of $C_1$–$C_4$ alkyl groups and benzoylamino groups, a benzhydryl ester, a phenacyl ester and a geranyl ester,
a tetrazolyl group, a carbamoyl group, a carbamoyl group having 1 or 2 substituents selected from the group consisting of substituents (a):
(a) $C_1$–$C_4$ alkyl groups, $C_1$–$C_6$ aliphatic carboxylic acyl groups, $C_6$ or $C_{10}$ carbocyclic aryl carboxylic acyl groups, $C_1$–$C_4$ alkanesulfonyl groups, $C_6$–$C_{10}$ carbocyclic arylsulfonyl groups, phenyl groups and phenyl groups having at least one $C_1$–$C_4$ alkyl substituent,
a formyl group, a group of formula where:
G represents an oxygen or a sulfur atom;
$R^9$ represents a $C_1$–$C_4$ alkyl group; and
T represents a $C_2$–$C_5$ alkylene group,
or a group of formula —$CH_2OR^{10}$ or —$COCH_2OR^{10}$
where:
$R^{10}$ represents a hydrogen atom, a $C_2$–$C_5$ aliphatic acyl group, a $C_6$ or $C_{10}$ carbocyclic aryl carboxylic acyl group, a ($C_6$ or $C_{10}$ carbocyclic aryl)-$C_1$–$C_3$ alkyl group, a heterocyclic group having 5 or 6 ring atoms of which 1 or 2 are heteroatoms selected from the group consisting of oxygen and sulfur atoms, a ($C_1$–$C_4$ alkoxy)methyl group, an alkylthioalkyl group in which each alkyl part is $C_1$–$C_4$, a ($C_6$ or $C_{10}$ carbocyclic aryl)-$C_1$–$C_3$ alkoxymethyl group or a tri-substituted silyl group, said three substituents being the same or different and are $C_1$–$C_4$ alkyl, phenyl or naphthyl group;
$R^2$ and $R^3$ are independently selected from the group consisting of hydrogen atoms and $C_1$–$C_4$ alkyl groups or $R^2$ and $R^3$, together with the carbon atoms to which they are attached, represent a $C_3$–$C_7$ cycloalkyl group;
$R^4$ and $R^5$ are independently selected from the group consisting of groups of formula —$R^{10}$;
$R^6$ represents a hydrogen atom or a $C_1$–$C_4$ alkyl group;
$R^7$ represents a $C_1$–$C_{12}$ alkyl group, a $C_1$–$C_{12}$ alkyl group having at least one substituent selected from the group consisting of substituents (b):
(b) halogen atoms, $C_1$–$C_4$ alkoxy groups, groups of formula —$OR^{10}$, $C_1$–$C_6$ aliphatic carboxylic acyl groups and $C_6$ or $C_{10}$ carbocyclic aryl carboxycyclic acyl groups,
a $C_3$–$C_{12}$ alkenyl group, a $C_3$–$C_{12}$ alkenyl group having at least one substituent selected from the group consisting of substituents (b), a $C_3$–$C_{12}$ alkynyl group, a $C_3$–$C_{12}$ alkynyl group having at least one substituent selected from the group consisting of substituents (b) or a group of formula —D—$R^8$, where:

D represents a single bond, a $C_1$–$C_6$ alkylene group, a $C_2$–$C_6$ alkenylene group or a $C_1$–$C_6$ alkylene or alkenylene group in which the carbon chain is interrupted by at least one oxygen or sulfur atom; or by a $C_3$–$C_7$ cycloalkylene group; and $R^8$ represents a $C_3$–$C_{10}$ cycloalkyl group, a $C_3$–$C_{10}$ cycloalkyl group having at least one $C_1$–$C_6$ alkyl substituent, a $C_5$–$C_{10}$ cycloalkenyl group, a $C_6$ or $C_{10}$ carbocyclic aryl group or a 5- or 6-membered heterocyclic group having 1 or 2 oxygen and/or sulfur hetero atoms;

A represents a single bond, a $C_1$–$C_7$ alkylene group, a $C_1$–$C_7$ alkylene group having at least one fluorine substituent, a group of formula —CH=CH—$(CH_2)_n$— where n is 0 or an integer from 1 to 5, or a group of formula —$(CH_2)_p$—E—$(CH_2)_q$—, where:

p is 0 or an integer from 1 to 3, q is an integer from 1 to 3, and

E is an oxygen or sulfur atom; and

B represents a group of formula —$CH_2CH_2$—, —CH=CH— or —C≡C—, and pharmaceutically acceptable salts thereof.

28. A method as claimed in claim 27, wherein the bond represented by the dotted line is a double bond at the 2-position.

29. A method as claimed in claim 27, wherein:

$R^1$ represents a carboxy group, a hydroxymethyl group, a carbamoyl group or a carbamoyl group having a phenyl substituent, and, where $R^1$ represents a carboxy group, $C_1$–$C_{10}$ alkyl esters thereof;

$R^2$ and $R^3$ are independently selected from the group consisting of hydrogen atoms and $C_1$–$C_4$ alkyl groups;

$R^4$ and $R^5$ are independently selected from the group consisting of hydrogen atoms, tetrahydropyranyl groups, dimethyl-t-butylsilyl groups and benzoyl groups;

$R^6$ represents a hydrogen atom or a methyl group;

$R^7$ represents a $C_3$–$C_{10}$ alkyl group, a $C_3$–$C_{10}$ alkyl group having a $C_1$–$C_4$ alkoxy substituent, a $C_3$–$C_{10}$ alkenyl group, a $C_3$–$C_8$ alkynyl group or a group of formula —D—$R^8$, where D represents a single bond, a $C_1$–$C_4$ alkylene group, an oxymethylene group or a thiomethylene group, and $R^8$ represents a $C_3$–$C_{10}$ cycloalkyl group, a thienyl group, a phenyl group or a substituted phenyl group having at least one substituent selected from the group consisting of halogen atom, $C_1$–$C_4$ and trifluoromethyl substituents;

A represents a $C_1$–$C_5$ alkylene group, a fluorinated $C_1$–$C_5$ alkylene group or a group of formula —$(CH_2)_p$—E—$(CH_2)_q$— where:

E represents an oxygen or sulfur atom, p is 1 or 2, and q is 1 or 2; and the dotted line represents a double bond at the 2-position.

30. A method as claimed in claim 27, wherein said prostaglandin derivative is selected from the group consisting of:

3-(1,1-methylene-4-carboxybutyl)-6β-(3α-hydroxy-1-octenyl)-7α-hydroxybicyclo[3.3.0]oct-2-ene 3-(1,1-methylene-4-carboxybutyl)-6β-(3α-hydroxy-4-methyl-1-octenyl)-7α-hydroxybicyclo[3.3.0]oct-2-ene 3-(1,1-methylene-4-carboxybutyl)-6β-(3α-hydroxy-5-methyl-1-nonenyl)-7α-hydroxybicyclo[3.3.0]oct-2-ene 3-(1,1-methylene-4-carboxybutyl)-6β-(3α-hydroxy-4,4-dimethyl-1-octenyl)-7α-hydroxybicyclo[3.3.0]oct-2-ene 3-(1,1-methylene-4-carboxybutyl)-6β-(3α-hydroxy-4,4-dimethyl-1,8-nonadienyl)-7α-hydroxybicyclo[3.3.0]oct-2-ene 3-(1,1-methylene-4-carboxybutyl)-6β-(3α-hydroxy-5,9-dimethyl-1,8-decadienyl)-7α-hydroxybicyclo[3.3.0]oct-2-ene 3-(1,1-methylene-2-carboxymethoxyethyl)-6β-(3α-hydroxy-4-methyloct-1-en-6-ynyl)-7α-hydroxybicyclo[3.3.0]oct-2-ene 3-(1,1-methylene-2-carboxymethoxyethyl)-6β-(3α-hydroxy-3-cyclopentyl-1-propenyl)-7α-hydroxybicyclo[3.3.0]-oct-2-ene 3-(1,1-methylene-4-carboxybutyl)-6β-(3α-hydroxy-3-cyclohexyl-1-propenyl)-7α-hydroxybicyclo[3.3.0]oct-2-ene 3-(1,1-methylene-2-carboxymethoxyethyl)-6β-(3α-hydroxy-3-cyclohexyl-1-propenyl)-7α-hydroxybicyclo[3.3.0]oct-2-ene 3-(1,1-methylene-2-carboxymethoxyethyl)-6β-(3α-hydroxy-4-phenoxy-1-butenyl)-7α-hydroxybicyclo[3.3.0]oct-2-ene and pharmaceutically acceptable salts and esters thereof.

* * * * *

UNITED STATES PATENT AND TRADEMARK OFFICE
CERTIFICATE OF CORRECTION

PATENT NO. : 4,777,184
DATED : October 11, 1988
INVENTOR(S) : KOJIMA et al It is certified that error appears in the above-identified patent and that said Letters Patent is hereby corrected as shown below:

Column 6, line 47, after "6-methyl-5-octenyl," insert the following:

-- 2,6-dimethyl-5-octenyl, 6-ethyl-5-octenyl,--.

Columns 15/16, (Table 1 continued), after "64a/b......", insert the following:

-- 65a/b  CHO   H   H   1,6-diMeHept-5-enyl  -CH=CH --.

Column 34, line 43, change "fron" to --from--.

Column 99, line 6 (Claim 25), change "p" to -- q --.

Signed and Sealed this

Twenty-fourth Day of November, 1992

Attest:

DOUGLAS B. COMER

Attesting Officer

Acting Commissioner of Patents and Trademarks